US008461413B2

(12) United States Patent
Frankard

(10) Patent No.: US 8,461,413 B2
(45) Date of Patent: Jun. 11, 2013

(54) PLANTS HAVING ENHANCED YIELD-RELATED TRAITS AND A METHOD FOR MAKING THE SAME

(75) Inventor: Valerie Frankard, Waterloo (BE)

(73) Assignee: CropDesign N.V., Zwijnaarde (BE)

( * ) Notice: Subject to any disclaimer, the term of this patent is extended or adjusted under 35 U.S.C. 154(b) by 522 days.

(21) Appl. No.: 12/524,746

(22) PCT Filed: Jan. 30, 2008

(86) PCT No.: PCT/EP2008/051154
§ 371 (c)(1),
(2), (4) Date: Aug. 6, 2009

(87) PCT Pub. No.: WO2008/092910
PCT Pub. Date: Aug. 7, 2008

(65) Prior Publication Data
US 2010/0011464 A1    Jan. 14, 2010

Related U.S. Application Data

(60) Provisional application No. 60/890,845, filed on Feb. 21, 2007.

(30) Foreign Application Priority Data

Jan. 30, 2007    (EP) .................................... 07101436

(51) Int. Cl.
| *A01H 1/00* | (2006.01) |
| *A01H 5/00* | (2006.01) |
| *A01H 5/10* | (2006.01) |
| *C12N 15/82* | (2006.01) |
| *C12N 15/63* | (2006.01) |
| *C12N 15/29* | (2006.01) |

(52) U.S. Cl.
USPC ........ 800/278; 800/298; 800/320; 800/320.1; 800/320.2; 800/320.3; 435/320.1; 435/410; 435/419; 435/468; 536/23.6

(58) Field of Classification Search
None
See application file for complete search history.

(56) References Cited

U.S. PATENT DOCUMENTS

| 7,235,710 | B2 * | 6/2007 | Hatzfeld et al. .............. 800/278 |
| 2004/0060079 | A1 | 3/2004 | Tanaka et al. |
| 2004/0148655 | A1 | 7/2004 | Choe et al. |
| 2006/0236419 | A1 * | 10/2006 | La Rosa et al. .............. 800/278 |
| 2007/0089183 | A1 | 4/2007 | Poovaiah et al. |

FOREIGN PATENT DOCUMENTS

JP    11-290082    10/1999

OTHER PUBLICATIONS

Hong et al, The Plant Cell, 2005, col., 17, pp. 2243-2254.*
Machine Translation of JP11290082-A, Oct. 1999.*
Du and Poovaiah, Nature, Sep. 29, 2005, vol. 437, pp. 741-745.*
Choe et al, The Plant Journal, Jun. 2001, Vo. 26, No. 6, pp. 573-582.*
Hong et al, The Plant Cell, vol. 17, Aug. 2005, pp. 2243-2254.*
Choe, S., et al., "Overexpression of *DWARF4* in the Brassinosteroid Biosynthetic Pathway Results in Increased Vegetative Growth and Seed Yield in *Arabidopsis*", The Plant Journal, vol. 26, No. 6, (2001), pp. 573-582.
Klahre, U., et al., "The *Arabidopsis DIMINUTO/DWARF1* Gene Encodes a Protein Involved in Steroid Synthesis", The Plant Cell, vol. 10, (1998), pp. 1677-1690.
Sakamoto, T., "Phytohormones and Rice Crop Yield: Strategies and Opportunities for Genetic Improvement", Transgenic Research, vol. 15, (2006), pp. 399-404.
Takahashi, T., et al., "The *DIMINUTO* Gene of *Arabidopsis* is Involved in Regulating Cell Elongation", Genes and Development, vol. 9, (1995), pp. 97-107.
Yokota, T., "The Structure, Biosynthesis and Function of Brassinosteroids", Trends in Plant Science, vol. 2, No. 4, (1997), pp. 137-143.
Hong et al., "The Rice brassinosteroid-deficient dwarf2 Mutant, Defective in the Rice Homolog of *Arabidopsis* DIMINUTO/DWARF1, Is Rescued by the Endogenously Accumulated Alternative Bioactive Brassinosteroid, Dolichosterone", The Plant Cell, vol. 17, (2005), pp. 2243-2254.
Choe et al., "The *Arabidopsis* dwarf1 mutant is defective in the conversion of 24-methylenecholesterol to campesterol in brassinosteroid biosynthesis", Plant Physiol., vol. 119, (1999), pp. 897-907.
Fraaije, M. W., et al., "A Novel Oxidoreductase Family Sharing a Conserved FAD-Binding Domain", TIBS, vol. 23, (1998), pp. 206-207.
"FAD-binding, type 2", SuperFamily Accession SSF56176, InterPro Accession IPR016166, downloaded May 24, 2012.
"FAD-linked oxidase, N-terminal", InterPro Accession IPR006094, downloaded May 24, 2012.

* cited by examiner

*Primary Examiner* — Eileen B O Hara
(74) *Attorney, Agent, or Firm* — Novak Druce Connolly Bove + Quigg LLP

(57) ABSTRACT

The present invention relates generally to the field of molecular biology and concerns a method for enhancing various economically important yield-related traits in plants. More specifically, the present invention concerns a method for increasing seed yield in plants by increasing expression in a plant of a nucleic acid sequence encoding a Dwarf1 (DWF1) polypeptide. The present invention also concerns plants having increased expression of a nucleic acid sequence encoding a DWF1 polypeptide, which plants have increased seed yield relative to control plants. The invention also provides constructs useful in performing the methods of the invention.

28 Claims, 31 Drawing Sheets

N-terminal hydrophobic anchor domain

```
                                                        Pyrophosphate
Arath_DWF1      SFEKRQKEHDENVKKVIKRLKGRDAS-KDGLVCTARKPWIAVGMRNVDYKRARHFEVDLG
Brara_DWF1      SYEKRQKEHDQNVNKVIKRLKGRDAS-KDGLVCTARKPWIAVGMRNVDYKRARHFEVDLS
Glyma_DWF1      SYKTRQKEHDENVKKVIKRLKQRNPS-KDGLVCTARKPWIAVGMRNVDYKRARHFEVDLS
Pissa_DWF1      SFKTRQKEHDENVQKVVNRLKKRNPS-KDGLVCTARKPWIAVGMRNVDYKRARHFEVDLS
Poptr_DWF1      SYKQRQKEHDENVKKVVKRLKERNPS-KDGLVCTARKPWIAVGMRNVDYKRARHFEVDLS
Goshi_DWF1      SYKQRQKEHDENVLKVVKRLKQRNPK-KDGLVCTARKPWIAVGMRNVDYKRARHYEVDLS
Lyces_DWF1      SYKQRQKEHDENVKKVVKRLKERNAS-KDGLVCTARKPWVAVGMRNVDYKRARHFEVDLS
Zinel_DWF1      SYKQRQKEHEENVKKVVKRLQERNPS-KDGRVCTARKPWIAVGMRNVDYKRARHFEVDLS
Sacof_DWF1      SEKKRQKQHDENVQKVVKRLKQRNPK-KDGLVCTARKPWIAVGMRNVDYKRARHFEVDLS
Zeama_DWF1      SEKKRQKQHDENVQKVVKRLKQRNPK-KDGLVCTARKPWIAVGMRNVDYKRARHFEVDLS
Orysa_DWF1      SEKKRQKEHDDNVQKVVKRLKQRNPK-KDGLVCTARKPWIAVGMRNVDYKRARHFEVDLS
Triae_DWF1      SEKKRQKEHEDNVQKVVKRLKQRNPK-KDGLVCTARKPWIAVGMRNVDYKRVRHFEVDLS
Danre_dhcr24    KMCSAPKQHDQRVRDIQRQVREWRKDGGKKYMCTGRPGWLTVSLRVGKYKKTHKNIMIN-
Homsa_DWF1      KLSSAPRLHEQRVRDIQKQVREWKEQGSKTFMCTGRPGWLTVSLRVGKYKKTHKNIMIN-
                  .    :: .. :  :       .           .   *:: :*. :*    ..

SSF56176        XXXXXXXXXXXXXXXXXXXXXXXXXXXXXXXXXXXXXXXXXXXXXXXXXXXXXXXXXXXX
IPR006094                                                       YYYY
Choe et al.                ZZZZZZZZZZZZZZZZZZZZZZZZZZZZZZZZZZZZZZZZZZZZZZ
```

FIGURE 4B

```
                                                                            ADP  Isoalloxazine
Arath_DWF1      EFRNILEINKEKMTARVEPLVNMGQISRATVPMNLSLAVVAELDDL TVGGLINGYGIEGS
Brara_DWF1      AFRNILKIDKDRMIARVEPLVNMGQISRVTVPMNLSLAVVAELDDL TVGGLINGYGIEGS
Glyma_DWF1      AFRNVLEIDKERMIARVEPLVNMGQISRVTVPMNLSLAVVAELDDL TVGGLINGYGIEGS
Pissa_DWF1      PFRNILDIDKERMIARVEPLVNMGQITRVTVPMNLSLAVVAELDDL TVGGLINGYGIEGS
Poptr_DWF1      SFRNILEIDRERMVARVEPLVNMGQISRASVPMNLSLAVVAELDDL TVGGLINGYGIEGS
Goshi_DWF1      AFRNILEIDKQRMIARVEPLVNMGQITRVTVPMNLSLAVVAELDDL TVGGLINGYGIEGS
Lyces_DWF1      PFRNVLNIDTERMIAKVEPLVNMGQISRVTVPLNVSLAVVAELDDL TVGGLINGYGIEGS
Zinel_DWF1      AFRNILEINQETMIAKCEPLVNMGRITRATVPLNLALAAVAELDDL TVGGLINGYGIEGS
Sacof_DWF1      SFRNILEIDKERMVAKVEPLVNMGQITRATCPMNLALAVVAELDDL TVGGLINGYGIEGS
Zeama_DWF1      SFRNILEIDKERMVAKVEPLVNMGQITRATCPMNLALAVVAELDDL TVGGLINGYGIEGS
Orysa_DWF1      AFRNILEIDRERMVAKVEPLVNMGQITRATCPMNLALAVVAELDDL TVGGLINGYGIEGS
Triae_DWF1      AFRNILEIDAERMVAKVEPLVNMGQISRATCPMNLSLAVVAELDDL TVGGLINGYGIEGS
Danre_dhcr24    -MMDILEVDTKRKVVRVEPLANMGQVTALLNSIGWTLPVLPELDDL TVGGLVMPELDDL IMGTGIESS
Homsa_DWF1      -LMDILEVDTKKQIVRVEPLVTMGQVTALLTSIGWTLPVLPELDDL TVGGLIMGTGIESS
                 ::  ::*.  .   ::  .:****..  ** :::.* *****.:  ****..:*****

SSF56176        XXXXXXXXXXXXXXXXXXXXXXXXXXXXXXXXXXXXXXXXXXXXXXXXXXXXXXXXXXXX
IPR006094       YYYYYYYYYYYYYYYYYYYYYYYYYYYYYYYYYYYYYYYYYYYYYYYYYYYYYYYYYYYY
Choe et al.     ZZZZZZZZZZZZZZZZZZZZZZZZZZZZZZZZZZZZZZZZZZZZZZZZZZZZZZZZZZZZ
```

FIGURE 4C

```
                                                                Adenine
Arath_DWF1       SHIYGLFADTVEAYEIVLAGGELVRATRDNEYSDLYYAIPWSQTL GLLVAAEIRLIKVK
Brara_DWF1       SHVHGLFTDTVEAYEIVLAGGELVRATRDNEYSDLFYAIPWSQTL GLLVAAEIRLVHIK
Glyma_DWF1       SHKYGLFADTVVAYEIILADGTLVRATKDNEYSDLYYAIPWSQTL GLLVAAEIRLIPVK
Pissa_DWF1       SHKYGLFSDTVVAFEIILADGSLVKATKDNEYSDLFYAIPWSQTL GLLVAAEVKLIPIK
Poptr_DWF1       SHIYGLFSDTVVAYEIVLADGQVVRATKDNEYSDLFYAIPWSQTL GLLVSAEIKLIPVK
Goshi_DWF1       SHIYGLFSDTVVAYEIVLADGRVVRATKDNEYSDLFYAIPWSQTL GFLVAAEIKLIPVK
Lyces_DWF1       SHIYGLFSDTVVSYEVVLADGQVVRATKDNEYSDLFYAIPWSQTL GLLVSAEIKLIPIK
Zinel_DWF1       SHLYGLFSDTVVAYEIVLAGGKVVRATKDNEYSDLFYAIPWSQTL GLLVSAEIKLIPIK
Sacof_DWF1       SHLYGLFSDTVVAMEVVLADGRVVRATKDNEYSDLFYGIPWSQTL GFLVSAEIKLIPIK
Zeama_DWF1       SHLYGLFSDTVVAMEVVLADGRVVRATKDNEYSDLFYGIPWSQTL GFLVSAEIKLIPIK
Orysa_DWF1       SHLYGLFSDTVVAVEVVLADGRVVRATKDNEYSDLFYGIPWSQTL GFLVSAEIKLIPIK
Triae_DWF1       SHIYGLFSDTVVALEIVLADGRVVRATKDNEYSDLFYGVPWSQTL GFLVSAEIKLIPIK
Danre_dhcr24     SHIYGLFQHICVAFELVLADGSLVRCTE-KENSDLFVRCTP-SENSDLFYAVPWSCGTL GFLVAAEIRIIPAQ
Homsa_DWF1       SHKYGLFQHICTAYELVLADGSFVRCTP-SENSDLFYAVPWSCGTL GFLVAAEIRIIPAK
                 **  :*** .  . * **::*.* .*.: *.  . * ***** *  : ***:*::* :

SSF56176         YYYYYYYYYYYYYYYYYYYYYYYYYYYYYYYYYYYYYYYYYYYYYYYYYYYYYYYYYYYY
IPR006094        XXXXXXXXXXXXXXXXXXXXXXXXXXXXXXXXXXXX
Choe et al.      ZZZZZZZZZZZZZZZZZZZZZZZZZZZZZZZZZZZZZZZZZZZZZZZZZZZZZZZZZZZZ
```

FIGURE 4D

```
Arath_DWF1      EYMRLTYIPVKGDLQALAQGYIDSFAPKDGD---KSKIPDFVEGMVYNPTEGVMMVGTYA
Brara_DWF1      EYMKLTYIPVKGDLQTIAQGYMDSFAPRDRD---PAKIPDFVEGMVYSPSEGVMMTGTYA
Glyma_DWF1      EYMKLTYKPVVGTLQDLAQAYCDSFAPRDGDQDNEEKVPDFVEGMIYTPTEGVMMTGRYA
Pissa_DWF1      EYMKLTYKPVVGNLKDIAQAYSDSFAPRDGDQDNDEKVPDFVETMIYSPTRAVCMTGRYA
Poptr_DWF1      EYMKLTYKPVVGNLKELAQAYIDSFAPRDGDQDNPSKVPDFVETMIYNSTDGVMMTGRYA
Goshi_DWF1      EYMRLTYTPVVGNLQDLAQGYMDSFAPRDGDQDNPEKVPDFVEGMVYSPTEGVFMTGRYA
Lyces_DWF1      EYMRLTYKPVVGNLKEIAQAYMDSFSPRDGDQDNHEKVPDFVETMVYTPTEAVCMTGRYA
Zinel_DWF1      EYMKLTYTPVRGSVKELGKAYIDSFAPRFGE-ENSEEVPDFVEGMIYNPHEGVCMTGKYA
Sacof_DWF1      EYMKLTYIPVKGSLKEIAQADSFAPRDGD----PAKVPDFVEGMVYTESEGVMMTGVYA
Zeama_DWF1      EYMKLTYTPVKGGLKEIAQAYADSFAPRDGD----PAKVPDFVEGMVYTESEGVMMTGVYA
Orysa_DWF1      EYMRLTYTPVKGSLKEIAQGYCDSFAPRDGD----PAKVPDFVEGMVYTENEGVMMTGVYA
Triae_DWF1      EYMRLTYTPVKGPLKEVAQAYADAVAPRDGD----PAKVPDFVEGMVYSATEGVMMTGVYA
Danre_dhcr24    KWVKLHYEPVRG-LDAICKKFAEESANKEN--------QFVEGLQYSRDEAVIMTGVMT
Homsa_DWF1      KYVKLRFEPVRG-LEAICAKFTHESQRQEN--------HFVEGLLYSLDEAVIMTGVMT
                  * .  ::.*  ..   *  **  ..          .   *** ..  *.**.*

Substrate
                binding domain
```

FIGURE 4E

| | |
|---|---|
| Arath_DWF1 | SKEEAKKKGNKINNVGWWFKPWFYQHAQTALKKG-QFVEYIPTREYYHRHTRCLYWEGKL |
| Brara_DWF1 | SREEAKRKGNKINNVGWWFKPWFYQYAQTALKKG-EFVEYIPTREYYHRHTSSLYWEGKL |
| Glyma_DWF1 | SKEEAKKKGNKINSVGWWFKPWFYQHAQTALKKG-EFVEYIPTREYYHRHTRCLYWEGKL |
| Pissa_DWF1 | SKEEAKKKGNKINNVGWWYKTWFYQHAETALKKG-LFVEYIPTREYYHRHTRCLYWEGKL |
| Poptr_DWF1 | SKEEAKKKGNVINNVGWWFKPWFYQHAQTALKKG-EFVEYIPTREYYHRHTRCLYWEGKL |
| Goshi_DWF1 | SKEEAKKKGNKINNVGWWFKPWFYQHAQTALKKG-EFVEYIPTREYYHRHTRCLYWEGKL |
| Lyces_DWF1 | SKEEAKKKGNVINNVGWWFKTWFYQHAQTALKKG-EFVEYIPTREYYHRHTRCLYWEGKL |
| Zinel_DWF1 | SKEEAEKKGNKINSVGWWFKPWFYQHAQTALTKG-EFVEYIPTREYYHRHTRCLYWEGKL |
| Sacof_DWF1 | SKEEAKKKGNKINCVGWWFKPWFYQHAQTALKRG-EFVEYIPTREYYHRHTRCLYWEGKL |
| Zeama_DWF1 | SKEEAKKKGNKINCVGWWFKPWFYQHAQTALNRG-EFVEYIPTREYYHRHTRCLYWEGKL |
| Orysa_DWF1 | SKEEAKKKGNKINCVGWWFKPWFYQHAQTALKKG-EFVEYIPTREYYHRHTRCLYWEGKL |
| Triae_DWF1 | SKEEAKKKGNKINSVGWWFKPWFYQHAQTALKKG-EFVEYIPTREYYHRHTRCLYWEGKL |
| Danre_dhcr24 | DHAEP----DKTNCIGYYYKPWFFRHVESFLKQNRVAVEYIPLRHYYHRHTRSIFWELQD |
| Homsa_DWF1 | DEAEP----SKLNSIGNYYKPWFFKHVENYLKTNREGLEYIPLRHYYHRHTRSIFWELQD |
| | *  .   *  . :*  ::*.*  *   :*:::: .*.   *:****  *.******* .:** :: |

Substrate binding domain

FIGURE 4F

```
Arath_DWF1      ILPFGDQFWFRYLLGWLMPPKVSLLKATQGEAIRNYYHDMHVIQDMLVPLYKVGDALEWV
Brara_DWF1      ILPFGDQFWFRFLFGWLMPPKVSLLKATQGEAIRNYYHEMHVIQDMLVPLYKVGDALKWV
Glyma_DWF1      ILPFADQFWFRYLFGWLMPPKVSLLKATQGDAIRNYYHEMHVIQDMLVPLYKVGDALEWV
Pissa_DWF1      ILPFGDQFWFRFLFGWLMPPKVSLLKATQGEAIRNYYHEMHVIQDMLVPLYKVGDALEWV
Poptr_DWF1      ILPFADQWWFRFLLGWMMPPKVSLLKATQGEAIRNYYHEMHVIQDMLVPLYKVGDALEWV
Goshi_DWF1      ILPFGDQWWFRFLLGWLMPPKVSLLKATQGESIRNYYHEMHVIQDMLVPLYKVGDALEWV
Lyces_DWF1      ILPFGDQWWFRFLFGWAMPPKVSLLKATQGEYIRNYYHENHVIQDMLVPLYKVGDALEWV
Zinel_DWF1      ILPFGDQWWFRFLLGWMMPPKVSLLKATQGEAIRNYYHEMHVIQDMLVPLYKVPDALEWV
Sacof_DWF1      ILPFGDQFWFRFLLGWLMPPKVSLLKATQGEAIRNYYHDNHVIQDMLVPLYKVGDALEFV
Zeama_DWF1      ILPFGDQFWFRFLLGWLMPPKVSLLKATQGEAIRNYYHDNHVIQDMLVPLYKVGDALEFV
Orysa_DWF1      ILPFGDQFWFRFLLGWLMPPKVSLLKATQGESIRNYYHDNHVIQDMLVPLYKVGDALEFV
Triae_DWF1      ILPFGDQFWFRFLFGWLMPPKVSLLKATQGDAIRNYYHDNHVIQDMLVPLYKVGDALEFV
Danre_dhcr24    IIPFGNNPLFRYVFGWMMVPPKISLLKLTQGETIRKLYEQHHVVQDMLVPMKDIKAAIQRF
Homsa_DWF1      IIPFGNNPIFRYLFGWMVPPKISLLKLTQGETLRKLYEQHHVVQDMLVPMKCLQQALHTF
                *:*  :  ::     *  :  *::*****  :   * :   :    *  *  *    .
```

Substrate binding domain

FIGURE 4G

```
Arath_DWF1    HREMEVYPIWLCPHKLFKQPIKGQIYPEPGFEYENRQGDTEDAQMYTDVGVYYAPGCVLR
Brara_DWF1    DREMEVYPLWLCPHKLFKQPVKSMINPEPGFEYEMRQGDTEDAQMYTDVGVYYAPGPVLR
Glyma_DWF1    HREMEVYPIWLCPHKLFKLPVKTMIYPEPGFELHRRQGDTQTAQMYTDVGVYYAPGPVLR
Pissa_DWF1    DREMEVYPIWLCPHKLFKLPIKTMIYPEAGFELQRRQGDTQNAQMFTDVGVYYAPGPVLR
Poptr_DWF1    DREMEVYPIWLCPHRLFKLPVKTMVYPEPGFEHQRRQGDTSYAQMYTDVGVYYSPGPVLR
Goshi_DWF1    HHEMEIYPIWLCPHRLFKLPVKTMVYPEPGFEQHRRQGDTPYAQMFTDVGVYYAPGPVLR
Lyces_DWF1    HREMEVYPLWLCPHRLYRLPLKTMVYPEPGFELQKRQGDTKYAQMYTDVGVYYAPGPILR
zinel_DWF1    DREMEVYPLWLCPHRLYKLPYKTMVYPEPGFEEHCRQGDTPYAQMYTDVGVYYAPGPVLR
Sacof_DWF1    HREMEVYPLWLCPHRLYKLPVKTMVYPEPGFEHQHRQGDTSYAQMFTDVGVYYAPAAVLR
Zeama_DWF1    HREMEVYPLWLCPHRLYKLPVKTMVYPEPGFEHQHRQGDASYAQMFTDVGVYYAPGAVLR
Orysa_DWF1    HKEMEVYPLWLCPHRLYKLPVKTMVYPEPGFEHHHRQGDTSYAQMFTDVGVYYAPGAVLR
Triae_DWF1    HHEMEVYPLWLCPHRLFKLPVKTMIYPEPGFEHQQRQGDTSYAQMFTDVGVYYTPACIFR
Danre_dhcr24  HEDIHVYPLWLCPFLLPNQPG--MVHPKG-------DEDELYVDIGAYGEP----K
Homsa_DWF1    QNDIHVYPIWLCPFILPSQPG--LVHPKG-------NEAELYIDIGAYGEP----R
              ..:.::.*******.  *     *  :                  ::  *.:.*   ::

Substrate
binding domain
```

FIGURE 4H

| | |
|---|---|
| Arath_DWF1 | GEEFDGSEAVRRMEKWLIENHGFQPQYAVSELDEKSFWRMFNGELYEECRKKYRAIGTFM |
| Brara_DWF1 | GEVFDGVEAVRKMEQWLIENHGYQPQYAVSELDERSFWRMFDADLYEHCRRKYRAVGTFM |
| Glyma_DWF1 | GEVFDGAEAVRKMENWLIENHGFQPQYAVSELSEKNFWRMFDAGLYEHTRRKYGAVGTFM |
| Pissa_DWF1 | GEVFDGAEAVRKMESWMIENHCFQPQYAVSELNEKNFWRMFDAGLYEHCRRKYGAVGTFM |
| Poptr_DWF1 | GEVFEGADAVRRMEDWLIENHGFQPQYAVSELNEKKFWRMFDADLYEHARKKYGAVGTFM |
| Goshi_DWF1 | GEVFDGAEAVRKLEQWLIKNHSFQPQYAVSELNEKDFWRMFDADLYEHVRRKYGAVGTFM |
| Lyces_DWF1 | GEVFDGIEAVRKLESWLIENHGFQPQYAVSELTEKNFWRMFDGSLYENCRKKYRAIGTFM |
| Zinel_DWF1 | GEVFDGVDAVRRMESWLIENHGFQPQYAVSELNEKNFWRMFDAGLYEQCRNKYGAVGTFM |
| Sacof_DWF1 | GEEFNGVEAVHRLEQWLIENHSYQPQYAVSELNEKDFWRMFDASHYEHCRHKYGAVGTFM |
| Zeama_DWF1 | GEEFNGAEAVHRLEQWLIENHSYQPQYAVSELNEKDSWRMFDASHYEHCRQKYGAVGTFM |
| Orysa_DWF1 | GEEFNGALAVHRLEQWLIENHSYQPQYAVSELNEKDFWRMFDASHYEHCRQKYGAVGTFM |
| Triae_DWF1 | GEEFDGAESVKRLEQWLIENHSYQPQYAVTELNEKDFWRMFDASHYEHCRHKYGAVGTFM |
| Danre_dhcr24 | VKHFEATSSTRQLEKFVRDVHGFQMLYADVYMERKEFWEMFDGTLYHKLREELGCKDAFP |
| Homsa_DWF1 | VKHFEARSCMRQLEKFVRSVHGFQMLYADCYMNREEFWEMFDGSLYHKLREKLGCQDAFP |
| | :*:. .  ::::**:: * .:* ** . .:.*  *. * ***:. . .:* |

Substrate
binding domain

FIGURE 4I

```
Arath_DWF1       SVYYKSKKGRKTEKEVREAEQAHLETAYAEAD----
Brara_DWF1       SIYYKSKKGRKTEKEVREAEQAHLETAYAEGD----
Glyma_DWF1       SVYYKSKKGRKTEKEVQEAEQAHLETAYAEVDQPVD
Pissa_DWF1       SVYYKCKKGRKTEKEVREAEQAHLDTAYAEVDQPAD
Poptr_DWF1       SVYYKSKKGRKTEKEVQEAEQAHLETAYAEAG----
Goshi_DWF1       SVYYKSKKGRKTEKEVQEAEQAHLETAYAEAD----
Lyces_DWF1       SVYYKSKKGKKTEKEVQEAEQETAEVETPEVDEPED
Zinel_DWF1       SVYYKCKKGKKTEKEVQEAEQAQVEVPYAETD----
Sacof_DWF1       SVYYKSKKGRKTEKEVQEAEAAILEPAYADEEA---
Zeama_DWF1       SVYYKSKKGRKTEKEVQEAEAAILEPAYADEA----
Orysa_DWF1       SVYYKSKKGRKTEKEVQEAEAAILEPAYADEA----
Triae_DWF1       SVYYKSKKGRKSEKEVQEAEAAILEPAYADEA----
Danre_dhcr24     EVFDKICKSARH------------------------
Homsa_DWF1       EVYDKICKAARH------------------------
                  ::  *  *   *  ..   :

Substrate
binding domain
```

FIGURE 4J

SEQ ID NO: 1 Saccharum officinarum Dwarf1 Sacof_DWF1 nucleic acid
sequence, contig of CA272246.1, CA178977.1, CA147398.1
ATGGCGGACGTGCATGAACCTTTGGTGCGCCGCAAGAGGAAGAAGGTTTTGGTGGACTACTTCGTG
CAGTTCCGATGGATCCTCGTGATCTTCGTGGTCCTTCCTATTTCATCTCTGATCTACTTCAATATC
TTTCTGGGCGACATGTGGTCTGCCATGAAGTCAGAGAAGAAGCGCCAGAAGCAACACGATGAGAAT
GTGCAGAAGGTTGTGAAGCGGCTCAAGCAGAGGAACCCAAAGAAGGATGGTCTTGTTTGCACAGCC
AGGAAGCCCTGGATTGCTGTTGGCATGCGCAATGTGGACTACAAGCGTGCGAGGCATTTTGAGGTT
GACCTTTCTTCCTTCAGGAACATCCTTGAGATTGACAAAGAGAGGATGGTTGCCAAGGTTGAGCCC
CTTGTAAACATGGGTCAGATAACCAGAGCTACCTGCCCAATGAACCTTGCCCTTGCAGTCGTCGCT
GAGCTTGACGACCTCACTGTTGGTGGGCTGATCAATGGTTATGGAATTGAGGGGAGCTCTCATCTC
TATGGCCTTTTCTCTGACACGGTTGTTGCAATGGAAGTTGTTCTTGCAGATGGCCGGGTTGTTAGG
GCCACCAAGGATAATGAGTACTCTGACCTTTTCTATGGCATTCCTGGTCCCAGGGAACACTTGGG
TTCCTTGTCTCTGCTGAGATCAAGCTGATTCCCATCAAGGAGTACATGAAGCTCACCTACATTCCA
GTGAAGGGAGTCTGAAGGAAATCGCGCAGGCCTATGCTGATTCTTTCGCGCCAAGAGATGGTGAC
CCAGCAAAGGTCCCTGACTTTGTTGAAGGAATGGTGTACACAGAAAGCGAGGGTGTCATGATGACT
GGTGTGTATGCTTCGAAAGAAGAGGCGAAGAAGAAGGGCAACAAGATCAACTGCGTGGGGTGGTGG
TTTAAGCCCTGGTTCTACCAGCATGCTCAGACAGCGCTCAAGAGGGGCGAGTTTGTGGAGTACATC
CCAACAAGAGAGTACTACCACCGCCACACCCGGTGCCTGTACTGGGAGGGAAAGCTGATCCTGCCA
TTCGGTGACCAGTTCTGGTTCAGGTTCCTGCTGGGTTGGCTCATGCCACCAAAGGTGTCTCTTCTG
AAGGCGACTCAGGGTGAGGCTATCAGGAACTACTACCATGACAACCATGTGATCCAGGACATGCTG
GTGCCGCTGTACAAGGTTGGAGATGCTCTCGAGTTCGTGCACCGCGAGATGGAGGTGTATCCTCTG
TGGCTGTGCCCTCACCGCCTGTACAAGCTGCCCGTGAAGACAATGGTGTACCCTGAGCCTGGGTTC
GAGCACCAGCACAGGCAGGGCGACACAAGCTACGCACAGATGTTCACGGACGTGGGCGTGTACTAC
GCTCCTGCTGCGGTCCTAAGGGGAGAGGAGTTCAATGGCGTGGAGGCGGTGCACAGGCTGGAGCAG
TGGCTGATCGAGAACCACAGCTACCAGCCACAGTACGCGGTGTCGGAGCTGAATGAGAAGGACTTC
TGGCGCATGTTTGACGCGTCCCACTACGAGCACTGCCGGCACAAGTATGGGGCGGTGGGCACGTTC
ATGAGCGTGTACTACAAGTCGAAGAAGGGGCGCAAGACGGAGAAGGAGGTGCAGGAGGCGGAGGCG
GCCATCCTGGAGCCGGCCTACGCGGACGAGGCCTAA SEQ ID NO: 2 Saccharum officinarum Dwarf1 Sacof_DWF1 translated
polypeptide sequence
MADVHEPLVRRKRKKVLVDYFVQFRWILVIFVVLPISSLIYFNIFLGDMWSAMKSEKKRQKQHDEN
VQKVVKRLKQRNPKKDGLVCTARKPWIAVGMRNVDYKRARHFEVDLSSFRNILEIDKERMVAKVEP
LVNMGQITRATCPMNLALAVVAELDDLTVGGLINGYGIEGSSHLYGLFSDTVVAMEVVLADGRVVR
ATKDNEYSDLFYGIPWSQGTLGFLVSAEIKLIPIKEYMKLTYIPVKGSLKEIAQAYADSFAPRDGD
PAKVPDFVEGMVYTESEGVMMTGVYASKEEAKKKGNKINCVGWWFKPWFYQHAQTALKRGEFVEYI
PTREYYHRHTRCLYWEGKLILPFGDQFWFRFLLGWLMPPKVSLLKATQGEAIRNYYHDNHVIQDML
VPLYKVGDALEFVHREMEVYPLWLCPHRLYKLPVKTMVYPEPGFEHQHRQGDTSYAQMFTDVGVYY
APAAVLRGEEFNGVEAVHRLEQWLIENHSYQPQYAVSELNEKDFWRMFDASHYEHCRHKYGAVGTF
MSVYYKSKKGRKTEKEVQEAEAAILEPAYADEA SEQ ID NO: 3 Arabidopsis thaliana Dwarf1 Arath_DWF1 nucleic acid
sequence AK226335
ATGGCGGACGTGCATGAACCTTTGGTGCGCCGCAAGAGGAAGAAGGTTTTGGTGGACTACTTCGTG
CAGTTCCGATGGATCCTCGTGATCTTCGTGGTCCTTCCTATTTCATCTCTGATCTACTTCAATATC
TTTCTGGGCGACATGTGGTCTGCCATGAAGTCAGAGAAGAAGCGCCAGAAGCAACACGATGAGAAT
GTGCAGAAGGTTGTGAAGCGGCTCAAGCAGAGGAACCCAAAGAAGGATGGTCTTGTTTGCACAGCC
AGGAAGCCCTGGATTGCTGTTGGCATGCGCAATGTGGACTACAAGCGTGCGAGGCATTTTGAGGTT

FIGURE 7A

```
GACCTTTCTTCCTTCAGGAACATCCTTGAGATTGACAAAGAGAGGATGGTTGCCAAGGTTGAGCCC
CTTGTAAACATGGGTCAGATAACCAGAGCTACCTGCCCAATGAACTCTTGCCCTTGCAGTCGTCGC
TGAGCTTGACGACCTCACTGTTGGTGGGCTGATCAATGGTTATGGAATTGAGGGGAGCTCTCATCT
CTATGGCCTTTTCTCTGACACGGTTGTTGCAATGGAAGTTGTTCTTGCAGATGGCCGGGTTGTTAG
GGCCACCAAGGATAATGAGTACTCTGACCTTTTCTATGGCATTCCTGGTCCCAGGGAACACTTGG
GTTCCTTGTCTCTGCTGAGATCAAGCTGATTCCCATCAAGGAGTACATGAAGCTCACCTACATTCC
AGTGAAAGGGAGTCTGAAGGAAATCGCGCAGGCCTATGCTGATTCTTTCGCGCCAAGAGATGGTGA
CCCAGCAAAGGTCCCTGACTTTGTTGAAGGAATGGTGTACACAGAAAGCGAGGGTGTCATGATGAC
TGGTGTGTATGCTTCGAAAGAAGAGGCGAAGAAGAAGGGCAACAAGATCAACTGCGTGGGGTGGTG
GTTTAAGCCCTGGTTCTACCAGCATGCTCAGACAGCGCTCAAGAGGGGCGAGTTTGTGGAGTACAT
CCCAACAAGAGAGTACTACCACCGCCACACCCGGTGCCTGTACTGGGAGGGAAAGCTGATCCTGCC
ATTCGGTGACCAGTTCTGGTTCAGGTTCCTGCTGGGTTGGCTCATGCCACCAAAGGTGTCTCTTCT
GAAGGCGACTCAGGGTGAGGCTATCAGGAACTACTACCATGACAACCATGTGATCCAGGACATGCT
GGTGCCGCTGTACAAGGTTGGAGATGCTCTCGAGTTCGTGCACCGCGAGATGGAGGTGTATCCTCT
GTGGCTGTGCCCTCACCGCCTGTACAAGCTGCCCGTGAAGACAATGGTGTACCCTGAGCCTGGGTT
CGAGCACCAGCACAGGCAGGGCGACACAAGCTACGCACAGATGTTCACGGACGTGGGCGTGTACTA
CGCTCCTGCTGCGGTCCTAAGGGGAGAGGAGTTCAATGGCGTGGAGGCGGTGCACAGGCTGGAGCA
GTGGCTGATCGAGAACCACAGCTACCAGCCACAGTACGCGGTGTCGGAGCTGAATGAGAAGGACTT
CTGGCGCATGTTTGACGCGTCCCACTACGAGCACTGCCGGCACAAGTATGGGCGGTGGCACGTT
CATGAGCGTGTACTACAAGTCGAAGAAGGGGCGCAAGACGGAGAAGGAGGTGCAGGAGGCGGAGGC
GGCCATCCTGGAGCCGGCCTACGCGGACGAGGCCTAA
```

SEQ ID NO: 4 Arabidopsis thaliana Dwarf1 Arath_DWF1 translated
polypeptide sequence
```
MSDLQTPLVRPKRKKTWVDYFVKFRWIIVIFIVLPFSATFYFLIYLGDMWSESKSFEKRQKEHDEN
VKKVIKRLKGRDASKDGLVCTARKPWIAVGMRNVDYKRARHFEVDLGEFRNILEINKEKMTARVEP
LVNMGQISRATVPMNLSLAVVAELDDLTVGGLINGYGIEGSSHIYGLFADTVEAYEIVLAGGELVR
ATRDNEYSDLYYAIPWSQGTLGLLVAAEIRLIKVKEYMRLTYIPVKGDLQALAQGYIDSFAPKDGD
KSKIPDFVEGMVYNPTEGVMMVGTYASKEEAKKKGNKINNVGWWFKPWFYQHAQTALKKGQFVEYI
PTREYYHRHTRCLYWEGKLILPFGDQFWFRYLLGWLMPPKVSLLKATQGEAIRNYYHDMHVIQDML
VPLYKVGDALEWVHREMEVYPIWLCPHKLFKQPIKGQIYPEPGFEYENRQGDTEDAQMYTDVGVYY
APGCVLRGEEFDGSEAVRRMEKWLIENHGFQPQYAVSELDEKSFWRMFNGELYEECRKKYRAIGTF
MSVYYKSKKGRKTEKEVREAEQAHLETAYAEAD
```

SEQ ID NO: 5 Brassica rapa Dwarf1 Brara_DWF1 nucleic acid sequence
AC189427
```
ATGTCGGATCTTGAGGCACCACTAGTACGTCCAAAAAGAAAGAAGATATGGGTTGATTACTTCATC
CAGTTCCGATGGATCGTCGTCATCTTCATCGTCCTTCCCATCTCCGCCACATTATACTTCCTCACC
TATCTCGGCGATGTTTGGTCTGAAACAAAATCCTACGAGAAACGTCAAAAAGAACACGACCAAAAC
GTTAACAAAGTCATCAAACGACTCAAGGGAAGGGATGCATCAAAGGACGGGCTTGTTTGCACCGCA
CGTAAACCTTGGATCGCTGTAGGAATGAGAAACGTGGACTACAAGCGAGCCCGACATTTCGAAGTC
GACTTGTCTGCGTTCCGTAACATCCTAAAGATTGACAAAGACAGAATGATTGCTAGAGTGGAGCCT
CTTGTGAACATGGGACAGATTAGCCGTGTTACCGTACCAATGAACCTATCCCTTGCAGTTGTCGCT
GAGCTAGATGATCTCACCGTTGGTGGACTCATCAACGGCTACGGCATTGAAGGAAGCTCTCACGTG
CATGGTTTGTTTACAGACACTGTTGAGGCTTACGAGATTGTTCTAGCTGGTGGGAACTTGTCCGG
GCCACTAGGGACAATGAGTACTCTGACCTATTCTATGCTATTCCATGGTCACAAGGGACACTTGGG
CTTCTTGTTGCTGCCGAGATCAGGCTTGTACACATCAAAGAATACATGAAACTTACTTACATTCCG
GTCAAGGGCGATCTACAAACCATAGCTCAAGGTTATATGGACTCTTTTGCACCTAGAGATCGGGAT
```

FIGURE 7B

CCAGCTAAGATACCAGATTTTGTTGAAGGCATGGTTTATAGTCCAAGTGAAGGTGTAATGATGACA
GGTACATATGCATCGAGAGAAGAGGCTAAGAGGAAAGGGAACAAGATCAATAACGTTGGATGGTGG
TTCAAGCCATGGTTCTACCAATATGCACAAACGGCATTGAAGAAAGGAGAGTTTGTTGAGTACATT
CCAACTCGAGAATATTACCATAGGCACACTAGTTCCTTGTATTGGGAAGGTAAGCTTATCCTTCCG
TTTGGTGACCAGTTCTGGTTTAGGTTCTTGTTTGGATGGTTGATGCCTCCGAAGGTCTCTCTTCTT
AAGGCCACTCAAGGTGAAGCCATCAGAAACTACTACCATGAGATGCATGTCATCCAAGACATGCTT
GTTCCTCTCTACAAAGTCGGTGATGCTCTCAAATGGGTCGACCGTGAAATGGAGGTTTATCCACTT
TGGCTGTGCCCTCACAAACTCTTTAAACAACCGGTTAAAAGCATGATTAACCCTGAACCAGGATTT
GAGTATGAGATGAGACAGGGAGACACAGAAGATGCACAGATGTACACTGACGTTGGAGTCTACTAC
GCTCCTGGTCCTGTCCTGAGAGGCGAAGTGTTCGATGGAGTTGAAGCTGTGCGCAAGATGGAGCAG
TGGCTGATAGAAAACCATGGCTACCAGCCTCAGTATGCAGTATCTGAGCTCGACGAGAGGAGCTTC
TGGAGAATGTTTGACGCTGACTTGTATGAGCATTGCCGCAGGAAGTACAGGGCTGTAGGCACATTC
ATGAGCATTTATTACAAGTCGAAGAAGGGACGTAAGACTGAGAAAGAAGTCAGAGAAGCTGAGCAA
GCTCATCTCGAAACAGCCTATGCCGAGGGAGATTAA

SEQ ID NO: 6 Brassica rapa Dwarf1 Brara_DWF1 translated
polypeptide sequence
MSDLEAPLVRPKRKKIWVDYFIQFRWIVVIFIVLPISATLYFLTYLGDVWSETKSYEKRQKEHDQN
VNKVIKRLKGRDASKDGLVCTARKPWIAVGMRNVDYKRARHFEVDLSAFRNILKIDKDRMIARVEP
LVNMGQISRVTVPMNLSLAVVAELDDLTVGGLINGYGIEGSSHVHGLFTDTVEAYEIVLAGGELVR
ATRDNEYSDLFYAIPWSQGTLGLLVAAEIRLVHIKEYMKLTYIPVKGDLQTIAQGYMDSFAPRDRD
PAKIPDFVEGMVYSPSEGVMMTGTYASREEAKRKGNKINNVGWWFKPWFYQYAQTALKKGEFVEYI
PTREYYHRHTSSLYWEGKLILPFGDQFWFRFLFGWLMPPKVSLLKATQGEAIRNYYHEMHVIQDML
VPLYKVGDALKWVDREMEVYPLWLCPHKLFKQPVKSMINPEPGFEYEMRQGDTEDAQMYTDVGVYY
APGPVLRGEVFDGVEAVRKMEQWLIENHGYQPQYAVSELDERSFWRMFDADLYEHCRRKYRAVGTF
MSIYYKSKKGRKTEKEVREAEQAHLETAYAEGD SEQ ID NO: 7 Glycine max Dwarf1 Glyma_DWF1 nucleic acid sequence
contig of CA783178.1, CA801748.1, CX548424.1
ATGTCAGATCTTGAGGCTCCCTTGCGCCCTAAGAGGAAGAAGGTTTGGGTGGACTATTTCGTTCAG
TTTCGATGGATCCTTGTTATTTTTGTGGTCCTTCCCATCTCCTTCACCATTTATTTCCTTACATAC
CTTGGGGATGTAAGATCTGAGTGGAAGTCCTATAAGACGCGTCAGAAGGAACATGATGAGAATGTG
AAGAAGGTTATCAAACGTCTCAAACAGAGGAATCCATCAAAAGATGGTCTTGTCTGTACCGCTCGT
AAGCCCTGGATTGCTGTTGGATGCGGAACGTTGACTATAAGAGAGCCCGTCATTTTGAAGTTGAT
TTGTCTGCTTTCCGGAATGTACTTGAGATCGACAAAGAACGGATGATTGCAAGAGTTGAGCCCCTA
GTCAACATGGGTCAGATCAGCAGGGTGACTGTACCCATGAATCTTTCCTTGCTGTAGTTGCAGAG
CTTGATGATCTAACTGTCGGTGGTCTCATTAACGGCTATGGTATAGAAGGAAGCTCCCACAAATAT
GGTTTGTTCGCTGATACTGTTGTGGCCTATGAATTATTTTGGCTGATGGCACTCTTGTGAGAGCC
ACCAAGGACAATGAGTACTCTGATCTATACTATGCCATTCCGTGGTCTCAGGGAACACTCGGCCTT
CTTGTTGCTGCTGAGATCAGGCTTATACCCGTTAAGGAGTACATGAAGCTAACCTATAAACCTGTT
GTTGGCACCCTGCAAGATCTTGCTCAGGCATATTGTGATTCTTTTGCTCCCAGAGATGGAGACCAG
GATAATGAGGAGAAGGTTCCAGACTTTGTTAAGGAATGATTTATACACCAACAGAAGGTGTGATG
ATGACAGGAAGATATGCTTCAAAGGAAGAGGCCAAGAAGAAGGGGAATAAGATCAACAGTGTAGGA
TGGTGGTTTAAACCCTGGTTCTATCAGCATGCACAGACGGCACTGAAGAAAGGAGAGTTTGTAGAA
TACATTCCTACCAGAGAATATTATCACAGGCACACGAGATGCTTGTACTGGGAGGGAAAGCTTATC
CTCCCATTTGCTGATCAATTTTGGTTTAGGTATCTGTTTGGCTGGTTGATGCCACCCAAGGTTTCT
CTCCTCAAGGCAACTCAAGGTGATGCTATAAGAAACTATTACCATGAAATGCATGTCATCCAGGAC
ATGCTTGTTCCTTTGTACAAGGTGGGAGATGCTTTAGAATGGGTTCACCGTGAGATGGAGGTATAC

FIGURE 7C

```
CCCATTTGGCTCTGCCCACACAAATTGTTCAAGCTGCCTGTCAAAACTATGATTTACCCCGAGCCA
GGATTCGAACTACACCGCAGGCAAGGAGACACCCAAACTGCTCAAATGTACACAGATGTTGGAGTT
TATTATGCACCAGGTCCTGTTCTTAGGGGTGAGGTATTTGATGGGGCAGAAGCAGTGCGTAAAATG
GAGAACTGGTTGATTGAAAATCATGGTTTTCAGCCACAGTATGCTGTGTCAGAGCTGTCCGAGAAA
AACTTCTGGAGGATGTTTGATGCTGGTTTATATGAGCATACTAGGAGGAAGTATGGAGCTGTTGGG
ACCTTTATGAGTGTATACTACAAATCAAAGAAGGGCAGGAAAACTGAGAAGGAGGTACAAGAAGCA
GAGCAAGCGCACCTTGAAACTGCATATGCAGAAGTTGATCAACCAGTAGACTGA
```

SEQ ID NO: 8 Glycine max Dwarf1 Glyma_DWF1 translated polypeptide sequence
```
MSDLEAPLRPKRKKVWVDYFVQFRWILVIFVVLPISFTIYFLTYLGDVRSEWKSYKTRQKEHDENV
KKVIKRLKQRNPSKDGLVCTARKPWIAVGMRNVDYKRARHFEVDLSAFRNVLEIDKERMIARVEPL
VNMGQISRVTVPMNLSLAVVAELDDLTVGGLINGYGIEGSSHKYGLFADTVVAYEIILADGTLVRA
TKDNEYSDLYYAIPWSQGTLGLLVAAEIRLIPVKEYMKLTYKPVVGTLQDLAQAYCDSFAPRDGDQ
DNEEKVPDFVEGMIYTPTEGVMMTGRYASKEEAKKKGNKINSVGWWFKPWFYQHAQTALKKGEFVE
YIPTREYYHRHTRCLYWEGKLILPFADQFWFRYLFGWLMPPKVSLLKATQGDAIRNYYHEMHVIQD
MLVPLYKVGDALEWVHREMEVYPIWLCPHKLFKLPVKTMIYPEPGFELHRRQGDTQTAQMYTDVGV
YYAPGPVLRGEVFDGAEAVRKMENWLIENHGFQPQYAVSELSEKNFWRMFDAGLYEHTRRKYGAVG
TFMSVYYKSKKGRKTEKEVQEAEQAHLETAYAEVDQPVD
```

SEQ ID NO: 9 Gossypium hirsutum Dwarf1 Goshi_DWF1 nucleic acid sequence AF513859
```
ATGTCAGATCTTCAAGCACCCCTTCGCCCAAAGAGGAAGAAGGGCTTGGTGGACTTTTTGGTCCAG
TTTCGTTGGATTTTTGTTATATTTTTTGTCCTTCCTTTTTCAACTCTGTATTACTTTCTCATATAT
CTTGGAGATGTCAGATCCGAGATGAAGTCCTACAAGCAGCGTCAGAAGGAACATGATGAAAATGTT
TTGAAGGTAGTGAAGCGTCTCAAACAGAGGAATCCAAAAAAGGATGGTCTTGTATGCACAGCCCGT
AAACCATGGATTGCGGTGGGGATGCGGAATGTAGACTATAAGAGAGCTCGCCATTATGAAGTTGAT
TTGTCTGCTTTCCGTAACATTCTTGAAATTGATAAACAGAGAATGATTGCAAGGGTTGAGCCACTT
GTAAACATGGGGCAGATAACACGTGTCACAGTTCCAATGAATCTTTCCTTGCTGTGGTTGCAGAG
CTCGACGATCTTACAGTAGGTGGTCTCATCAATGGCTACGGGATTGAAGGAAGCTCACACATCTAT
GGCCTGTTTTCTGATACTGTTGTAGCTTATGAGATAGTTTTGGCTGATGGCCGTGTTGTTAGAGCT
ACCAAGGACAATGAATATTCTGATCTTTTCTATGCTATCCCATGGTCTCAAGGAACTCTTGGATTT
CTTGTTGCTGCCGAAATCAAGCTTATACCTGTTAAAGAATACATGAGACTGACATACACGCCTGTA
GTGGGGAATTTGCAGGACCTTGCTCAAGGTTATATGGACTCTTTTGCACCCAGAGATGGTGATCAG
GATAATCCAGAGAAAGTTCCCGATTTTGTAGAAGGCATGGTCTACTCACCCACTGAAGGTGTGTTC
ATGACTGGGAGATATGCCTCTAAAGAAGAGGCCAAGAAGAAGGGGAATAAAATTAACAATGTAGGT
TGGTGGTTTAAACCCTGGTTCTACCAACATGCGCAAACGGCCTTAAAGAAGGGAGAGTTTGTAGAG
TACATTCCTACAAGAGAATATTACCACAGGCACACAAGATGTTTGTATTGGGAGGGGAAGCTCATC
CTTCCATTCGGAGATCAATGGTGGTTTAGGTTTCTCTTGGGCTGGTTGATGCCACCCAAGGTTTCC
CTGCTCAAGGCTACTCAAGGTGAATCTATAAGAAACTATTACCATGAGATGCATGTGATTCAAGAC
ATGCTTGTTCCTCTTTACAAGGTTGGGGATGCCCTTGAGTGGGTCCACCATGAGATGGAGATCTAT
CCCATTTGGCTCTGCCCCGCACCGACTGTTCAAGCTTCCTGTCAAGACAATGGTGTATCCTGAACCA
GGCTTTGAGCAGCATCGCAGACAAGGCGACACACCATACGCTCAGATGTTCACCGATGTTGGGGTG
TATTATGCTCCAGGCCCTGTATTGAGGGGTGAAGTATTTGATGGTGCAGAGGCAGTTCGTAAATTG
GAGCAATGGCTGATCAAAAACCACAGTTTCCAGCCACAGTATGCAGTGTCGGAGCTCAACGAGAAG
GATTTCTGGAGGATGTTCGATGCTGACCTGTACGAGCATGTGCGTAGGAAGTACGGAGCTGTGGGA
ACGTTCATGAGTGTGTACTACAAATCCAAGAAAGGAAGGAAGACCGAAAAAGAGGTCCAAGAAGCG
GAACAAGCCCACCTTGAAACTGCGTATGCAGAGGCTGATTAG
```

FIGURE 7D

SEQ ID NO: 10 Gossypium hirsutum Dwarf1 Goshi_DWF1 translated
polypeptide sequence
MSDLQAPLRPKRKKGLVDFLVQFRWIFVIFFVLPFSTLYYFLIYLGDVRSEMKSYKQRQKEHDENV
LKVVKRLKQRNPKKDGLVCTARKPWIAVGMRNVDYKRARHYEVDLSAFRNILEIDKQRMIARVEPL
VNMGQITRVTVPMNLSLAVVAELDDLTVGGLINGYGIEGSSHIYGLFSDTVVAYEIVLADGRVVRA
TKDNEYSDLFYAIPWSQGTLGFLVAAEIKLIPVKEYMRLTYTPVVGNLQDLAQGYMDSFAPRDGDQ
DNPEKVPDFVEGMVYSPTEGVFMTGRYASKEEAKKKGNKINNVGWWFKPWFYQHAQTALKKGEFVE
YIPTREYYHRHTRCLYWEGKLILPFGDQWWFRFLLGWLMPPKVSLLKATQGESIRNYYHEMHVIQD
MLVPLYKVGDALEWVHHEMEIYPIWLCPHRLFKLPVKTMVYPEPGFEQHRRQGDTPYAQMFTDVGV
YYAPGPVLRGEVFDGAEAVRKLEQWLIKNHSFQPQYAVSELNEKDFWRMFDADLYEHVRRKYGAVG
TFMSVYYKSKKGRKTEKEVQEAEQAHLETAYAEAD SEQ ID NO: 11 Lycopersicon esculentum Dwarf1 Lyces_DWF1 nucleic
acid sequence AY584532
ATGACAGATGTTCAGGCTCCCCCCCCTCGTCCTAAGAGGAAGAAAAACATTATGGACCTTCTGTC
CAGTTCAGATGGATTGTTGTTATCTTCGTCGTCCTTCCTCTCTCGTTCTTGTATTATTTCTCCATA
TATCTTGGGGATGTTAGGTCTGAGTGCAAATCATACAAGCAGCGCCAGAAGGAGCATGATGAAAAT
GTTAAAAAGGTTGTGAAGCGTCTTAAGGAGAGGAATGCATCTAAGGATGGTCTTGTCTGCACAGCT
AGGAAGCCCTGGGTTGCTGTTGGAATGAGAAATGTGGACTACAAGCGTGCTCGTCATTTTGAAGTT
GATCTTTCTCCATTTAGAAATGTTCTTAACATTGACACGGAGCGAATGATTGCTAAAGTCGAGCCT
CTAGTCAATATGGGACAAATCTCTAGAGTTACTGTCCCTCTGAATGTTTCCCTTGCAGTTGTTGCT
GAGCTTGATGATCTAACTGTTGGTGGTCTGATCAACGGCTATGGGATTGAAGGAAGTTCTCACATT
TATGGACTGTTCTCAGACACTGTTGTGTCTTATGAAGTTGTTCTAGCAGATGGGCAGGTAGTTAGA
GCTACAAAGGACAATGAATATTCTGATCTTTTCTATGCTATTCCATGGTCTCAAGGGACTCTAGGG
CTTCTGGTTTCAGCTGAGATCAAGCTCATTCCGATCAAGGAATACATGAAACTTACCTACAAACCT
GTAGTTGGTAATTTGAAAGAGATTGCTCAGGCTTATATGGATTCTTTTTCACCTAGAGACGGGGAT
CAGGATAACCATGAGAAAGTTCCAGACTTTGTTGAAACCATGGTGTATACTCCCACAGAAGCTGTT
TGCATGACTGGTAGATATGCTTCAAAAGAAGAGGCCAAGAAGAAGGGCAATGTGATCAACAATGTT
GGTTGGTGGTTCAAAACCTGGTTTTACCAGCACGCTCAAACTGCACTCAAGAAGGGAGAATTCGTA
GAGTACATCCCAACTAGGGAATACTACCACAGGCACACAAGATGCTTGTATTGGGAAGGGAAACTT
ATCCTTCCATTTGGTGATCAATGGTGGTTTAGGTTTCTCTTTGGATGGGCCATGCCTCCCAAGGTT
TCTCTACTTAAAGCCACTCAAGGTGAATACATTAGGAACTATTACCATGAAAACCATGTCATTCAG
GATATGCTTGTTCCTCTCTACAAGGTTGGTGATGCTCTTGAGTGGGTCCACCGTGAGATGGAGGTG
TATCCCCTCTGGCTCTGCCCCCACAGACTCTACAGGCTGCCTCTTAAAACAATGGTGTATCCTGAA
CCAGGTTTTGAGCTGCAGAAGAGGCAGGGTGACACAAAATATGCTCAAATGTACACTGATGTTGGT
GTCTACTATGCTCCTGGACCTATTTTGAGGGGTGAGGTCTTTGATGGTATAGAGGCAGTCCGTAAG
TTGGAGAGTTGGTTGATTGAGAACCATGGATTCCAGCCACAGTATGCTGTCTCTGAGCTGACGGAG
AAGAACTTCTGGAGAATGTTTGATGGAAGCCTATATGAGAACTGCAGGAAAAAGTATAGAGCCATC
GGAACCTTCATGAGTGTGTACTATAAGTCTAAGAAAGGAAAGAAGACAGAGAAGGAGGTGCAGGAA
GCTGAGCAAGAGACTGCTGAAGTTGAGACCCCAGAAGTTGATGAGCCTGAAGATTGA SEQ ID NO: 12 Lycopersicon esculentum Dwarf1 Lyces_DWF1 translated
polypeptide sequence
MTDVQAPPPRPKRKKNIMDLLVQFRWIVVIFVVLPLSFLYYFSIYLGDVRSECKSYKQRQKEHDEN
VKKVVKRLKERNASKDGLVCTARKPWVAVGMRNVDYKRARHFEVDLSPFRNVLNIDTERMIAKVEP
LVNMGQISRVTVPLNVSLAVVAELDDLTVGGLINGYGIEGSSHIYGLFSDTVVSYEVVLADGQVVR
ATKDNEYSDLFYAIPWSQGTLGLLVSAEIKLIPIKEYMKLTYKPVVGNLKEIAQAYMDSFSPRDGD
QDNHEKVPDFVETMVYTPTEAVCMTGRYASKEEAKKKGNVINNVGWWFKTWFYQHAQTALKKGEFV

FIGURE 7E

EYIPTREYYHRHTRCLYWEGKLILPFGDQWWFRFLFGWAMPPKVSLLKATQGEYIRNYYHENHVIQ
DMLVPLYKVGDALEWVHREMEVYPLWLCPHRLYRLPLKTMVYPEPGFELQKRQGDTKYAQMYTDVG
VYYAPGPILRGEVFDGIEAVRKLESWLIENHGFQPQYAVSELTEKNFWRMFDGSLYENCRKKYRAI
GTFMSVYYKSKKGKKTEKEVQEAEQETAEVETPEVDEPED

SEQ ID NO: 13 Oryza sativa Dwarf1 Orysa_DWF1 nucleic acid sequence
Os10g0397400
ATGGCAGATCTGCAGGAGCCCCTCGTTCGTCCGAAGAGGAAGAAGGTTTTGGTGGACTACTTGGTA
AAGTTCCGATGGATTCTGGTGATCTTTGTGGTGCTCCCCATTTCCGCTCTGATCTACTTCAATATC
TATTTGGGCGATGTCTGGTCTGCCATGAAATCTGAGAAACGTCGCCAGAAGGAACATGATGACAAT
GTGCAAAAAGTTGTGAAGCGGCTCAAGCAGAGGAACCCAAAGAAGGATGGCCTTGTTTGCACAGCT
AGGAAGCCCTGGATTGCTGTTGGCATGCGCAATGTAGACTACAAGCGTGCTAGGCATTTTGAGGTT
GACCTTTCCGCCTTCAGGAACATTCTTGAGATTGACAGAGAGAATGGTTGCCAAGGTTGAGCCT
CTTGTCAACATGGGCCAGATAACCAGAGCTACATGCCCAATGAACCTTGCCCTTGCAGTTGTTGCT
GAGCTTGATGACCTTACTGTTGGGGACTGATCAATGGGTATGGTATTGAAGGGAGCTCTCACCTC
TATGGTCTTTTCTCTGACACTGTTGTCGCCGTGGAAGTTGTTCTTGCAGACGGTCGAGTTGTTAGA
GCCACTAAGGATAATGAGTACTCTGACCTTTTCTATGGCATTCCCTGGTCCCAGGGAACACTTGGG
TTTCTTGTTTCCGCTGAGATCAAACTCATTCCCATCAAGGAATACATGAGGCTCACATATACTCCA
GTTAAAGGGTCACTGAAGGAGATAGCACAAGGTTATTGTGATTCGTTTGCACCACGAGATGGTGAT
CCTGCAAAGGTCCCAGACTTCGTTGAGGGAATGGTGTACACAGAAAATGAGGGTGTCATGATGACT
GGTGTTTATGCTTCCAAAGAAGAGGCAAAGAAGAAGGGCAATAAGATCAACTGTGTCGGGTGGTGG
TTCAAGCCTTGGTTTTACCAACATGCTCAGACAGCACTCAAGAAGGGTGAGTTTGTGGAGTACATT
CCAACAAGAGAGTACTACCACCGTCACACCCGGTGTCTGTACTGGGAGGGGAAGCTGATCTTGCCA
TTCGGCGACCAATTCTGGTTCAGGTTCCTCTTGGGCTGGCTGATGCCACCAAAGGTGTCTCTGCTC
AAGGCCACACAGGGTGAATCTATCAGGAATTACTACCATGACAACCATGTGATTCAAGACATGCTG
GTTCCCTTGTACAAAGTTGGAGATGCTCTTGAGTTTGTTCACAAGGAAATGGAGGTTTATCCACTG
TGGCTGTGCCCGCACCGGCTCTACAAGCTCCCTGTGAAAACCATGGTGTACCCAGAGCCTGGCTTT
GAGCACCACCACAGGCAAGGTGACACTAGCTATGCCCAGATGTTCACCGATGTTGGTGTGTACTAT
GCTCCTGGTGCTGTCCTGAGGGGCGAGGAGTTCAATGGCGCTCTAGCTGTCCACAGGCTGGAGCAG
TGGCTGATTGAGAACCACAGCTACCAGCCACAGTACGCTGTATCTGAGCTCAACGAGAAGGACTTC
TGGAGGATGTTTGATGCTTCTCACTACGAGCATTGCCGCCAAAAGTATGGTGCCGTCGGTACCTTT
ATGAGCGTCTACTACAAGTCCAAGAAGGGAAGGAAGACTGAGAAGGAGGTGCAGGAAGCCGAGGCC
GCCATCCTCGAGCCAGCCTACGCTGATGAGGCGTAA SEQ ID NO: 14 Oryza sativa Dwarf1 Orysa_DWF1 translated
polypeptide sequence
MADLQEPLVRPKRKKVLVDYLVKFRWILVIFVVLPISALIYFNIYLGDVWSAMKSEKRRQKEHDDN
VQKVVKRLKQRNPKKDGLVCTARKPWIAVGMRNVDYKRARHFEVDLSAFRNILEIDRERMVAKVEP
LVNMGQITRATCPMNLALAVVAELDDLTVGGLINGYGIEGSSHLYGLFSDTVVAVEVVLADGRVVR
ATKDNEYSDLFYGIPWSQGTLGFLVSAEIKLIPIKEYMRLTYTPVKGSLKEIAQGYCDSFAPRDGD
PAKVPDFVEGMVYTENEGVMMTGVYASKEEAKKKGNKINCVGWWFKPWFYQHAQTALKKGEFVEYI
PTREYYHRHTRCLYWEGKLILPFGDQFWFRFLLGWLMPPKVSLLKATQGESIRNYYHDNHVIQDML
VPLYKVGDALEFVHKEMEVYPLWLCPHRLYKLPVKTMVYPEPGFEHHHRQGDTSYAQMFTDVGVYY
APGAVLRGEEFNGALAVHRLEQWLIENHSYQPQYAVSELNEKDFWRMFDASHYEHCRQKYGAVGTF
MSVYYKSKKGRKTEKEVQEAEAAILEPAYADEA

FIGURE 7F

SEQ ID NO: 15 Pisum sativum Dwarf1 Pissa_DWF1 nucleic acid sequence AF325121
ATGTCTGATCTTGAGGCTCCGCTGCGCCCGAAGAGGAAGAAGATTTGGGTGGACTACTTTGTTAAG
TTTAGATGGATTCTTGTTATTTTTGTGGTTCTTCCCATTTCCTTCACACTTTATTTTCTTACATAC
CTTGGGGATGTGAGATCTGAGTGGAAGTCCTTTAAGACGCGGCAGAAGGAACACGATGAGAATGTC
CAGAAGGTTGTCAATCGCCTCAAAAAGAGGAATCCTTCAAAGGATGGGCTTGTGTGCACTGCTCGT
AAGCCATGGGTTGCTGTTGGGATGAGAAATGTTGACTATAAGAGGGCTCGTCATTTTGAGGTTGAT
CTTTCTCCTTTCAGGAACATTCTTGATATCGACAAAGAGCGGATGATTGCTAGGGTAGAGCCCCTT
GTCAACATGGGGCAGATCACCAGGGTGACTGTGCCTATGAATCTTGCACTCGCTGTGGTTGCTGAG
CTCGATGATCTTACTGTTGGTGGCCTCATAAATGGTTATGGGATCGAAGGAAGTTCCCACAAATAT
GGCCTTTTTTCTGATACTGTTGTAGCCTTTGAAATTATTTTGGCAGATGGATCTCTTGTTAAAGCC
ACCAAGGACAATGAGTACTCTGATCTATTTTATGCTATTCCATGGTCTCAGGGAACACTTGGGCTT
CTTGTTGCTGCTGAGGTCAAGCTTATACCCATTAAGGAGTACATGAAGTTAACTTATAAACCAGTT
GTTGGTAACCTGAAAGATATTGCACAGGCATATTCTGATTCTTTTGCTCCCAGAGACGGTGACCAG
GATAATGATGAGAAGGTTCCAGACTTTGTTGAAACTATGATTTATTCGCCAACACGAGCTGTGTGC
ATGACAGGGAGATATGCTTCAAAGGAAGAGGCCAAGAAAAAGGGGAATAAGATTAACAATGTAGGG
TGGTGGTACAAAACCTGGTTCTACCAACATGCAGAGACAGCACTCAAGAAAGGTCTGTTTGTAGAA
TACATTCCCACCAGAGAGTATTATCACAGGCACACAAGGTGTTTGTATTGGGAGGGAAAGCTTATC
CTCCCATTTGGTGATCAATTTTGGTTTAGATTTCTGTTTGGCTGGTTGATGCCACCCAAGGTTTCT
TTGCTCAAGGCAACTCAAGGGGAAGCTATTAGAAACTATTACCATGAAATGCATGTTATCCAGGAC
ATGCTTGTTCCTCTGTACAAGGTGGGAGATGCACTAGAATGGGTTGACCGTGAGATGGAGGTATAC
CCCATTTGGCTCTGTCCACATAAACTGTTCAAGCTGCCTATCAAAACTATGATTTACCCAGAAGCA
GGCTTTGAGTTGCAACGCAGGCAGGGAGACACACAGAATGCTCAGATGTTCACAGATGTTGGAGTT
TACTATGCACCAGGTCCTGTGTTAAGGGGCGAGGTGTTTGATGGTGCAGAAGCAGTGCGTAAAATG
GAGAGCTGGATGATTGAGAATCATTGTTTTCAGCCACAGTATGCTGTGTCTGAGCTGAATGAGAAA
AACTTCTGGAGGATGTTTGATGCTGGTCTGTATGAGCATTGTAGGAGGAAGTATGGAGCCGTTGGA
ACTTTTATGAGTGTGTACTACAAATGCAAGAAGGGCAGGAAAACTGAGAAGGAAGTGCGTGAAGCC
GAGCAAGCACACCTTGACACTGCGTATGCAGAAGTTGATCAACCAGCAGACTGA SEQ ID NO: 16 Pisum sativum Dwarf1 Pissa_DWF1 translated polypeptide sequence
MSDLEAPLRPKRKKIWVDYFVKFRWILVIFVVLPISFTLYFLTYLGDVRSEWKSFKTRQKEHDENV
QKVVNRLKKRNPSKDGLVCTARKPWVAVGMRNVDYKRARHFEVDLSPFRNILDIDKERMIARVEPL
VNMGQITRVTVPMNLALAVVAELDDLTVGGLINGYGIEGSSHKYGLFSDTVVAFEIILADGSLVKA
TKDNEYSDLFYAIPWSQGTLGLLVAAEVKLIPIKEYMKLTYKPVVGNLKDIAQAYSDSFAPRDGDQ
DNDEKVPDFVETMIYSPTRAVCMTGRYASKEEAKKKGNKINNVGWWYKTWFYQHAETALKKGLFVE
YIPTREYYHRHTRCLYWEGKLILPFGDQFWFRFLFGWLMPPKVSLLKATQGEAIRNYYHEMHVIQD
MLVPLYKVGDALEWVDREMEVYPIWLCPHKLFKLPIKTMIYPEAGFELQRRQGDTQNAQMFTDVGV
YYAPGPVLRGEVFDGAEAVRKMESWMIENHCFQPQYAVSELNEKNFWRMFDAGLYEHCRRKYGAVG
TFMSVYYKCKKGRKTEKEVREAEQAHLDTAYAEVDQPAD SEQ ID NO: 17 Populus tremuloides Dwarf1 Poptr_DWF1 nucleic acid sequence contig of CK091640.1, CK101745.1, CN549251.1, DT491786.1
ATGTCTGATCTCGAGGCCCCCCTGCGCCCAAAGAGGAAGAAGGTGTGGGTAGACTATTTTGTCCAG
TTCAGATGGATCTTAGTTATTTTTGTTGTTCTCCCAATCTCCTTCACCCTTTACTTTCTCACTTAC
CTTGGGGATGTCAAATCAGAGATGAAATCCTACAAACAGCGTCAGAAGGAACATGATGAAAATGTT
AAAAAAGTGGTGAACGCCCTCAAAGAGAGGAATCCATCCAAGGATGGTCTTGTTTGCACTGCTCGT
AAACCCTGGATTGCTGTTGGAATGCGGAATGTTGACTATAAACGGGCTCGGCACTTTGAAGTTGAT

FIGURE 7G

```
TTATCATCTTTCCGTAATATCCTTGAAATTGACAGAGAGAGAATGGTTGCAAGAGTTGAGCCACTT
GTAAATATGGGACAGATTAGCAGGGCGAGTGTCCCAATGAATCTTTCCCTTGCAGTGGTTGCAGAA
CTTGATGATCTCACTGTTGGTGGGCTAATTAATGGTTATGGGATTGAAGGAAGCTCTCACATCTAT
GGCTTGTTCTCTGACACTGTTGTGGCTTATGAGATTGTTTTGGCAGATGGCCAGGTTGTTAGAGCC
ACCAAGGACAATGAATACTCTGATCTTTTCTATGCCATCCCTTGGTCTCAGGGAACACTTGGGCTT
CTTGTCTCTGCTGAGATCAAGCTTATTCCCGTTAAGGAATACATGAGGCTGACCTACAAACCTGTG
GTGGGTAATCTGAAAGAACTTGCACAGGCCTATATAGACTCTTTTGCACCCAGAGATGGAGATCAG
GATAACCCGAGCAAGGTTCCAGACTTTGTGGAGACTATGATTTATAACTCTACCGATGGTGTGATG
ATGACAGGGAGATATGCCTCCAAAGAAGAGGCCAAGAAGAAGGGAAATGTGATTAACAATGTTGGT
TGGTGGTTTAAACCGTGGTTCTATCAGCATGCGCAGACAGCCCTAAAGAAAGGGGAGTTTGTAGAG
TACATTCCAACCAGAGAATATTACCACAGGCACACAAGGTGTTTGTACTGGGAGGGGAAGCTCATA
CTTCCATTTGCTGACCAATGGTGGTTTAGATTTCTCTTAGGCTGGATGATGCCTCCAAAGGTTTCT
CTTCTCAAGGCTACTCAAGGTGAAGCAATCAGAAACTATTACCATGAGATGCATGTCATTCAGGAT
ATGCTTGTTCCTCTTTACAAGGTTGGGGATGCCCTAGAATGGGTCGACCGTGAGATGGAGGTATAT
CCCATTTGGCTTTGTCCGCACAGGTTGTTCAAGCTTCCTGTGAAAACTATGGTGTATCCTGAGCCA
GGGTTTGAGCATCAGCACAGACAGGGAGACACATCCTATGCCCAGATGTACACCGATGTTGGGGTG
TATTATTCACCTGGACCTGTGTTGAGGGGTGAGGTGTTTGAAGGTGCAGATGCAGTTCGTAGAATG
GAGGACTGGTTGATAGAAAACCACGGCTTCCAGCCTCAGTATGCAGTGTCTGAGCTGAATGAGAAG
AAATTCTGGAGGATGTTTGATGCTGACCTCTATGAACACGCCAGGAAGAAATATGGAGCTGTGGGA
ACCTTCATGAGCGTGTACTACAAATCCAAGAAAGGAAGGAAGACGGAGAAGGAGGTGCAGGAAGCA
GAACAAGCCCACCTTGAGACTGCTTATGCTGAGGCTGGTTAG

SEQ ID NO: 18 Populus tremuloides Dwarf1 Poptr_DWF1 translated
polypeptide sequence
MSDLEAPLRPKRKKVWVDYFVQFRWILVIFVVLPISFTLYFLTYLGDVKSEMKSYKQRQKEHDENV
KKVVKRLKERNPSKDGLVCTARKPWIAVGMRNVDYKRARHFEVDLSSFRNILEIDRERMVARVEPL
VNMGQISRASVPMNLSLAVVAELDDLTVGGLINGYGIEGSSHIYGLFSDTVVAYEIVLADGQVVRA
TKDNEYSDLFYAIPWSQGTLGLLVSAEIKLIPVKEYMRLTYKPVVGNLKELAQAYIDSFAPRDGDQ
DNPSKVPDFVETMIYNSTDGVMMTGRYASKEEAKKKGNVINNVGWWFKPWFYQHAQTALKKGEFVE
YIPTREYYHRHTRCLYWEGKLILPFADQWWFRFLLGWMMPPKVSLLKATQGEAIRNYYHEMHVIQD
MLVPLYKVGDALEWVDREMEVYPIWLCPHRLFKLPVKTMVYPEPGFEHQHRQGDTSYAQMYTDVGV
YYSPGPVLRGEVFEGADAVRRMEDWLIENHGFQPQYAVSELNEKKFWRMFDADLYEHARKKYGAVG
TFMSVYYKSKKGRKTEKEVQEAEQAHLETAYAEAG SEQ ID NO: 19 Triticum aestivum Dwarf1 Triae_DWF1 nucleic acid
sequence CK217814
ATGGCGGACCTGCAGACGCCGCTGGTGCGACCAAAGAGGAAGAAGGTTCTGGTGGACTACCTGGTG
CAGTTCCGATGGATCCTCGTCATCTTCGTGGTGCTTCCGGGCTCGGGGCTCATCTACTTCAACATC
TACCTGGGCGACATGTGGTCCGCCATGAAGTCCGAGAAGAAGCGGCAGAAGGAGCACGAGGACAAC
GTGCAGAAGGTCGTGAAGCGGCTCAAGCAGCGCAACCCCAAGAAGGACGGCCTCGTCTGCACGGCC
AGGAAGCCGTGGATCGCCGTCGGCATGCGCAACGTGGACTACAAGCGCGTCAGGCACTTCGAGGTC
GACCTCTCCGCCTTCAGGAACATCCTCGAGATCGACGCCGAGAGGATGGTCGCCAAGGTCGAGCCG
CTCGTCAACATGGGCCAGATATCCAGGGCCACCTGCCCCATGAACCTCTCCCTCGCCGTGGTGGCG
GAGCTCGACGACCTCACCGTCGGCGGCCTCATCAACGGCTACGGCATCGAGGGGAGCTCTCACATC
TACGGGCTCTTCTCCGACACGGTTGTCGCGCTGGAGATCGTCCTGGCTGACGGCCGGGTCGTCCGA
GCCACCAAGGACAACGAGTACTCCGACCTCTTCTACGGCGTGCCCTGGTCGCAGGGAACTCTCGGG
TTCCTTGTCTCAGCCGAGATCAAGCTCATCCCCATCAAGGAGTACATGAGGCTCACCTACACCCCT
GTGAAGGGCCCTCTGAAGGAGGTGGCGCAGGCATACGCCGACGCCGTCGCGCCGAGGGACGGCGAC
```

FIGURE 7H

CCCGCAAAGGTCCCCGACTTCGTGGAAGGGATGGTGTACAGCGCGACGGAGGGCGTGATGATGACC
GGCGTGTACGCGTCCAAGGAGGAGGCCAAGAAGAAGGGCAACAAGATCAACAGCGTGGGGTGGTGG
TTCAAGCCATGGTTCTACCAGCACGCGCAGACGGCGCTCAAGAAGGGCGAGTTCGTGGAGTACATC
CCGACGAGGGAGTACTACCACAGGCACACCCGGTGCCTGTACTGGGAGGGGAAGCTCATCCTGCCC
TTCGGCGACCAGTTCTGGTTCAGGTTCCTCTTCGGCTGGCTGATGCCCCCCAAGGTGTCCCTGCTC
AAGGCCACCCAGGGCGACGCCATCAGGAACTACTACCATGACAACCATGTCATCCAGGACATGCTG
GTGCCCCTGTACAAGGTTGGAGACGCCCTCGAGTTCGTCCACCACGAGATGGAGGTGTACCCGCTG
TGGCTGTGCCCTCACCGGCTGTTCAAGCTGCCGGTGAAGACGATGATCTACCCGGAGCCGGGGTTC
GAGCACCAGCAGCGGCAGGGGGACACGAGCTACGCGCAGATGTTCACGGACGTGGGGGTGTACTAC
ACGCCGGCGTGCATCTTCCGCGGGGAGGAGTTCGACGGGGCGGAGTCGGTGAAGCGGCTGGAGCAG
TGGCTGATCGAGAACCACAGCTACCAGCCGCAGTACGCGGTGACGGAGCTGAACGAGAAGGACTTC
TGGCGCATGTTCGACGCGTCGCACTACGAGCACTGCCGGCACAAGTACGGCGCCGTGGGCACCTTC
ATGAGCGTCTACTACAAGAGCAAGAAGGGGCGCAAGTCCGAGAAGGAGGTGCAGGAGGCCGAGGCC
GCCATCCTGGAGCCCGCCTACGCCGACGAGGCCTAG

SEQ ID NO: 20 Triticum aestivum Dwarf1 Triae_DWF1 translated
polypeptide sequence
MADLQTPLVRPKRKKVLVDYLVQFRWILVIFVVLPGSGLIYFNIYLGDMWSAMKSEKKRQKEHEDN
VQKVVKRLKQRNPKKDGLVCTARKPWIAVGMRNVDYKRVRHFEVDLSAFRNILEIDAERMVAKVEP
LVNMGQISRATCPMNLSLAVVAELDDLTVGGLINGYGIEGSSHIYGLFSDTVVALEIVLADGRVVR
ATKDNEYSDLFYGVPWSQGTLGFLVSAEIKLIPIKEYMRLTYTPVKGPLKEVAQAYADAVAPRDGD
PAKVPDFVEGMVYSATEGVMMTGVYASKEEAKKKGNKINSVGWWFKPWFYQHAQTALKKGEFVEYI
PTREYYHRHTRCLYWEGKLILPFGDQFWFRLFGWLMPPKVSLLKATQGDAIRNYYHDNHVIQDML
VPLYKVGDALEFVHHEMEVYPLWLCPHRLFKLPVKTMIYPEPGFEHQQRQGDTSYAQMFTDVGVYY
TPACIFRGEEFDGAESVKRLEQWLIENHSYQPQYAVTELNEKDFWRMFDASHYEHCRHKYGAVGTF
MSVYYKSKKGRKSEKEVQEAEAAILEPAYADEA SEQ ID NO: 21 Zea mays Dwarf1 Zeama_DWF1 nucleic acid sequence
AY523572
ATGGCGGACGTGCACGAACCTTTGGTGCGCCGTAAGAGGAAGAAGGTTTTGGTGGACTACTTGGTG
AAGTTCCGATGGATCCTCGTGATCTTCGTGGTCCTTCCTATTTCAACTCTGATCTACTTCAACATC
TTCCTGGGCGACATGTGGTCCGCCATGAAGTCGGAGAAGAAGCGCCAGAAGCAGCACGACGAGAAC
GTGCAGAAGGTCGTGAAGCGGCTCAAGCAGAGGAACCCGAAGAAGGACGGTCTTGTTTGCACGGCC
AGGAAGCCCTGGATCGCTGTTGGCATGCGCAACGTGGACTACAAGCGTGCGAGGCATTTCGAGGTC
GACCTTTCTTCCTTCAGGAACATCCTTGAGATCGACAAAGAGAGGATGGTTGCCAAGGTCGAGCCC
CTTGTCAACATGGGTCAGATAACCAGAGCTACCTGCCCAATGAACCTTGCCCTTGCGGTCGTCGCC
GAGCTCGACGACCTCACTGTTGGTGGGCTGATCAACGGTTACGGCATCGAGGGGAGCTCTCACCTC
TATGGCCTTTTCTCCGACACGGTTGTCGCGATGGAGGTTGTTCTCGCAGATGGCCGGGTCGTCAGA
GCCACCAAGGACAACGAGTACTCTGACCTTTTCTATGGAATTCCCTGGTCCCAGGGAACACTGGGG
TTCCTTGTCTCTGCAGAGATCAAGCTGATCCCCATCAAGGAGTACATGAAGCTCACCTACACTCCA
GTCAAGGGGGTCTAAAGGAGATCGCGCAGGCCTACGCGGATTCTTTCGCTCCGAGGGACGGTGAC
CCGGCAAAGGTCCCTGACTTTGTTGAAGGGATGGTGTACACAGAGAGCGAGGGTGTCATGATGACG
GGCGTGTACGCTTCGAAAGAAGAGGCGAAGAAGAAGGGCAACAAGATCAACTGCGTGGGGTGGTGG
TTTAAGCCCTGGTTCTACCAGCACGCTCAGACGGCGCTGAATAGGGGCGAGTTTGTGGAGTACATC
CCGACGAGGGAGTACTACCACCGGCACACCCGGTGCCTGTACTGGGAGGGGAAGCTGATCCTGCCC
TTCGGCGACCAGTTCTGGTTCAGGTTCCTGCTGGGCTGGCTGATGCCACCGAAGGTGTCCCTGCTG
AAGGCGACCCAGGGCGAGGCTATCAGGAACTACTACCACGACAACCATGTGATCCAGGACATGCTG
GTGCCGCTGTACAAGGTTGGGGATGCGCTGGAGTTCGTGCACCGCGAGATGGAGGTGTATCCTCTG

```
TGGCTGTGCCCTCACCGGCTGTACAAGCTGCCGGTGAAGACGATGGTGTACCCGGAGCCTGGGTTC
GAGCACCAGCACAGGCAGGGCGACGCGAGCTACGCACAGATGTTCACGGACGTGGGCGTGTACTAC
GCCCCCGGGGCGGTGCTGAGGGGGGAGGAGTTCAACGGCGCGGAGGCTGTGCACAGGCTGGAGCAG
TGGCTGATCGAGAACCACAGCTACCAGCCGCAGTACGCGGTGTCGGAGCTGAACGAGAAGGACTCC
TGGCGCATGTTCGACGCGTCGCACTACGAGCACTGCCGCCAAAAGTACGGGGCGGTGGGCACGTTC
ATGAGCGTGTACTACAAGTCCAAGAAGGGGCGCAAGACGGAGAAGGAGGTGCAGGAGGCGGAGGCG
GCCATACTGGAGCCGGCCTACGCGGACGAGGAGGCCTAA
```

SEQ ID NO: 22 Zea mays Dwarf1 Zeama_DWF1 translated polypeptide
sequence
```
MADVHEPLVRRKRKKVLVDYLVKFRWILVIFVVLPISTLIYFNIFLGDMWSAMKSEKKRQKQHDEN
VQKVVKRLKQRNPKKDGLVCTARKPWIAVGMRNVDYKRARHFEVDLSSFRNILEIDKERMVAKVEP
LVNMGQITRATCPMNLALAVVAELDDLTVGGLINGYGIEGSSHLYGLFSDTVVAMEVVLADGRVVR
ATKDNEYSDLFYGIPWSQGTLGFLVSAEIKLIPIKEYMKLTYTPVKGGLKEIAQAYADSFAPRDGD
PAKVPDFVEGMVYTESEGVMMTGVYASKEEAKKKGNKINCVGWWFKPWFYQHAQTALNRGEFVEYI
PTREYYHRHTRCLYWEGKLILPFGDQFWFRFLLGWLMPPKVSLLKATQGEAIRNYYHDNHVIQDML
VPLYKVGDALEFVHREMEVYPLWLCPHRLYKLPVKTMVYPEPGFEHQHRQGDASYAQMFTDVGVYY
APGAVLRGEEFNGAEAVHRLEQWLIENHSYQPQYAVSELNEKDSWRMFDASHYEHCRQKYGAVGTF
MSVYYKSKKGRKTEKEVQEAEAAILEPAYADEEA
```

SEQ ID NO: 23 Zinnia elegans Dwarf1 Zinel_DWF1 nucleic acid
sequence AB231156
```
ATGTCTGATCTTGAAGCTCCATTGGTCCGTCCGAAAAGAAAGAAGGTTTGGGTTGACTATTTGTC
CAATTCAGATGGATTATTGTCATTTTTGTTGTACTACCAATCTCCTTCACTCTATACTTCCTCACT
TATCTTGGGGACGTCAGATCAGATTGGAAATCATACAAACAACGCCAAAAGGAACACGAAGAAAAT
GTCAAAAAAGTAGTCAAACGTCTTCAAGAAAGAAACCCATCGAAAGACGGGCGCGTATGTACAGCC
AGAAAACCCTGGATTGCTGTTGGAATGAGAAACGTTGACTACAAACGAGCCCGTCATTTCGAAGTT
GACCTGTCAGCTTTCCGGAACATTCTTGAAATCAATCAAGAAACAATGATTGCAAAATGTGAGCCA
CTGGTCAACATGGGTCGAATCACCCGAGCCACCGTCCCATTGAATCTTGCACTTGCTGCTGTTGCT
GAACTTGATGATCTAACCGTTGGTGGGCTGATCAATGGTTATGGTATTGAGGGTAGTTCTCATCTA
TATGGGCTTTTTTCTGATACTGTTGTGGCTTATGAAATCGTTCTTGCTGGCGGGAAGGTCGTTCGG
GCTACAAAAGATAATGAATACTCTGATCTTTTCTATGCAATTCCATGGTCTCAAGGAACTTTAGGG
CTACTAGTGTCTGCTGAAATCAAACTTATACCAATTAAAGAATACATGAAGTTAACTTACACACCC
GTTAGAGGTAGTGTAAAAGAACTTGGAAAAGCATATATTGACTCATTTGCTCCACGATTCGGGGAA
GAAAACAGTGAAGAAGTTCCTGATTTTGTGGAAGGTATGATTTACAATCCCCATGAAGGTGTTTGT
ATGACAGGAAAATACGCCTCTAAAGAAGAAGCGGAGAAAAAGGAAATAAGATTAATAGTGTGGGG
TGGTGGTTTAAACCATGGTTTTATCAACATGCTCAAACCGCACTTACAAAGGGGAATTTGTTGAG
TACATCCCAACTAGGGAATACTATCATAGGCACACACGGTGTTTGTATTGGGAAGGGAAGCTTATT
CTGCCATTTGGTGATCAATGGTGGTTTAGATTTCTACTTGGGTGGATGATGCCACCAAAGGTTTCT
TTGCTGAAAGCGACACAAGGTGAAGCAATTAGAAATTATTATCATGAAATGCATGTTATTCAAGAT
ATGCTTGTTCCGCTTTACAAAGTTCCTGATGCTTTGGAATGGGTTGATCGTGAGATGGAGGTATAT
CCCCTATGGCTTTGCCCACACCGACTATACAAGCTCCCCTACAAAACAATGGTGTACCCCGAACCA
GGATTTGAGGAACACTGCAGGCAAGGTGACACACCCTATGCTCAAATGTACACAGACGTTGGTGTC
TACTATGCACCAGGACCCGTGTTAAGGGGTGAGGTTTTTGATGGAGTCGATGCAGTTCGTAGAATG
GAAAGTTGGTTAATCGAGAACCACGGGTTCCAGCCACAATACGCAGTTTCTGAACTGAACGAGAAG
AATTTTTGGAGGATGTTTGATGCAGGGCTTTATGAACAGTGTAGGAATAAGTATGGAGCTGTGGGA
ACGTTTATGAGCGTGTATTACAAGTGTAAGAAAGGTAAGAAGACCGAGAAGGAGGTTCAGGAAGCC
GAGCAAGCTCAAGTTGAAGTCCCGTATGCTGAAACTGATTAG
```

FIGURE 7J

SEQ ID NO: 24 Zinnia elegans Dwarf1 Zinel_DWF1 translated polypeptide sequence
MSDLEAPLVRPKRKKVWVDYFVQFRWIIVIFVVLPISFTLYFLTYLGDVRSDWKSYKQRQKEHEEN
VKKVVKRLQERNPSKDGRVCTARKPWIAVGMRNVDYKRARHFEVDLSAFRNILEINQETMIAKCEP
LVNMGRITRATVPLNLALAAVAELDDLTVGGLINGYGIEGSSHLYGLFSDTVVAYEIVLAGGKVVR
ATKDNEYSDLFYAIPWSQGTLGLLVSAEIKLIPIKEYMKLTYTPVRGSVKELGKAYIDSFAPRFGE
ENSEEVPDFVEGMIYNPHEGVCMTGKYASKEEAEKKGNKINSVGWWFKPWFYQHAQTALTKGEFVE
YIPTREYYHRHTRCLYWEGKLILPFGDQWWFRFLLGWMMPPKVSLLKATQGEAIRNYYHEMHVIQD
MLVPLYKVPDALEWVDREMEVYPLWLCPHRLYKLPYKTMVYPEPGFEEHCRQGDTPYAQMYTDVGV
YYAPGPVLRGEVFDGVDAVRRMESWLIENHGFQPQYAVSELNEKNFWRMFDAGLYEQCRNKYGAVG
TFMSVYYKCKKGKKTEKEVQEAEQAQVEVPYAETD SEQ ID NO: 25 Homo sapiens Dwarf1 Homsa_DWF1 nucleic acid sequence
AF261758
ATGGAGCCCGCCGTGTCGCTGGCCGTGTGCGCGCTGCTCTTCCTGCTGTGGGTGCGCCTGAAGGGG
CTGGAGTTCGTGCTCATCCACCAGCGCTGGGTGTTCGTGTGCCTCTTCCTCCTGCCGCTCTCGCTT
ATCTTCGATATCTACTACTACGTGCGCGCCTGGGTGGTGTTCAAGCTCAGCAGCGCTCCGCGCCTG
CACGAGCAGCGCGTGCGGGACATCCAGAAGCAGGTGCGGGAATGGAAGGAGCAGGGTAGCAAGACC
TTCATGTGCACGGGGCGCCCTGGCTGGCTCACTGTCTCACTACGTGTCGGGAAGTACAAGAAGACA
CACAAAAACATCATGATCAACCTGATGGACATTCTGGAAGTGGACACCAAGAAACAGATTGTCCGT
GTGGAGCCCTTGGTGACCATGGGCCAGGTGACTGCCCTGCTGACCTCCATTGGCTGGACTCTCCCC
GTGTTGCCTGAGCTTGATGACCTCACAGTGGGGGGCTTGATCATGGGCACAGGCATCGAGTCATCA
TCCCACAAGTACGGCCTGTTCCAACACATCTGCACTGCTTACGAGCTGGTCCTGGCTGATGGCAGC
TTTGTGCGATGCACTCCGTCCGAAAACTCAGACCTGTTCTATGCCGTACCCTGGTCCTGTGGGACG
CTGGGTTTCCTGGTGGCCGCTGAGATCCGCATCATCCCTGCCAAGAAGTACGTCAAGCTGCGTTTC
GAGCCAGTGCGGGGCCTGGAGGCTATCTGTGCCAAGTTCACCCACGAGTCCCAGCGGCAGGAGAAC
CACTTCGTGGAAGGGCTGCTCTACTCCCTGGATGAGGCTGTCATTATGACAGGGGTCATGACAGAT
GAGGCAGAGCCCAGCAAGCTGAATAGCATTGGCAATTACTACAAGCCGTGGTTCTTTAAGCATGTG
GAGAACTATCTGAAGACAAACCGAGAGGGCCTGGAGTACATTCCCTTGAGACACTACTACCACCGC
CACACGCGCAGCATCTTCTGGGAGCTCCAGGACATCATCCCCTTTGGCAACAACCCCATCTTCCGC
TACCTCTTTGGCTGGATGGTGCCTCCCAAGATCTCCCTCCTGAAGCTGACCCAGGGTGAGACCCTG
CGCAAGCTGTACGAGCAGCACCACGTGGTGCAGGACATGCTGGTGCCCATGAAGTGCCTGCAGCAG
GCCCTGCACACCTTCCAAAACGACATCCACGTCTACCCCATCTGGCTGTGTCCGTTCATCCTGCCC
AGCCAGCCAGGCCTAGTGCACCCCAAAGGAAATGAGGCAGAGCTCTACATCGACATTGGAGCATAT
GGGGAGCCGCGTGTGAAACACTTTGAAGCCAGGTCCTGCATGAGGCAGCTGGAGAAGTTTGTCCGC
AGCGTGCATGGCTTCCAGATGCTGTATGCCGACTGCTACATGAACCGGGAGGAGTTCTGGGAGATG
TTTGATGGCTCCTTGTACCACAAGCTGCGAGAGAAGCTGGGTTGCCAGGACGCCTTCCCCGAGGTG
TACGACAAGATCTGCAAGGCCGCCAGGCACTGA SEQ ID NO: 26 Homo sapiens Dwarf1 Homsa_DWF1 translated polypeptide sequence
MEPAVSLAVCALLFLLWVRLKGLEFVLIHQRWVFVCLFLLPLSLIFDIYYYVRAWVVFKLSSAPRL
HEQRVRDIQKQVREWKEQGSKTFMCTGRPGWLTVSLRVGKYKKTHKNIMINLMDILEVDTKKQIVR
VEPLVTMGQVTALLTSIGWTLPVLPELDDLTVGGLIMGTGIESSSHKYGLFQHICTAYELVLADGS
FVRCTPSENSDLFYAVPWSCGTLGFLVAAEIRIIPAKKYVKLRFEPVRGLEAICAKFTHESQRQEN
HFVEGLLYSLDEAVIMTGVMTDEAEPSKLNSIGNYYKPWFFKHVENYLKTNREGLEYIPLRHYYHR
HTRSIFWELQDIIPFGNNPIFRYLFGWMVPPKISLLKLTQGETLRKLYEQHHVVQDMLVPMKCLQQ
ALHTFQNDIHVYPIWLCPFILPSQPGLVHPKGNEAELYIDIGAYGEPRVKHFEARSCMRQLEKFVR
SVHGFQMLYADCYMNREEFWEMFDGSLYHKLREKLGCQDAFPEVYDKICKAARH

FIGURE 7K

SEQ ID NO: 27 Danio rerio Danre_dhcr24 nucleic acid sequence
NM_001008645
ATGGATCCGTTATTGTATTTGGGAGGGTTAGCTGTGTTGTTTTTGATATGGATCAAAGTGAAAGGC
TTGGAGTACGTGATTATACACCAGAGATGGATCTTCGTGTGCCTGTTTCTCCTGCCCTTGTCCGTC
GTGTTTGATGTGTACTATCACCTGCGCGCCTGGATCATCTTCAAGATGTGCTCCGCGCCCAAACAG
CACGACCAGCGGGTCAGAGACATTCAGAGACAGGTGCGAGAATGGAGGAAAGATGGAGGGAAGAAA
TATATGTGCACGGGACGTCCGGGATGGCTGACTGTGTCCCTCAGAGTGGGAAAATACAAGAAAACT
CACAAGAACATCATGATTAACATGATGGACATCCTGGAGGTTGACACAAAACGAAAGGTAGTGCGT
GTGGAGCCTTTAGCTAACATGGGTCAGGTGACTGCTCTGCTCAACTCTATTGGCTGGACACTGCCG
GTGCTGCCAGAACTCGATGACCTCACTGTTGGCGGGCTGGTGATGGGAACAGGCATTGAGTCTTCA
TCTCACATCTACGGCCTGTTTCAGCACATCTGTGTAGCCTTTGAGCTGGTGTTGGCTGACGGCAGT
CTGGTCCGCTGCACTGAGAAAGAAAACTCTGACCTGTTTTATGCCGTTCCCTGGTCCTGCGGGACT
CTGGGGTTTCTGGTTGCGGCAGAGATCCGGATAATTCCAGCTCAGAAATGGGTGAAGCTGCACTAT
GAACCTGTTCGCGGCTTGGATGCAATTTGCAAAAAGTTTGCTGAGGAATCTGCCAATAAGGAGAAC
CAGTTTGTTGAGGGACTTCAGTACTCTCGGGACGAGGCTGTGATTATGACCGGCGTCATGACGGAT
CATGCAGAGCCTGACAAGACTAACTGTATAGGTTATTATTACAAGCCGTGGTTCTTTCGGCATGTG
GAGAGTTTCCTGAAGCAGAACCGCGTTGCAGTGGAGTACATTCCTCTCCGCCACTATTACCACAGA
CACACCCGCAGCATCTTCTGGGAGTTACAAGACATTATTCCATTCGGGAATAACCCGTTGTTCCGG
TATGTGTTTGGCTGGATGGTTCCTCCAAAGATCTCTCTGCTAAAGCTTACTCAGGGAGAGACCATC
CGCAAACTGTACGAGCAGCACCATGTGGTGCAGGACATGCTGGTCCCCATGAAGGACATCAAGGCT
GCCATCCAGCGTTTCCATGAGGACATTCATGTGTATCCTCTGTGGCTGTGTCCATTCCTTTTGCCC
AACCAGCCAGGAATGGTGCATCCTAAAGGAGATGAAGATGAACTGTATGTTGATATCGGAGCATAT
GGAGAACCAAAGGTCAAACACTTTGAGGCCACATCATCCACACGGCAGCTGGAGAAGTTTGTCAGA
GACGTTCACGGATTCCAGATGTTGTATGCTGATGTATACATGGAACGCAAGGAATTCTGGGAGATG
TTTGACGGCACTTTGTATCACAAACTCAGAGAGGAGCTCGGCTGTAAAGATGCATTCCCTGAAGTC
TTTGACAAAATCTGCAAGTCTGCAAGACATTGA SEQ ID NO: 28 Danio rerio Danre_dhcr24 translated polypeptide
sequence
MDPLLYLGGLAVLFLIWIKVKGLEYVIIHQRWIFVCLFLLPLSVVFDVYYHLRAWIIFKMCSAPKQ
HDQRVRDIQRQVREWRKDGGKKYMCTGRPGWLTVSLRVGKYKKTHKNIMINMMDILEVDTKRKVVR
VEPLANMGQVTALLNSIGWTLPVLPELDDLTVGGLVMGTGIESSSHIYGLFQHICVAFELVLADGS
LVRCTEKENSDLFYAVPWSCGTLGFLVAAEIRIIPAQKWVKLHYEPVRGLDAICKKFAEESANKEN
QFVEGLQYSRDEAVIMTGVMTDHAEPDKTNCIGYYYKPWFFRHVESFLKQNRVAVEYIPLRHYYHR
HTRSIFWELQDIIPFGNNPLFRYVFGWMVPPKISLLKLTQGETIRKLYEQHHVVQDMLVPMKDIKA
AIQRFHEDIHVYPLWLCPFLLPNQPGMVHPKGDEDELYVDIGAYGEPKVKHFEATSSTRQLEKFVR
DVHGFQMLYADVYMERKEFWEMFDGTLYHKLREELGCKDAFPEVFDKICKSARH SEQ ID NO: 29 substrate binding domain of SEQ ID NO: 2
EYMKLTYIPVKGSLKEIAQAYADSFAPRDGDPAKVPDFVEGMVYTESEGVMMTGVYASKEEAKKKG
NKINCVGWWFKPWFYQHAQTALKRGEFVEYIPTREYYHRHTRCLYWEGKLILPFGDQFWFRFLLGW
LMPPKVSLLKATQGEAIRNYYHDNHVIQDMLVPLYKVGDALEFVHREMEVYPLWLCPHRLYKLPVK
TMVYPEPGFEHQHRQGDTSYAQMFTDVGVYYAPAAVLRGEEFNGVEAVHRLEQWLIENHSYQPQYA
VSELNEKDFWRMFDASHYEHCRHKYGAVGTFMSVYYKSKKGRKTEKEVQEAEAAILEPAYADEA SEQ ID NO: 30 prm05930
GGGGACAAGTTTGTACAAAAAAGCAGGCTTCACAATGGCGGACGTGCATGAACC

FIGURE 7L

SEQ ID NO: 31 prm05931
GGGGACCACTTTGTACAAGAAAGCTGGGTTTAGGCCTCGTCCGCGTAGG

SEQ ID NO: 32 Oryza sativa GOS2 promoter
AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAAACTCATCCACCTACT
TTAGTGGCAATCGGGCTAAATAAAAAAGAGTCGCTACACTAGTTTCGTTTTCCTTAGTAATTAAGT
GGGAAAATGAAATCATTATTGCTTAGAATATACGTTCACATCTCTGTCATGAAGTTAAATTATTCG
AGGTAGCCATAATTGTCATCAAACTCTTCTTGAATAAAAAAATCTTTCTAGCTGAACTCAATGGGT
AAAGAGAGAGATTTTTTTTAAAAAAATAGAATGAAGATATTCTGAACGTATTGGCAAAGATTTAAA
CATATAATTATATAATTTTATAGTTTGTGCATTCGTCATATCGCACATCATTAAGGACATGTCTTA
CTCCATCCCAATTTTTATTTAGTAATTAAAGACAATTGACTTATTTTTATTATTTATCTTTTTTCG
ATTAGATGCAAGGTACTTACGCACACACTTTGTGCTCATGTGCATGTGTGAGTGCACCTCCTCAAT
ACACGTTCAACTAGCAACACATCTCTAATATCACTCGCCTATTTAATACATTTAGGTAGCAATATC
TGAATTCAAGCACTCCACCATCACCAGACCACTTTTAATAATATCTAAAATACAAAAAATAATTTT
ACAGAATAGCATGAAAAGTATGAAACGAACTATTTAGGTTTTTCACATACAAAAAAAAAAAGAATT
TTGCTCGTGCGCGAGCGCCAATCTCCCATATTGGGCACACAGGCAACAACAGAGTGGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTCCTCCCATCTATAA
ATTCCTCCCCCCTTTTCCCCTCTCTATATAGGAGGCATCCAAGCCAAGAAGAGGGAGAGCACCAAG
GACACGCGACTAGCAGAAGCCGAGCGACCGCCTTCTTCGATCCATATCTTCCGGTCGAGTTCTTGG
TCGATCTCTTCCCTCCTCCACCTCCTCCTCACAGGGTATGTGCCCTTCGGTTGTTCTTGGATTTAT
TGTTCTAGGTTGTGTAGTACGGGCGTTGATGTTAGGAAAGGGGATCTGTATCTGTGATGATTCCTG
TTCTTGGATTTGGGATAGAGGGGTTCTTGATGTTGCATGTTATCGGTTCGGTTTGATTAGTAGTAT
GGTTTTCAATCGTCTGGAGAGCTCTATGGAAATGAAATGGTTTAGGGTACGGAATCTTGCGATTTT
GTGAGTACCTTTTGTTTGAGGTAAAATCAGAGCACCGGTGATTTTGCTTGGTGTAATAAAAGTACG
GTTGTTTGGTCCTCGATTCTGGTAGTGATGCTTCTCGATTTGACGAAGCTATCCTTTGTTTATTCC
CTATTGAACAAAAATAATCCAACTTTGAAGACGGTCCCGTTGATGAGATTGAATGATTGATTCTTA
AGCCTGTCCAAAATTTCGCAGCTGGCTTGTTTAGATACAGTAGTCCCCATCACGAAATTCATGGAA
ACAGTTATAATCCTCAGGAACAGGGGATTCCCTGTTCTTCCGATTTGCTTTAGTCCCAGAATTTTT
TTTCCCAAATATCTTAAAAAGTCACTTTCTGGTTCAGTTCAATGAATTGATTGCTACAAATAATGC
TTTTATAGCGTTATCCTAGCTGTAGTTCAGTTAATAGGTAATACCCCTATAGTTTAGTCAGGAGAA
GAACTTATCCGATTTCTGATCTCCATTTTTAATTATATGAAATGAACTGTAGCATAAGCAGTATTC
ATTTGGATTATTTTTTTATTAGCTCTCACCCCTTCATTATTCTGAGCTGAAAGTCTGGCATGAAC
TGTCCTCAATTTTGTTTTCAAATTCACATCGATTATCTATGCATTATCCTCTTGTATCTACCTGTA
GAAGTTTCTTTTTGGTTATTCCTTGACTGCTTGATTACAGAAAGAAATTTATGAAGCTGTAATCGG
GATAGTTATACTGCTTGTTCTTATGATTCATTTCCTTTGTGCAGTTCTTGGTGTAGCTTGCCACTT
TCACCAGCAAAGTTC SEQ ID NO: 33 Saccharum officinarum Dwarf1 Sacof_DWF1 nucleic acid
sequence variant
ATGGCGGACGTGCATGAACCTTTGGTGCGCCGCAAGAGGAAGAAGGTTTTGGTGGACTACTTCGTG
CAGTTCCGATGGATCCTCGTGATCTTCGTGGTCCTTCCTATTTCATCTCTGATCTACTTCAATATC
TTTCTGGGCGACATGTGGTCTGCCATGAAGTCAGAGAAGAAGCGCCAGAAGCAACACGATGAGAAT
GTGCAGAAGGTTGTGAAGCGGCTCAAGCAGAGGAACCCAAAGAAGGATGGTCTTGTTTGCACAGCC
AGGAAGCCCTGGATTGCTGTTGGCATGCGCAATGTGGACTACAAGCGTGCGAGGCATTTTGAGGTT
GACCTTTCTTCCTTCAGGAACATCCTTGAGATTGACAAAGAGAGGATGGTTGCCAAGGTTGAGCCC
CTTGTAAACATGGGTCAGATAACCAGAGCTACCTGCCCAATGAACCTTGCCCTTGCAGTCGTCGCT

FIGURE 7M

GAGCTTGACGACCTCACTGTTGGTGGGCTGATCAATGGTTATGGAATTGAGGGGAGCTCTCACCTC
TATGGCCTTTTCTCTGACACGGTTGTTGCAATGGAAGTTGTTCTTGCAGATGGCCGGGTTGTTAGG
GCCACCAAGGATAATGAGTACTCTGACCTTTTCTATGGCATTCCCTGGTCCCAGGGAACACTTGGG
TTCCTTGTCTCTGCTGAGATCAAGCTGATTCCCATCAAGGAGTACATGAAGCTCACCTACATTCCA
GTGAAAGGGAGTCTGAAGGAAATCGCGCAGGCCTATGCTGATTCTTTCGCGCCAAGAGATGGTGAC
CCAGCAAAGGTCCCTGACTTTGTTGAAGGAATGGTGTACACAGAAAGCGAGGGTGTCATGATGACT
GGTGTGTATGCTTCGAAAGAAGAGGCGAAGAAGAAGGGCAACAAGATCAACTGCGTGGGGTGGTGG
TTTAAGCCCTGGTTCTACCAGCATGCTCAGACAGCGCTCAAGAGGGGCGAGTTTGTGGAGTACATC
CCAACAAGAGAGTACTACCACCGCCACACCCGGTGCCTGTACTGGGAGGGAAAGCTGATCCTGCCA
TTCGGTGACCAGTTCTGGTTCAGGTTCCTGCTGGGTTGGCTCATGCCACCAAAGGTGTCTCTTCTG
AAGGCGACTCAGGGTGAGGCTATCAGGAACTACTACCATGACAACCATGTGATCCAGGACATGCTG
GTGCCGCTGTACAAGGTTGGAGATGCTCTCGAGTTCGTGCACCGCGAGATGGAGGTGTATCCTCTG
TGGCTGTGCCCTCACCGCCTGTACAAGCTGCCCGTGAAGACAATGGTGTACCCTGAGCCTGGGTTC
GAGCACCAGCACAGGCAGGGCGACACAAGCTACGCACAGATGTTCACGGACGTGGGCGTGTACTAC
GCTCCTGCTGCGGTCCTAAGGGGAGAGGAGTTCAATGGCGTGGAGGCGGTGCACAGGCTGGAGCAG
TGGCTGATCGAGAACCACAGCTACCAGCCACAGTACGCGGTGTCGGAGCTGAATGAGAAGGACTTC
TGGCACATGTTCGACGCGTCCCACTACGAGCACTGCCGGCACAAGTATGGGGCGGTGGGCACGTTC
ATGAGCGTGTACTACAAGTCGAAGAAGGGGCGCAAGACGGAGAAGGAGGTGCAGGAGGCGGAGGCG
GCCATCCTGGAGCCGGCCTACGCGGACGAGGCCTAA

SEQ ID NO:34 Saccharum officinarum Dwarf1 Sacof_DWF1 translated
polypeptide sequence variant
MADVHEPLVRRKRKKVLVDYFVQFRWILVIFVVLPISSLIYFNIFLGDMWSAMKSEKKRQKQHDEN
VQKVVKRLKQRNPKKDGLVCTARKPWIAVGMRNVDYKRARHFEVDLSSFRNILEIDKERMVAKVEP
LVNMGQITRATCPMNLALAVVAELDDLTVGGLINGYGIEGSSHLYGLFSDTVVAMEVVLADGRVVR
ATKDNEYSDLFYGIPWSQGTLGFLVSAEIKLIPIKEYMKLTYIPVKGSLKEIAQAYADSFAPRDGD
PAKVPDFVEGMVYTESEGVMMTGVYASKEEAKKKGNKINCVGWWFKPWFYQHAQTALKRGEFVEYI
PTREYYHRHTRCLYWEGKLILPFGDQFWFRFLLGWLMPPKVSLLKATQGEAIRNYYHDNHVIQDML
VPLYKVGDALEFVHREMEVYPLWLCPHRLYKLPVKTMVYPEPGFEHQHRQGDTSYAQMFTDVGVYY
APAAVLRGEEFNGVEAVHRLEQWLIENHSYQPQYAVSELNEKDFWHMFDASHYEHCRHKYGAVGTF
MSVYYKSKKGRKTEKEVQEAEAAILEPAYADEA SEQ ID NO: 35 Sorghum bicolor Dwarf1 Sorbi_DWF1 nucleic acid
sequence, contig of CD462169, BI075936.1, AW923039, CN136146.1
ATGGCGGACGTGCATGAACCTTTGGTGCGCCGCAAGAGGAAGAAGGTTTTGGTGGACTACTTGGTG
CAGTTCCGATGGATCCTTGTGATCTTCGTGGTCCTTCCTATTTCATCTCTGATCTACTTCAATATC
TTTCTGGGCGACATGTGGTCTGCCATGAAGTCAGAGAAGAAGCGCCAGAAGCAACACGATGAGAAT
GTGCAGAAGGTTGTGAAGCGGCTCAAGCAGAGGAATCCAAAGAAGGATGGTCTTGTTTGCACAGCC
AGGAAGCCCTGGATTGCTGTTGGCATGCGCAATGTGGACTACAAGCGTGCGAGGCATTTCGAGGTT
GACCTTTCTTCCTTCAGGAACATCCTTGAGATTGACAAAGAGAGGATGGTTGCCAAGGTTGAGCCC
CTTGTAAACATGGGTCAGATAACCAGAGCTACCTGCCCAATGAACCTTGCCCTTGCAGTTGTCGCT
GAGCTTGACGACCTCACTGTTGGTGGGCTGATCAATGGTTATGGAATTGAGGGGAGCTCTCACCTA
TATGGCCTTTTCTCTGACACAGTTGTCGCAATGGAAGTTGTTCTTGCAGATGGCCGGGTCGTTAGA
GCCACCAAGGATAACGAGTACTCTGACCTATTCTATGGCATTCCCTGGTCCCAGGGAACACTTGGG
TTCCTTGTCTCTGCTGAGATCAAGCTGATTCCCATCAAGGAGTACATGAAGCTCACCTACATTCCA
GTGAAGGGGAGTCTGAAGGAAATCGCGCAGGCATATGCTGATTCTTTCGCGCCAAGAGATGGTGAC
CCAGCAAAGGTCCCTGACTTTGTTGAAGGAATGGTGTACACAGAAAGCGAGGGTGTCATGATGACT
GGTGTGTATGCTTCGAAAGAAGAGGCGAAGAAGAAGGGCAACAAGATCAACTGTGTGGGGTGGTGG

FIGURE 7N

```
TTTAAGCCCTGGTTCTACCAGCATGCTCAGACGGCACTTAAGAGGGGCGAGTTTGTGGAGTACGTC
CCAACAAGAGAATACTACCATCGCCACACCCGGTGCCTGTACTGGGAGGGGAAGCTGATCCTGCCA
TTCGGTGACCAGTTCTGGTTCAGGTTCCTGCTGGGTTGGCTCATGCCACCAAAGGTGTCTCTGCTG
AAGGCGACTCAGGGTGAGGCTATCAGGAACTACTACCATGACAACCATGTGATCCAGGACATGCTG
GTGCCACTGTACAAGGTTGGAGATGCTCTTGAGTTTGTGCATCGCGAGATGGAGGTGTATCCTCTG
TGGCTGTGCCCTCACCGCCTGTACAAGCTGCCCGTGAAGACGATGGTGTACCCTGAGCCTGGGTTC
GAGCACCAGCACAGGCAGGGCGACACAAGCTACGCACAGATGTTCACAGATGTGGGCGTGTACTAC
GCCCCTGGTGCAGTCCTAAGGGGAGAGGAGTTCAACGGCGCGGAGGCGGTGCACAGGCTGGAGCAG
TGGCTGATCGAGAACCACAGCTACCAGCCACAGTACGCGGTGTCTGAGCTGAACGAGAAGGACTTC
TGGCGCATGTTTGACGCGTCCCACTACGAGCACTGCCGCCACAAATACGGGGCGGTGGGCACGTTC
ATGAGCGTGTACTACAAGTCGAAGAAGGGGCGCAAGACGGAGAAGGAGGTGCAGGAGGCGGAGGCG
GCCATCCTGGAGCCGGCCTACGCGGACGAGGCCTAA
```

SEQ ID NO: 36 Sorghum bicolor Dwarf1 Sorbi_DWF1 translated polypeptide sequence
```
MADVHEPLVRRKRKKVLVDYLVQFRWILVIFVVLPISSLIYFNIFLGDMWSAMKSEKKRQKQHDEN
VQKVVKRLKQRNPKKDGLVCTARKPWIAVGMRNVDYKRARHFEVDLSSFRNILEIDKERMVAKVEP
LVNMGQITRATCPMNLALAVVAELDDLTVGGLINGYGIEGSSHLYGLFSDTVVAMEVVLADGRVVR
ATKDNEYSDLFYGIPWSQGTLGFLVSAEIKLIPIKEYMKLTYIPVKGSLKEIAQAYADSFAPRDGD
PAKVPDFVEGMVYTESEGVMMTGVYASKEEAKKKGNKINCVGWWFKPWFYQHAQTALKRGEFVEYV
PTREYYHRHTRCLYWEGKLILPFGDQFWFRFLLGWLMPPKVSLLKATQGEAIRNYYHDNHVIQDML
VPLYKVGDALEFVHREMEVYPLWLCPHRLYKLPVKTMVYPEPGFEHQHRQGDTSYAQMFTDVGVYY
APGAVLRGEEFNGAEAVHRLEQWLIENHSYQPQYAVSELNEKDFWRMFDASHYEHCRHKYGAVGTF
MSVYYKSKKGRKTEKEVQEAEAAILEPAYADEA
```

SEQ ID NO: 37 Vitis vinifera Dwarf1 Vitvi_DWF1 nucleic acid sequence AM470510
```
ATGTCGGATCTTCAGGCTCCCTTGCGTCCCAAGAGGAAAAAAATTTGGGTGGACTATTTTGTTCAC
TTCCGATGGATTATTGTCATTTTTGTTGTCCTTCCTATCTCCTTCACTTTGTACTTCCTCACATAT
CTTGGAGATGTCAGATCTGAATCAAATCTTTCAAGCAGCGTCAGGAGGAACATAATGAAAATGTC
AAAAAAGTCATAAAACGTCTCAAAGAGAGGAAYCCATCAAGGGATGGCCTTGTCTGCACAGCCCGG
AAACCATGGATTGCTGTTGGAATGAGAAATGTTGACTATAAGCGGGCTCGGCATTTTGAAGTTGAT
CTTTCAGCTTTCAGAAATATCCTGGACATTGACAAAGAGAGAATGATTGCCAGATGTGAACCCCTA
GTCAACATGGGGCAGATTAGCAGGGTTAGTGTCCCAATGAATCTTGCCCTTGCTGTGGTTGCTGAG
CTTGATGATCTTACAGTTGGTGGCCTCATCAATGGCTATGGAATTGAAGGAAGCTCTCACATTTAT
GGCCTATTCTCTGACACTGTTGTGGCTTATGAAATCATTTTGGCTGATGGGCGGCTAGTTAGAGCT
ACCAAAGACAATGAGTACTCTGATCTTTTCTATGCTATTCCATGGTCTCAGGGAACACTGGGGCTT
CTTGTTGCCGCTGAGATCAAGCTTATACCCATTAAGGAATACATGAAGTTGACTTACAAACCAGTA
GTGGGAAATCTGAAAGACCTTGCRCAGGGTTATTTGGATTCTTTTGCTCCCAGAGACGGAGATCAG
GATAATCMTGAGAAGGTTCCAGACTTTGTAGAAACCATGATTTACAATCCTACTGAAGCTGTGTGT
ATGACAGGGAGATATGCCTCAAAAGAAGAGGCTAAGAAGAAAGGAAATGTGATTAACAGTGTTGGG
TGGTGGTACAAGCCCTGGTTCTATCAACATGCACAGACAGCCCTAAAGAAAGGGGAGTTTGTGGAG
TACATCCCAACCAGGGAATATTACCATAGGCACACTAGGTGTCTGTATTGGGAGGGAAAACTTATT
CTTCCATTTGCAGATCAATGGTGGTTTAGGTTTTTGTTTGGGTGGTTGATGCCACCAAAGGTTTCT
CTCCTCAAGGCTACTCAAGGTGAAGCTATCAGAAACTATTACCATGAGATGCATGTAATTCAGGAC
ATGCTTGTTCCGCTGTACAAGTTGGGGATGCTCTAGAATGGGTACATCATGAGATGGAGGTATAC
CCAATTTGGCTCTGCCCACACCGATTGTACAAGCTTCCTGTCAAAACAATGATATATCCTGAACCA
GGCTTTGAGCTGCATCGCAGACAGGGTGACACACATTATGCCCAGATGTACACAGATGTGGGGGTG
```

FIGURE 70

```
TACTATGCGCCAGGGCCTGTCTTGAGGGGTGAGCAGTTTGATGGTGCAGAAGCAGTTCGCCGAATG
GAGAACTGGTTGATTGAAAACCATGGATTCCAGCCACAATATGCAGTGTCTGAGCTGACTGAAAAG
AACTTCTGGAGGATGTTTGATGCTGGGCTTTATGAGCACTGCAGAAGAAGTATGGAGCAGTGGGG
ACTTTTATGAGTGTTTACTACAAATGCAAGAAGGGGAAGAAGACCGAGAAGGAAGTGCAGGAGGCG
GAGCAAGCACAACTTGAGACACCTTATGCTGAGGCTGATTGA
```

SEQ ID NO: 38 Vitis vinifera Dwarf1 Vitvi_DWF1 translated polypeptide sequence
```
MSDLQAPLRPKRKKIWVDYFVHFRWIIVIFVVLPISFTLYFLTYLGDVRSESKSFKQRQEEHNENV
KKVIKRLKERNPSRDGLVCTARKPWIAVGMRNVDYKRARHFEVDLSAFRNILDIDKERMIARCEPL
VNMGQISRVSVPMNLALAVVAELDDLTVGGLINGYGIEGSSHIYGLFSDTVVAYEIILADGRLVRA
TKDNEYSDLFYAIPWSQGTLGLLVAAEIKLIPIKEYMKLTYKPVVGNLKDLAQGYLDSFAPRDGDQ
DNXEKVPDFVETMIYNPTEAVCMTGRYASKEEAKKKGNVINSVGWWYKPWFYQHAQTALKKGEFVE
YIPTREYYHRHTRCLYWEGKLILPFADQWWFRFLFGWLMPPKVSLLKATQGEAIRNYYHEMHVIQD
MLVPLYKVGDALEWVHHEMEVYPIWLCPHRLYKLPVKTMIYPEPGFELHRRQGDTHYAQMYTDVGV
YYAPGPVLRGEQFDGAEAVRRMENWLIENHGFQPQYAVSELTEKNFWRMFDAGLYEHCRKKYGAVG
TFMSVYYKCKKGKKTEKEVQEAEQAQLETPYAEAD
```

SEQ ID NO: 39 Oryza sativa GOS2 promoter variant
```
AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAAACTCATCCACCTACT
TTAGTGGCAATCGGGCTAAATAAAAAAGAGTCGCTACACTAGTTTCGTTTTCCTTAGTAATTAAGT
GGGAAAATGAAATCATTATTGCTTAGAATATACGTTCACATCTCTGTCATGAAGTTAAATTATTCG
AGGTAGCCATAATTGTCATCAAACTCTTCTTGAATAAAAAAATCTTTCTAGCTGAACTCAATGGGT
AAAGAGAGAGATTTTTTTAAAAAAATAGAATGAAGATATTCTGAACGTATTGGCAAAGATTTAAA
CATATAATTATATAATTTTATAGTTTGTGCATTCGTCATATCGCACATCATTAAGGACATGTCTTA
CTCCATCCCAATTTTTATTTAGTAATTAAAGACAATTGACTTATTTTTATTATTTATCTTTTTTCG
ATTAGATGCAAGGTACTTACGCACACACTTTGTGCTCATGTGCATGTGTGAGTGCACCTCCTCAAT
ACACGTTCAACTAGCAACACATCTCTAATATCACTCGCCTATTTAATACATTTAGGTAGCAATATC
TGAATTCAAGCACTCCACCATCACCAGACCACTTTTAATAATATCTAAAATACAAAAAATAATTTT
ACAGAATAGCATGAAAAGTATGAAACGAACTATTTAGGTTTTTCACATACAAAAAAAAAAGAATT
TTGCTCGTGCGCGAGCGCCAATCTCCCATATTGGGCACACAGGCAACAACAGAGTGGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTTCTCCCATCTATAA
ATTCCTCCCCCCTTTTCCCCTCTCTATATAGGAGGCATCCAAGCCAAGAAGAGGGAGAGCACCAAG
GACACGCGACTAGCAGAAGCCGAGCGACCGCCTTCTCGATCCATATCTTCCGGTCGAGTTCTTGGT
CGATCTCTTCCCTCCTCCACCTCCTCCTCACAGGGTATGTGCCTCCCTTCGGTTGTTCTTGGATTT
ATTGTTCTAGGTTGTGTAGTACGGGCGTTGATGTTAGGAAAGGGGATCTGTATCTGTGATGATTCC
TGTTCTTGGATTTGGGATAGAGGGGTTCTTGATGTTGCATGTTATCGGTTCGGTTTGATTAGTAGT
ATGGTTTTCAATCGTCTGGAGAGCTCTATGGAAATGAAATGGTTTAGGGATCGGAATCTTGCGATT
TTGTGAGTACCTTTTGTTTGAGGTAAAATCAGAGCACCGGTGATTTTGCTTGGTGTAATAAAGTAC
GGTTGTTTGGTCCTCGATTCTGGTAGTGATGCTTCTCGATTTGACGAAGCTATCCTTTGTTTATTC
CCTATTGAACAAAATAATCCAACTTTGAAGACGGTCCCGTTGATGAGATTGAATGATTGATTCTT
AAGCCTGTCCAAAATTTCGCAGCTGGCTTGTTTAGATACAGTAGTCCCCATCACGAAATTCATGGA
AACAGTTATAATCCTCAGGAACAGGGGATTCCCTGTTCTTCCGATTTGCTTTAGTCCCAGAATTTT
TTTTCCCAAATATCTTAAAAAGTCACTTTCTGGTTCAGTTCAATGAATTGATTGCTACAAATAATG
CTTTTATAGCGTTATCCTAGCTGTAGTTCAGTTAATAGGTAATACCCCTATAGTTTAGTCAGGAGA
AGAACTTATCCGATTTCTGATCTCCATTTTTAATTATATGAAATGAACTGTAGCATAAGCAGTATT
```

```
CATTTGGATTATTTTTTTTATTAGCTCTCACCCCTTCATTATTCTGAGCTGAAAGTCTGGCATGAA
CTGTCCTCAATTTTGTTTTCAAATTCACATCGATTATCTATGCATTATCCTCTTGTATCTACCTGT
AGAAGTTTCTTTTTGGTTATTCCTTGACTGCTTGATTACAGAAAGAAATTTATGAAGCTGTAATCG
GGATAGTTATACTGCTTGTTCTTATGATTCATTTCCTTTGTGCAGTTCTTGGTGTAGCTTGCCACT
TTCACCAGCAAAGTTC
```

FIGURE 7Q

SEQUENCE LISTING

```
<160> NUMBER OF SEQ ID NOS: 39

<210> SEQ ID NO 1
<211> LENGTH: 1686
<212> TYPE: DNA
<213> ORGANISM: Saccharum officinarum

<400> SEQUENCE: 1
atggcggacg tgcatgaacc tttggtgcgc cgcaagagga agaaggtttt ggtggactac      60
ttcgtgcagt tccgatggat cctcgtgatc ttcgtggtcc ttcctatttc atctctgatc     120
tacttcaata tcttttctggg cgacatgtgg tctgccatga agtcagagaa gaagcgccag     180
aagcaacacg atgagaatgt gcagaaggtt gtgaagcggc tcaagcagag gaacccaaag     240
```

```
aaggatggtc ttgtttgcac agccaggaag ccctggattg ctgttggcat gcgcaatgtg      300
gactacaagc gtgcgaggca ttttgaggtt gacctttctt ccttcaggaa catccttgag      360
attgacaaag agaggatggt tgccaaggtt gagccccttg taaacatggg tcagataacc      420
agagctacct gcccaatgaa ccttgccctt gcagtcgtcg ctgagcttga cgacctcact      480
gttggtgggc tgatcaatgg ttatggaatt gaggggagct ctcatctcta tggccttttc      540
tctgacacgg ttgttgcaat ggaagttgtt cttgcagatg gccgggttgt tagggccacc      600
aaggataatg agtactctga cctttttctat ggcattccct ggtcccaggg aacacttggg      660
ttccttgtct ctgctgagat caagctgatt cccatcaagg agtacatgaa gctcacctac      720
attccagtga agggagtct gaaggaaatc gcgcaggcct atgctgattc tttcgcgcca      780
agagatggtg acccagcaaa ggtccctgac tttgttgaag aatggtgta cacagaaagc      840 gagggtgtca tgatgactgg tgtgtatgct tcgaaagaag aggcgaagaa gaagggcaac      900
aagatcaact gcgtggggtg gtggtttaag ccctggttct accagcatgc tcagacagcg      960
ctcaagaggg gcgagtttgt ggagtacatc ccaacaagag agtactacca ccgccacacc     1020
cggtgcctgt actgggaggg aaagctgatc ctgccattcg gtgaccagtt ctggttcagg     1080
ttcctgctgg gttggctcat gccaccaaag gtgtctcttc tgaaggcgac tcagggtgag     1140
gctatcagga actactacca tgacaaccat gtgatccagg acatgctggt gccgctgtac     1200
aaggttggag atgctctcga gttcgtgcac cgcgagatgg aggtgtatcc tctgtggctg     1260
tgccctcacc gcctgtacaa gctgcccgtg aagacaatgg tgtaccctga gcctgggttc     1320
gagcaccagc acaggcaggg cgacacaagc tacgcacaga tgttcacgga cgtgggcgtg     1380
tactacgctc ctgctgcggt cctaaggga gaggagttca atggcgtgga ggcggtgcac     1440
aggctggagc agtggctgat cgagaaccac agctaccagc acagtacgc ggtgtcggag     1500 ctgaatgaga aggacttctg cgcatgtttt gacgcgtccc actacgagca ctgccggcac     1560
aagtatgggg cggtgggcac gttcatgagc gtgtactaca agtcgaagaa ggggcgcaag     1620
acggagaagg aggtgcagga ggcggaggcg gccatcctgg agccggccta cgcggacgag     1680
gcctaa                                                                1686
```

<210> SEQ ID NO 2
<211> LENGTH: 561
<212> TYPE: PRT
<213> ORGANISM: Saccharum officinarum

<400> SEQUENCE: 2

```
Met Ala Asp Val His Glu Pro Leu Val Arg Arg Lys Arg Lys Lys Val
1               5                   10                  15

Leu Val Asp Tyr Phe Val Gln Phe Arg Trp Ile Leu Val Ile Phe Val
                20                  25                  30

Val Leu Pro Ile Ser Ser Leu Ile Tyr Phe Asn Ile Phe Leu Gly Asp
            35                  40                  45

Met Trp Ser Ala Met Lys Ser Glu Lys Lys Arg Gln Lys Gln His Asp
        50                  55                  60

Glu Asn Val Gln Lys Val Val Lys Arg Leu Lys Gln Arg Asn Pro Lys
65                  70                  75                  80

Lys Asp Gly Leu Val Cys Thr Ala Arg Lys Pro Trp Ile Ala Val Gly
                85                  90                  95

Met Arg Asn Val Asp Tyr Lys Arg Ala Arg His Phe Glu Val Asp Leu
                100                 105                 110
```

Ser Ser Phe Arg Asn Ile Leu Glu Ile Asp Lys Glu Arg Met Val Ala
    115                 120                 125

Lys Val Glu Pro Leu Val Asn Met Gly Gln Ile Thr Arg Ala Thr Cys
130                 135                 140

Pro Met Asn Leu Ala Leu Ala Val Val Ala Glu Leu Asp Asp Leu Thr
145                 150                 155                 160

Val Gly Gly Leu Ile Asn Gly Tyr Gly Ile Glu Gly Ser Ser His Leu
                165                 170                 175

Tyr Gly Leu Phe Ser Asp Thr Val Val Ala Met Glu Val Val Leu Ala
                180                 185                 190

Asp Gly Arg Val Val Arg Ala Thr Lys Asp Asn Glu Tyr Ser Asp Leu
            195                 200                 205

Phe Tyr Gly Ile Pro Trp Ser Gln Gly Thr Leu Gly Phe Leu Val Ser
    210                 215                 220

Ala Glu Ile Lys Leu Ile Pro Ile Lys Glu Tyr Met Lys Leu Thr Tyr
225                 230                 235                 240

Ile Pro Val Lys Gly Ser Leu Lys Glu Ile Ala Gln Ala Tyr Ala Asp
                245                 250                 255

Ser Phe Ala Pro Arg Asp Gly Asp Pro Ala Lys Val Pro Asp Phe Val
                260                 265                 270

Glu Gly Met Val Tyr Thr Glu Ser Glu Gly Val Met Met Thr Gly Val
            275                 280                 285

Tyr Ala Ser Lys Glu Glu Ala Lys Lys Gly Asn Lys Ile Asn Cys
    290                 295                 300

Val Gly Trp Trp Phe Lys Pro Trp Phe Tyr Gln His Ala Gln Thr Ala
305                 310                 315                 320

Leu Lys Arg Gly Glu Phe Val Glu Tyr Ile Pro Thr Arg Glu Tyr Tyr
                325                 330                 335

His Arg His Thr Arg Cys Leu Tyr Trp Glu Gly Lys Leu Ile Leu Pro
                340                 345                 350

Phe Gly Asp Gln Phe Trp Phe Arg Phe Leu Leu Gly Trp Leu Met Pro
            355                 360                 365

Pro Lys Val Ser Leu Leu Lys Ala Thr Gln Gly Glu Ala Ile Arg Asn
    370                 375                 380

Tyr Tyr His Asp Asn His Val Ile Gln Asp Met Leu Val Pro Leu Tyr
385                 390                 395                 400

Lys Val Gly Asp Ala Leu Glu Phe Val His Arg Glu Met Glu Val Tyr
                405                 410                 415

Pro Leu Trp Leu Cys Pro His Arg Leu Tyr Lys Leu Pro Val Lys Thr
                420                 425                 430

Met Val Tyr Pro Glu Pro Gly Phe Glu His Gln His Arg Gln Gly Asp
            435                 440                 445

Thr Ser Tyr Ala Gln Met Phe Thr Asp Val Gly Val Tyr Tyr Ala Pro
    450                 455                 460

Ala Ala Val Leu Arg Gly Glu Glu Phe Asn Gly Val Glu Ala Val His
465                 470                 475                 480

Arg Leu Glu Gln Trp Leu Ile Glu Asn His Ser Tyr Gln Pro Gln Tyr
                485                 490                 495

Ala Val Ser Glu Leu Asn Glu Lys Asp Phe Trp Arg Met Phe Asp Ala
                500                 505                 510

Ser His Tyr Glu His Cys Arg His Lys Tyr Gly Ala Val Gly Thr Phe
            515                 520                 525

Met Ser Val Tyr Tyr Lys Ser Lys Lys Gly Arg Lys Thr Glu Lys Glu
    530                 535                 540

Val Gln Glu Ala Glu Ala Ala Ile Leu Glu Pro Ala Tyr Ala Asp Glu
545                 550                 555                 560

Ala

<210> SEQ ID NO 3
<211> LENGTH: 1687
<212> TYPE: DNA
<213> ORGANISM: Arabidopsis thaliana

<400> SEQUENCE: 3

| | | | | | |
|---|---|---|---|---|---|
| atggcggacg | tgcatgaacc | tttggtgcgc | cgcaagagga | agaaggtttt | ggtggactac | 60 |
| ttcgtgcagt | ccgatggat | cctcgtgatc | ttcgtggtcc | ttcctatttc | atctctgatc | 120 |
| tacttcaata | tctttctggg | cgacatgtgg | tctgccatga | agtcagagaa | gaagcgccag | 180 |
| aagcaacacg | atgagaatgt | gcagaaggtt | gtgaagcggc | tcaagcagag | gaacccaaag | 240 |
| aaggatggtc | ttgtttgcac | agccaggaag | ccctggattg | ctgttggcat | gcgcaatgtg | 300 |
| gactacaagc | gtgcgaggca | ttttgaggtt | gacctttctt | ccttcaggaa | catccttgag | 360 |
| attgacaaag | agaggatggt | tgccaaggtt | gagccccttg | taaacatggg | tcagataacc | 420 |
| agagctaccct | gcccaatgaa | ctcttgccct | gcagtcgtc | gctgagcttg | acgacctcac | 480 |
| tgttggtggg | ctgatcaatg | gttatggaat | tgaggggagc | tctcatctct | atggcctttt | 540 |
| ctctgacacg | gttgttgcaa | tggaagttgt | tcttgcagat | ggccgggttg | ttagggccac | 600 |
| caaggataat | gagtactctg | acctttctcta | tggcattccc | tggtcccagg | gaacacttgg | 660 |
| gttccttgtc | tctgctgaga | tcaagctgat | tcccatcaag | gagtacatga | agctcaccta | 720 |
| cattccagtg | aaagggagtc | tgaaggaaat | cgcgcaggcc | tatgctgatt | ctttcgcgcc | 780 |
| aagagatggt | gacccagcaa | aggtccctga | ctttgttgaa | ggaatggtgt | acacagaaag | 840 |
| cgagggtgtc | atgatgactg | gtgtgtatgc | ttcgaaagaa | gaggcgaaga | agaagggcaa | 900 |
| caagatcaac | tgcgtggggt | ggtggtttaa | gcccctggttc | taccagcatg | ctcagacagc | 960 |
| gctcaagagg | ggcgagtttg | tggagtacat | cccaacaaga | gagtactacc | accgccacac | 1020 |
| ccggtgcctg | tactgggagg | gaaagctgat | cctgccattc | ggtgaccagt | tctggttcag | 1080 |
| gttcctgctg | ggttggctca | tgccaccaaa | ggtgtctctt | ctgaaggcga | ctcagggtga | 1140 |
| ggctatcagg | aactactacc | atgacaacca | tgtgatccag | gacatgctgg | tgccgctgta | 1200 |
| caaggttgga | gatgctctcg | agttcgtgca | ccgcgagatg | gaggtgtatc | ctctgtggct | 1260 |
| gtgccctcac | cgcctgtaca | agctgcccgt | gaagacaatg | gtgtaccctg | agcctgggtt | 1320 |
| cgagcaccag | cacaggcagg | gcgacacaag | ctacgcacag | atgttcacgg | acgtgggcgt | 1380 |
| gtactacgct | cctgctgcgg | tcctaagggg | agaggagttc | aatggcgtgg | aggcggtgca | 1440 |
| caggctggag | cagtggctga | tcgagaacca | cagctaccag | ccacagtacg | cggtgtcgga | 1500 |
| gctgaatgag | aaggacttct | ggcgcatgtt | tgacgcgtcc | cactacgagc | actgccggca | 1560 |
| caagtatggg | gcggtgggca | cgttcatgag | cgtgtactac | aagtcgaaga | aggggcgcaa | 1620 |
| gacggagaag | gaggtgcagg | aggcggaggc | ggccatcctg | gagccggcct | acgcggacga | 1680 |
| ggcctaa | | | | | | 1687 |

<210> SEQ ID NO 4
<211> LENGTH: 561
<212> TYPE: PRT
<213> ORGANISM: Arabidopsis thaliana

<400> SEQUENCE: 4

-continued

```
Met Ser Asp Leu Gln Thr Pro Leu Val Arg Pro Lys Arg Lys Lys Thr
1               5                   10                  15

Trp Val Asp Tyr Phe Val Lys Phe Arg Trp Ile Ile Val Ile Phe Ile
            20                  25                  30

Val Leu Pro Phe Ser Ala Thr Phe Tyr Phe Leu Ile Tyr Leu Gly Asp
        35                  40                  45

Met Trp Ser Glu Ser Lys Ser Phe Glu Lys Arg Gln Lys Glu His Asp
    50                  55                  60

Glu Asn Val Lys Lys Val Ile Lys Arg Leu Lys Gly Arg Asp Ala Ser
65                  70                  75                  80

Lys Asp Gly Leu Val Cys Thr Ala Arg Lys Pro Trp Ile Ala Val Gly
                85                  90                  95

Met Arg Asn Val Asp Tyr Lys Arg Ala Arg His Phe Glu Val Asp Leu
            100                 105                 110

Gly Glu Phe Arg Asn Ile Leu Glu Ile Asn Lys Glu Lys Met Thr Ala
        115                 120                 125

Arg Val Glu Pro Leu Val Asn Met Gly Gln Ile Ser Arg Ala Thr Val
    130                 135                 140

Pro Met Asn Leu Ser Leu Ala Val Val Ala Glu Leu Asp Asp Leu Thr
145                 150                 155                 160

Val Gly Gly Leu Ile Asn Gly Tyr Gly Ile Glu Gly Ser Ser His Ile
                165                 170                 175

Tyr Gly Leu Phe Ala Asp Thr Val Glu Ala Tyr Glu Ile Val Leu Ala
            180                 185                 190

Gly Gly Glu Leu Val Arg Ala Thr Arg Asp Asn Glu Tyr Ser Asp Leu
        195                 200                 205

Tyr Tyr Ala Ile Pro Trp Ser Gln Gly Thr Leu Gly Leu Leu Val Ala
    210                 215                 220

Ala Glu Ile Arg Leu Ile Lys Val Lys Glu Tyr Met Arg Leu Thr Tyr
225                 230                 235                 240

Ile Pro Val Lys Gly Asp Leu Gln Ala Leu Ala Gln Gly Tyr Ile Asp
                245                 250                 255

Ser Phe Ala Pro Lys Asp Gly Asp Lys Ser Lys Ile Pro Asp Phe Val
            260                 265                 270

Glu Gly Met Val Tyr Asn Pro Thr Glu Gly Val Met Met Val Gly Thr
        275                 280                 285

Tyr Ala Ser Lys Glu Glu Ala Lys Lys Lys Gly Asn Lys Ile Asn Asn
    290                 295                 300

Val Gly Trp Trp Phe Lys Pro Trp Phe Tyr Gln His Ala Gln Thr Ala
305                 310                 315                 320

Leu Lys Lys Gly Gln Phe Val Glu Tyr Ile Pro Thr Arg Glu Tyr Tyr
                325                 330                 335

His Arg His Thr Arg Cys Leu Tyr Trp Glu Gly Lys Leu Ile Leu Pro
            340                 345                 350

Phe Gly Asp Gln Phe Trp Phe Arg Tyr Leu Leu Gly Trp Leu Met Pro
        355                 360                 365

Pro Lys Val Ser Leu Leu Lys Ala Thr Gln Gly Glu Ala Ile Arg Asn
    370                 375                 380

Tyr Tyr His Asp Met His Val Ile Gln Asp Met Leu Val Pro Leu Tyr
385                 390                 395                 400

Lys Val Gly Asp Ala Leu Glu Trp Val His Arg Glu Met Glu Val Tyr
                405                 410                 415

Pro Ile Trp Leu Cys Pro His Lys Leu Phe Lys Gln Pro Ile Lys Gly
            420                 425                 430
```

```
Gln Ile Tyr Pro Glu Pro Gly Phe Glu Tyr Glu Asn Arg Gln Gly Asp
        435                 440                 445

Thr Glu Asp Ala Gln Met Tyr Thr Asp Val Gly Val Tyr Tyr Ala Pro
450                 455                 460

Gly Cys Val Leu Arg Gly Glu Glu Phe Asp Gly Ser Glu Ala Val Arg
465                 470                 475                 480

Arg Met Glu Lys Trp Leu Ile Glu Asn His Gly Phe Gln Pro Gln Tyr
                485                 490                 495

Ala Val Ser Glu Leu Asp Glu Lys Ser Phe Trp Arg Met Phe Asn Gly
                500                 505                 510

Glu Leu Tyr Glu Glu Cys Arg Lys Lys Tyr Arg Ala Ile Gly Thr Phe
        515                 520                 525

Met Ser Val Tyr Tyr Lys Ser Lys Lys Gly Arg Lys Thr Glu Lys Glu
        530                 535                 540

Val Arg Glu Ala Glu Gln Ala His Leu Glu Thr Ala Tyr Ala Glu Ala
545                 550                 555                 560

Asp
```

<210> SEQ ID NO 5
<211> LENGTH: 1686
<212> TYPE: DNA
<213> ORGANISM: Brassica rapa

<400> SEQUENCE: 5

```
atgtcggatc ttgaggcacc actagtacgt ccaaaaagaa agaagatatg ggttgattac    60
ttcatccagt tccgatggat cgtcgtcatc ttcatcgtcc ttcccatctc cgccacatta   120
tacttcctca cctatctcgg cgatgtttgg tctgaaacaa atcctacga gaaacgtcaa   180
aaagaacacg accaaaacgt taacaaagtc atcaaacgac tcaagggaag ggatgcatca   240
aaggacgggc ttgtttgcac cgcacgtaaa ccttggatcg ctgtaggaat gagaaacgtg   300
gactacaagc gagcccgaca tttcgaagtc gacttgtctg cgttccgtaa catcctaaag   360
attgacaaag acagaatgat tgctagagtg gagcctcttg tgaacatggg acagattagc   420
cgtgttaccg taccaatgaa cctatccctt gcagttgtcg ctgagctaga tgatctcacc   480
gttggtggac tcatcaacgg ctacggcatt gaaggaagct ctcacgtgca tggtttgttt   540
acagacactg ttgaggctta cgagattgtt ctagctggtg gggaacttgt ccgggccact   600
agggacaatg agtactctga cctattctat gctattccat ggtcacaagg gacacttggg   660
cttcttgttg ctgccgagat caggcttgta cacatcaaag aatacatgaa acttacttac   720
attccggtca agggcgatct acaaaccata gctcaaggtt atatggactc ttttgcacct   780
agagatcggg atccagctaa gataccagat tttgttgaag gcatggttta tagtccaagt   840
gaaggtgtaa tgatgacagg tacatatgca tcgagagaag aggctaagag gaaagggaac   900
aagatcaata cgttggatg gtggttcaag ccatggttct accaatatgc acaaacggca   960
ttgaagaaag gagagtttgt tgagtacatt ccaactcgag aatattccaa taggcacact  1020
agttccttgt attgggaagg taagcttatc cttccgtttg gtgaccagtt ctggtttagg  1080
ttcttgtttg gatggttgat gcctccgaag gtctctcttc ttaaggccac tcaaggtgaa  1140
gccatcagaa actactacca tgagatgcat gtcatccaag acatgcttgt tcctctctac  1200
aaagtcggtg atgctctcaa atgggtcgac cgtgaaatgg aggtttatcc actttggctg  1260
tgccctcaca aactctttaa acaaccggtt aaaagcatga ttaaccctga ccaggatttt  1320
gagtatgaga tgagacaggg agacacagaa gatgcacaga tgtacactga cgttggagtc  1380
```

-continued

```
tactacgctc ctggtcctgt cctgagaggc gaagtgttcg atggagttga agctgtgcgc    1440
aagatggagc agtggctgat agaaaaccat ggctaccagc ctcagtatgc agtatctgag    1500
ctcgacgaga ggagcttctg gagaatgttt gacgctgact tgtatgagca ttgccgcagg    1560
aagtacaggg ctgtaggcac attcatgagc atttattaca agtcgaagaa gggacgtaag    1620
actgagaaag aagtcagaga agctgagcaa gctcatctcg aaacagccta tgccgaggga    1680
gattaa                                                                1686
```

<210> SEQ ID NO 6
<211> LENGTH: 561
<212> TYPE: PRT
<213> ORGANISM: Brassica rapa

<400> SEQUENCE: 6

| Met | Ser | Asp | Leu | Glu | Ala | Pro | Leu | Val | Arg | Pro | Lys | Arg | Lys | Lys | Ile |
|---|---|---|---|---|---|---|---|---|---|---|---|---|---|---|---|
| 1 | | | | 5 | | | | | 10 | | | | | 15 | |

Trp Val Asp Tyr Phe Ile Gln Phe Arg Trp Ile Val Val Ile Phe Ile
        20                  25                  30

Val Leu Pro Ile Ser Ala Thr Leu Tyr Phe Leu Thr Tyr Leu Gly Asp
    35                  40                  45

Val Trp Ser Glu Thr Lys Ser Tyr Glu Lys Arg Gln Lys Glu His Asp
50                  55                  60

Gln Asn Val Asn Lys Val Ile Lys Arg Leu Lys Gly Arg Asp Ala Ser
65                  70                  75                  80

Lys Asp Gly Leu Val Cys Thr Ala Arg Lys Pro Trp Ile Ala Val Gly
                85                  90                  95

Met Arg Asn Val Asp Tyr Lys Arg Ala Arg His Phe Glu Val Asp Leu
            100                 105                 110

Ser Ala Phe Arg Asn Ile Leu Lys Ile Asp Lys Asp Arg Met Ile Ala
        115                 120                 125

Arg Val Glu Pro Leu Val Asn Met Gly Gln Ile Ser Arg Val Thr Val
    130                 135                 140

Pro Met Asn Leu Ser Leu Ala Val Val Ala Glu Leu Asp Asp Leu Thr
145                 150                 155                 160

Val Gly Gly Leu Ile Asn Gly Tyr Gly Ile Glu Gly Ser Ser His Val
                165                 170                 175

His Gly Leu Phe Thr Asp Thr Val Glu Ala Tyr Glu Ile Val Leu Ala
            180                 185                 190

Gly Gly Glu Leu Val Arg Ala Thr Arg Asp Asn Glu Tyr Ser Asp Leu
        195                 200                 205

Phe Tyr Ala Ile Pro Trp Ser Gln Gly Thr Leu Gly Leu Leu Val Ala
    210                 215                 220

Ala Glu Ile Arg Leu Val His Ile Lys Glu Tyr Met Lys Leu Thr Tyr
225                 230                 235                 240

Ile Pro Val Lys Gly Asp Leu Gln Thr Ile Ala Gln Gly Tyr Met Asp
                245                 250                 255

Ser Phe Ala Pro Arg Asp Arg Asp Pro Ala Lys Ile Pro Asp Phe Val
            260                 265                 270

Glu Gly Met Val Tyr Ser Pro Ser Glu Gly Val Met Met Thr Gly Thr
        275                 280                 285

Tyr Ala Ser Arg Glu Glu Ala Lys Arg Lys Gly Asn Lys Ile Asn Asn
    290                 295                 300

Val Gly Trp Trp Phe Lys Pro Trp Phe Tyr Gln Tyr Ala Gln Thr Ala
305                 310                 315                 320

Leu Lys Lys Gly Glu Phe Val Glu Tyr Ile Pro Thr Arg Tyr Tyr
            325                 330                 335
His Arg His Thr Ser Ser Leu Tyr Trp Glu Gly Lys Leu Ile Leu Pro
            340                 345                 350
Phe Gly Asp Gln Phe Trp Phe Arg Phe Leu Phe Gly Trp Leu Met Pro
            355                 360                 365
Pro Lys Val Ser Leu Leu Lys Ala Thr Gln Gly Glu Ala Ile Arg Asn
370                 375                 380
Tyr Tyr His Glu Met His Val Ile Gln Asp Met Leu Val Pro Leu Tyr
385                 390                 395                 400
Lys Val Gly Asp Ala Leu Lys Trp Val Asp Arg Glu Met Glu Val Tyr
                405                 410                 415
Pro Leu Trp Leu Cys Pro His Lys Leu Phe Lys Gln Pro Val Lys Ser
            420                 425                 430
Met Ile Asn Pro Glu Pro Gly Phe Glu Tyr Glu Met Arg Gln Gly Asp
            435                 440                 445
Thr Glu Asp Ala Gln Met Tyr Thr Asp Val Gly Val Tyr Tyr Ala Pro
    450                 455                 460
Gly Pro Val Leu Arg Gly Glu Val Phe Asp Gly Val Glu Ala Val Arg
465                 470                 475                 480
Lys Met Glu Gln Trp Leu Ile Glu Asn His Gly Tyr Gln Pro Gln Tyr
                485                 490                 495
Ala Val Ser Glu Leu Asp Glu Arg Ser Phe Trp Arg Met Phe Asp Ala
            500                 505                 510
Asp Leu Tyr Glu His Cys Arg Arg Lys Tyr Arg Ala Val Gly Thr Phe
            515                 520                 525
Met Ser Ile Tyr Tyr Lys Ser Lys Lys Gly Arg Lys Thr Glu Lys Glu
    530                 535                 540
Val Arg Glu Ala Glu Gln Ala His Leu Glu Thr Ala Tyr Ala Glu Gly
545                 550                 555                 560
Asp

<210> SEQ ID NO 7
<211> LENGTH: 1704
<212> TYPE: DNA
<213> ORGANISM: Glycine max

<400> SEQUENCE: 7

```
atgtcagatc ttgaggctcc cttgcgccct aagaggaaga aggtttgggt ggactatttc     60
gttcagtttc gatggatcct tgttattttt gtggtccttc ccatctcctt caccatttat    120
ttccttacat accttgggga tgtaagatct gagtggaagt cctataagac gcgtcagaag    180
gaacatgatg agaatgtgaa gaaggttatc aaacgtctca acagaggaa tccatcaaaa     240
gatggtcttg tctgtaccgc tcgtaagccc tggattgctg ttgggatgcg aacgttgac     300
tataagagag cccgtcattt tgaagttgat tgtctgctt tccggaatgt acttgagatc    360
gacaaagaac ggatgattgc aagagttgag cccctagtca acatgggtca gatcagcagg    420
gtgactgtac ccatgaatct ttcccttgct gtagttgcag agcttgatga tctaactgtc    480
ggtggtctca ttaacggcta tggtatagaa ggaagctccc acaaatatgg tttgttcgct    540
gatactgttg tggcctatga aattatttg gctgatggca ctcttgtgag agccaccaag    600
gacaatgagt actctgatct atactatgcc attccgtggt ctcagggaac actcggcctt    660
cttgttgctg ctgagatcag gcttataccc gttaaggagt acatgaagct aacctataaa    720
```

```
cctgttgttg gcaccctgca agatcttgct caggcatatt gtgattcttt tgctcccaga      780
gatggagacc aggataatga ggagaaggtt ccagactttg ttgaaggaat gatttataca      840
ccaacagaag gtgtgatgat gacaggaaga tatgcttcaa aggaagaggc caagaagaag      900
gggaataaga tcaacagtgt aggatggtgg tttaaaccct ggttctatca gcatgcacag      960
acggcactga agaaggaga gtttgtagaa tacattccta ccagagaata ttatcacagg     1020
cacacgagat gcttgtactg ggagggaaag cttatcctcc catttgctga tcaattttgg     1080
tttaggtatc tgtttggctg gttgatgcca cccaaggttt ctctcctcaa ggcaactcaa     1140
ggtgatgcta taagaaacta ttaccatgaa atgcatgtca tccaggacat gcttgttcct     1200
ttgtacaagg tgggagatgc tttagaatgg gttcaccgtg agatggaggt atacccattt     1260
tggctctgcc cacacaaatt gttcaagctg cctgtcaaaa ctatgattta ccccgagcca     1320
ggattcgaac tacaccgcag gcaaggagac acccaaactg ctcaaatgta cacagatgtt     1380
ggagtttatt atgcaccagg tcctgttctt aggggtgagg tatttgatgg ggcagaagca     1440
gtgcgtaaaa tggagaactg gttgattgaa aatcatggtt ttcagccaca gtatgctgtg     1500
tcagagctgt ccgagaaaaa cttctggagg atgtttgatg ctggtttata tgagcatact     1560
aggaggaagt atggagctgt tgggaccttt atgagtgtat actacaaatc aaagaagggc     1620
aggaaaactg agaaggaggt acaagaagca gagcaagcgc accttgaaac tgcatatgca     1680
gaagttgatc aaccagtaga ctga                                             1704

<210> SEQ ID NO 8
<211> LENGTH: 567
<212> TYPE: PRT
<213> ORGANISM: Glycine max

<400> SEQUENCE: 8

Met Ser Asp Leu Glu Ala Pro Leu Arg Pro Lys Arg Lys Lys Val Trp
1               5                   10                  15

Val Asp Tyr Phe Val Gln Phe Arg Trp Ile Leu Val Ile Phe Val Val
                20                  25                  30

Leu Pro Ile Ser Phe Thr Ile Tyr Phe Leu Thr Tyr Leu Gly Asp Val
            35                  40                  45

Arg Ser Glu Trp Lys Ser Tyr Lys Thr Arg Gln Lys Glu His Asp Glu
        50                  55                  60

Asn Val Lys Lys Val Ile Lys Arg Leu Lys Gln Arg Asn Pro Ser Lys
65                  70                  75                  80

Asp Gly Leu Val Cys Thr Ala Arg Lys Pro Trp Ile Ala Val Gly Met
                85                  90                  95

Arg Asn Val Asp Tyr Lys Arg Ala Arg His Phe Glu Val Asp Leu Ser
                100                 105                 110

Ala Phe Arg Asn Val Leu Glu Ile Asp Lys Glu Arg Met Ile Ala Arg
            115                 120                 125

Val Glu Pro Leu Val Asn Met Gly Gln Ile Ser Arg Val Thr Val Pro
        130                 135                 140

Met Asn Leu Ser Leu Ala Val Val Ala Glu Leu Asp Asp Leu Thr Val
145                 150                 155                 160

Gly Gly Leu Ile Asn Gly Tyr Gly Ile Glu Gly Ser Ser His Lys Tyr
                165                 170                 175

Gly Leu Phe Ala Asp Thr Val Val Ala Tyr Glu Ile Ile Leu Ala Asp
                180                 185                 190

Gly Thr Leu Val Arg Ala Thr Lys Asp Asn Glu Tyr Ser Asp Leu Tyr
            195                 200                 205
```

Tyr Ala Ile Pro Trp Ser Gln Gly Thr Leu Gly Leu Val Ala Ala
    210                 215                 220

Glu Ile Arg Leu Ile Pro Val Lys Glu Tyr Met Lys Leu Thr Tyr Lys
225                 230                 235                 240

Pro Val Val Gly Thr Leu Gln Asp Leu Ala Gln Ala Tyr Cys Asp Ser
                245                 250                 255

Phe Ala Pro Arg Asp Gly Asp Gln Asp Asn Glu Glu Lys Val Pro Asp
            260                 265                 270

Phe Val Glu Gly Met Ile Tyr Thr Pro Thr Glu Gly Val Met Met Thr
        275                 280                 285

Gly Arg Tyr Ala Ser Lys Glu Glu Ala Lys Lys Gly Asn Lys Ile
    290                 295                 300

Asn Ser Val Gly Trp Trp Phe Lys Pro Trp Phe Tyr Gln His Ala Gln
305                 310                 315                 320

Thr Ala Leu Lys Lys Gly Glu Phe Val Glu Tyr Ile Pro Thr Arg Glu
                325                 330                 335

Tyr Tyr His Arg His Thr Arg Cys Leu Tyr Trp Gly Lys Leu Ile
            340                 345                 350

Leu Pro Phe Ala Asp Gln Phe Trp Phe Arg Tyr Leu Phe Gly Trp Leu
        355                 360                 365

Met Pro Pro Lys Val Ser Leu Leu Lys Ala Thr Gln Gly Asp Ala Ile
    370                 375                 380

Arg Asn Tyr Tyr His Glu Met His Val Ile Gln Asp Met Leu Val Pro
385                 390                 395                 400

Leu Tyr Lys Val Gly Asp Ala Leu Glu Trp Val His Arg Glu Met Glu
                405                 410                 415

Val Tyr Pro Ile Trp Leu Cys Pro His Lys Leu Phe Lys Leu Pro Val
            420                 425                 430

Lys Thr Met Ile Tyr Pro Glu Pro Gly Phe Glu Leu His Arg Arg Gln
        435                 440                 445

Gly Asp Thr Gln Thr Ala Gln Met Tyr Thr Asp Val Gly Val Tyr Tyr
    450                 455                 460

Ala Pro Gly Pro Val Leu Arg Gly Glu Val Phe Asp Gly Ala Glu Ala
465                 470                 475                 480

Val Arg Lys Met Glu Asn Trp Leu Ile Glu Asn His Gly Phe Gln Pro
                485                 490                 495

Gln Tyr Ala Val Ser Glu Leu Ser Glu Lys Asn Phe Trp Arg Met Phe
            500                 505                 510

Asp Ala Gly Leu Tyr Glu His Thr Arg Arg Lys Tyr Gly Ala Val Gly
        515                 520                 525

Thr Phe Met Ser Val Tyr Tyr Lys Ser Lys Gly Arg Lys Thr Glu
    530                 535                 540

Lys Glu Val Gln Glu Ala Glu Gln Ala His Leu Glu Thr Ala Tyr Ala
545                 550                 555                 560

Glu Val Asp Gln Pro Val Asp
                565

<210> SEQ ID NO 9
<211> LENGTH: 1692
<212> TYPE: DNA
<213> ORGANISM: Gossypium hirsutum

<400> SEQUENCE: 9
atgtcagatc ttcaagcacc ccttcgccca agaggaaga agggcttggt ggacttttg      60

```
gtccagtttc gttggatttt tgttatattt tttgtccttc cttttcaac tctgtattac    120
tttctcatat atcttggaga tgtcagatcc gagatgaagt cctacaagca gcgtcagaag    180
gaacatgatg aaaatgtttt gaaggtagtg aagcgtctca acagaggaa tccaaaaag     240
gatggtcttg tatgcacagc ccgtaaacca tggattgcgg tggggatgcg aatgtagac    300
tataagagag ctcgccatta tgaagttgat tgtctgctt ccgtaacat tcttgaaatt     360
gataaacaga gaatgattgc aagggttgag ccacttgtaa acatggggca gataacacgt    420
gtcacagttc caatgaatct ttcccttgct gtggttgcag agctcgacga tcttacagta    480
ggtggtctca tcaatggcta cgggattgaa ggaagctcac acatctatgg cctgttttct    540
gatactgttg tagcttatga gatagttttg gctgatggcc gtgttgttag agctaccaag    600
gacaatgaat attctgatct tttctatgct atcccatggt ctcaaggaac tcttggattt    660
cttgttgctg ccgaaatcaa gcttatacct gttaaagaat acatgagact gacatacacg    720
cctgtagtgg ggaatttgca ggaccttgct caaggttata tggactcttt tgcacccaga    780
gatggtgatc aggataatcc agagaaagtt cccgattttg tagaaggcat ggtctactca    840
cccactgaag gtgtgttcat gactgggaga tatgcctcta agaagaggc caagaagaag    900
gggaataaaa ttaacaatgt aggttggtgg tttaaacct ggttctacca acatgcgcaa     960
acggccttaa agaagggaga gtttgtagag tacattccta caagagaata ttaccacagg   1020
cacacaagat gtttgtattg ggaggggaag ctcatccttc cattcggaga tcaatggtgg   1080
tttaggtttc tcttgggctg gttgatgcca cccaaggttt ccctgctcaa ggctactcaa   1140
ggtgaatcta taagaaacta ttaccatgag atgcatgtga ttcaagacat gcttgttcct   1200
cttacaagg ttggggatgc ccttgagtgg gtccaccatg agatggagat ctatcccatt    1260
tggctctgcc cgcaccgact gttcaagctt cctgtcaaga caatggtgta tcctgaacca   1320
ggctttgagc agcatcgcag acaaggcgac acaccatacg ctcagatgtt caccgatgtt   1380
ggggtgtatt atgctccagg ccctgtattg aggggtgaag tatttgatgg tgcagaggca   1440
gttcgtaaat tggagcaatg gctgatcaaa accacagtt tccagccaca gtatgcagtg    1500
tcggagctca cgagaagga tttctggagg atgttcgatg ctgacctgta cgagcatgtg    1560
cgtaggaagt acggagctgt gggaacgttc atgagtgtgt actacaaatc caagaaagga   1620
aggaagaccg aaaagaggt ccaagaagcg aacaagccc accttgaaac tgcgtatgca     1680
gaggctgatt ag                                                       1692
```

<210> SEQ ID NO 10
<211> LENGTH: 563
<212> TYPE: PRT
<213> ORGANISM: Gossypium hirsutum

<400> SEQUENCE: 10

```
Met Ser Asp Leu Gln Ala Pro Leu Arg Pro Lys Arg Lys Lys Gly Leu
1               5                   10                  15

Val Asp Phe Leu Val Gln Phe Arg Trp Ile Phe Val Ile Phe Phe Val
                20                  25                  30

Leu Pro Phe Ser Thr Leu Tyr Tyr Phe Leu Ile Tyr Leu Gly Asp Val
                35                  40                  45

Arg Ser Glu Met Lys Ser Tyr Lys Gln Arg Gln Lys Glu His Asp Glu
            50                  55                  60

Asn Val Leu Lys Val Val Lys Arg Leu Lys Gln Arg Asn Pro Lys Lys
65                  70                  75                  80

Asp Gly Leu Val Cys Thr Ala Arg Lys Pro Trp Ile Ala Val Gly Met
```

```
                    85                  90                  95
Arg Asn Val Asp Tyr Lys Arg Ala Arg His Tyr Glu Val Asp Leu Ser
                100                 105                 110

Ala Phe Arg Asn Ile Leu Glu Ile Asp Lys Gln Arg Met Ile Ala Arg
            115                 120                 125

Val Glu Pro Leu Val Asn Met Gly Gln Ile Thr Arg Val Thr Val Pro
        130                 135                 140

Met Asn Leu Ser Leu Ala Val Val Ala Glu Leu Asp Asp Leu Thr Val
145                 150                 155                 160

Gly Gly Leu Ile Asn Gly Tyr Gly Ile Glu Gly Ser Ser His Ile Tyr
                165                 170                 175

Gly Leu Phe Ser Asp Thr Val Ala Tyr Glu Ile Val Leu Ala Asp
            180                 185                 190

Gly Arg Val Val Arg Ala Thr Lys Asp Asn Glu Tyr Ser Asp Leu Phe
        195                 200                 205

Tyr Ala Ile Pro Trp Ser Gln Gly Thr Leu Gly Phe Leu Val Ala Ala
210                 215                 220

Glu Ile Lys Leu Ile Pro Val Lys Glu Tyr Met Arg Leu Thr Tyr Thr
225                 230                 235                 240

Pro Val Val Gly Asn Leu Gln Asp Leu Ala Gln Gly Tyr Met Asp Ser
                245                 250                 255

Phe Ala Pro Arg Asp Gly Asp Gln Asp Asn Pro Glu Lys Val Pro Asp
            260                 265                 270

Phe Val Glu Gly Met Val Tyr Ser Pro Thr Gly Val Phe Met Thr
        275                 280                 285

Gly Arg Tyr Ala Ser Lys Glu Glu Ala Lys Lys Gly Asn Lys Ile
290                 295                 300

Asn Asn Val Gly Trp Trp Phe Lys Pro Trp Phe Tyr Gln His Ala Gln
305                 310                 315                 320

Thr Ala Leu Lys Lys Gly Glu Phe Val Glu Tyr Ile Pro Thr Arg Glu
                325                 330                 335

Tyr Tyr His Arg His Thr Arg Cys Leu Tyr Trp Glu Gly Lys Leu Ile
            340                 345                 350

Leu Pro Phe Gly Asp Gln Trp Trp Phe Arg Phe Leu Leu Gly Trp Leu
        355                 360                 365

Met Pro Pro Lys Val Ser Leu Leu Lys Ala Thr Gln Gly Glu Ser Ile
370                 375                 380

Arg Asn Tyr Tyr His Glu Met His Val Ile Gln Asp Met Leu Val Pro
385                 390                 395                 400

Leu Tyr Lys Val Gly Asp Ala Leu Glu Trp Val His His Glu Met Glu
                405                 410                 415

Ile Tyr Pro Ile Trp Leu Cys Pro His Arg Leu Phe Lys Leu Pro Val
            420                 425                 430

Lys Thr Met Val Tyr Pro Glu Pro Gly Phe Glu Gln His Arg Arg Gln
        435                 440                 445

Gly Asp Thr Pro Tyr Ala Gln Met Phe Thr Asp Val Gly Val Tyr Tyr
450                 455                 460

Ala Pro Gly Pro Val Leu Arg Gly Glu Val Phe Asp Gly Ala Glu Ala
465                 470                 475                 480

Val Arg Lys Leu Glu Gln Trp Leu Ile Lys Asn His Ser Phe Gln Pro
                485                 490                 495

Gln Tyr Ala Val Ser Glu Leu Asn Glu Lys Asp Phe Trp Arg Met Phe
            500                 505                 510
```

```
Asp Ala Asp Leu Tyr Glu His Val Arg Arg Lys Tyr Gly Ala Val Gly
        515                 520                 525

Thr Phe Met Ser Val Tyr Tyr Lys Ser Lys Lys Gly Arg Lys Thr Glu
    530                 535                 540

Lys Glu Val Gln Glu Ala Glu Gln Ala His Leu Glu Thr Ala Tyr Ala
545                 550                 555                 560

Glu Ala Asp

<210> SEQ ID NO 11
<211> LENGTH: 1707
<212> TYPE: DNA
<213> ORGANISM: Lycopersicon esculentum

<400> SEQUENCE: 11
```

| | | | | |
|---|---|---|---|---|
| atgacagatg | ttcaggctcc | cccccctcgt | cctaagagga | agaaaaacat tatggacctt | 60 |
| cttgtccagt | tcagatggat | tgttgttatc | ttcgtcgtcc | ttcctctctc gttcttgtat | 120 |
| tatttctcca | tatatcttgg | ggatgttagg | tctgagtgca | atcatacaa gcagcgccag | 180 |
| aaggagcatg | atgaaaatgt | taaaaaggtt | gtgaagcgtc | ttaaggagag gaatgcatct | 240 |
| aaggatggtc | ttgtctgcac | agctaggaag | ccctgggttg | ctgttggaat gagaaatgtg | 300 |
| gactacaagc | gtgctcgtca | ttttgaagtt | gatctttctc | catttagaaa tgttcttaac | 360 |
| attgacacgg | agcgaatgat | tgctaaagtc | gagcctctag | tcaatatggg acaaatctct | 420 |
| agagttactg | tccctctgaa | tgttcccctt | gcagttgttg | ctgagcttga tgatctaact | 480 |
| gttggtggtc | tgatcaacgg | ctatgggatt | gaaggaagtt | ctcacattta tggactgttc | 540 |
| tcagacactg | ttgtgtctta | tgaagttgtt | ctagcagatg | ggcaggtagt tagagctaca | 600 |
| aaggacaatg | aatattctga | tcttttctat | gctattccat | ggtctcaagg gactctaggg | 660 |
| cttctggttt | cagctgagat | caagctcatt | ccgatcaagg | aatacatgaa acttacctac | 720 |
| aaacctgtag | ttggtaattt | gaaagagatt | gctcaggctt | atatggattc tttttcacct | 780 |
| agagacgggg | atcaggataa | ccatgagaaa | gttccagact | tgttgaaaac catggtgtat | 840 |
| actcccacag | aagctgtttg | catgactggt | agatatgctt | caaaagaaga ggccaagaag | 900 |
| aagggcaatg | tgatcaacaa | tgttggttgg | tggttcaaaa | cctggtttta ccagcacgct | 960 |
| caaactgcac | tcaagaaggg | agaattcgta | gagtacatcc | aactaggga atactaccac | 1020 |
| aggcacacaa | gatgcttgta | tgggaaggg | aaacttatcc | ttccatttgg tgatcaatgg | 1080 |
| tggtttaggt | ttctcttgg | atgggccatg | cctcccaagg | tttctctact aaagccact | 1140 |
| caaggtgaat | acattaggaa | ctattaccat | gaaaaccatg | tcattcagga tatgcttgtt | 1200 |
| cctctctaca | aggttggtga | tgctcttgag | tgggtccacc | gtgagatgga ggtgtatccc | 1260 |
| ctctggctct | gccccacag | actctacagg | ctgcctctta | aaacaatggt gtatcctgaa | 1320 |
| ccaggttttg | agctgcagaa | gaggcagggt | gacacaaaat | atgctcaaat gtacactgat | 1380 |
| gttggtgtct | actatgctcc | tggacctatt | ttgaggggtg | aggtctttga tggtatagag | 1440 |
| gcagtccgta | agttggagag | ttggttgatt | gagaaccatg | gattccagcc acagtatgct | 1500 |
| gtctctgagc | tgacggagaa | gaacttctgg | agaatgtttg | atggaagcct atatgagaac | 1560 |
| tgcaggaaaa | agtatagagc | catcggaacc | ttcatgagtg | tgtactataa gtctaagaaa | 1620 |
| ggaaagaaga | cagagaagga | ggtgcaggaa | gctgagcaag | agactgctga agttgagacc | 1680 |
| ccagaagttg | atgagcctga | agattga | | | 1707 |

```
<210> SEQ ID NO 12
<211> LENGTH: 568
```

```
<212> TYPE: PRT
<213> ORGANISM: Lycopersicon esculentum

<400> SEQUENCE: 12
```

| Met | Thr | Asp | Val | Gln | Ala | Pro | Pro | Arg | Pro | Lys | Arg | Lys | Lys | Asn |
|---|---|---|---|---|---|---|---|---|---|---|---|---|---|---|
| 1 | | | | 5 | | | | | 10 | | | | | 15 |

| Ile | Met | Asp | Leu | Leu | Val | Gln | Phe | Arg | Trp | Ile | Val | Ile | Phe | Val |
|---|---|---|---|---|---|---|---|---|---|---|---|---|---|---|
| | | | | 20 | | | | | 25 | | | | | 30 |

| Val | Leu | Pro | Leu | Ser | Phe | Leu | Tyr | Tyr | Phe | Ser | Ile | Tyr | Leu | Gly | Asp |
|---|---|---|---|---|---|---|---|---|---|---|---|---|---|---|---|
| | | 35 | | | | | 40 | | | | | 45 | | | |

| Val | Arg | Ser | Glu | Cys | Lys | Ser | Tyr | Lys | Gln | Arg | Gln | Lys | Glu | His | Asp |
| | 50 | | | | | 55 | | | | | 60 | | | | |

| Glu | Asn | Val | Lys | Lys | Val | Val | Lys | Arg | Leu | Lys | Glu | Arg | Asn | Ala | Ser |
| 65 | | | | | 70 | | | | | 75 | | | | | 80 |

| Lys | Asp | Gly | Leu | Val | Cys | Thr | Ala | Arg | Lys | Pro | Trp | Val | Ala | Val | Gly |
| | | | | 85 | | | | | 90 | | | | | 95 | |

| Met | Arg | Asn | Val | Asp | Tyr | Lys | Arg | Ala | Arg | His | Phe | Glu | Val | Asp | Leu |
| | | | | 100 | | | | | 105 | | | | | 110 | |

| Ser | Pro | Phe | Arg | Asn | Val | Leu | Asn | Ile | Asp | Thr | Glu | Arg | Met | Ile | Ala |
| | | | 115 | | | | | 120 | | | | | 125 | | |

| Lys | Val | Glu | Pro | Leu | Val | Asn | Met | Gly | Gln | Ile | Ser | Arg | Val | Thr | Val |
| | 130 | | | | | 135 | | | | | 140 | | | | |

| Pro | Leu | Asn | Val | Ser | Leu | Ala | Val | Val | Ala | Glu | Leu | Asp | Asp | Leu | Thr |
| 145 | | | | | 150 | | | | | 155 | | | | | 160 |

| Val | Gly | Gly | Leu | Ile | Asn | Gly | Tyr | Gly | Ile | Glu | Gly | Ser | Ser | His | Ile |
| | | | | 165 | | | | | 170 | | | | | 175 | |

| Tyr | Gly | Leu | Phe | Ser | Asp | Thr | Val | Val | Ser | Tyr | Glu | Val | Val | Leu | Ala |
| | | | | 180 | | | | | 185 | | | | | 190 | |

| Asp | Gly | Gln | Val | Val | Arg | Ala | Thr | Lys | Asp | Asn | Glu | Tyr | Ser | Asp | Leu |
| | | 195 | | | | | 200 | | | | | 205 | | | |

| Phe | Tyr | Ala | Ile | Pro | Trp | Ser | Gln | Gly | Thr | Leu | Gly | Leu | Leu | Val | Ser |
| | 210 | | | | | 215 | | | | | 220 | | | | |

| Ala | Glu | Ile | Lys | Leu | Ile | Pro | Ile | Lys | Glu | Tyr | Met | Lys | Leu | Thr | Tyr |
| 225 | | | | | 230 | | | | | 235 | | | | | 240 |

| Lys | Pro | Val | Val | Gly | Asn | Leu | Lys | Glu | Ile | Ala | Gln | Ala | Tyr | Met | Asp |
| | | | | 245 | | | | | 250 | | | | | 255 | |

| Ser | Phe | Ser | Pro | Arg | Asp | Gly | Asp | Gln | Asp | Asn | His | Glu | Lys | Val | Pro |
| | | | 260 | | | | | 265 | | | | | 270 | | |

| Asp | Phe | Val | Glu | Thr | Met | Val | Tyr | Thr | Pro | Thr | Glu | Ala | Val | Cys | Met |
| | | | 275 | | | | | 280 | | | | | 285 | | |

| Thr | Gly | Arg | Tyr | Ala | Ser | Lys | Glu | Glu | Ala | Lys | Lys | Lys | Gly | Asn | Val |
| | 290 | | | | | 295 | | | | | 300 | | | | |

| Ile | Asn | Asn | Val | Gly | Trp | Trp | Phe | Lys | Thr | Trp | Phe | Tyr | Gln | His | Ala |
| 305 | | | | | 310 | | | | | 315 | | | | | 320 |

| Gln | Thr | Ala | Leu | Lys | Lys | Gly | Glu | Phe | Val | Gly | Tyr | Ile | Pro | Thr | Arg |
| | | | | 325 | | | | | 330 | | | | | 335 | |

| Glu | Tyr | Tyr | His | Arg | His | Thr | Arg | Cys | Leu | Tyr | Trp | Glu | Gly | Lys | Leu |
| | | | 340 | | | | | 345 | | | | | 350 | | |

| Ile | Leu | Pro | Phe | Gly | Asp | Gln | Trp | Trp | Phe | Arg | Phe | Leu | Phe | Gly | Trp |
| | | | 355 | | | | | 360 | | | | | 365 | | |

| Ala | Met | Pro | Pro | Lys | Val | Ser | Leu | Leu | Lys | Ala | Thr | Gln | Gly | Glu | Tyr |
| | 370 | | | | | 375 | | | | | 380 | | | | |

| Ile | Arg | Asn | Tyr | Tyr | His | Glu | Asn | His | Val | Ile | Gln | Asp | Met | Leu | Val |
| 385 | | | | | 390 | | | | | 395 | | | | | 400 |

```
Pro Leu Tyr Lys Val Gly Asp Ala Leu Glu Trp Val His Arg Glu Met
                405                 410                 415
Glu Val Tyr Pro Leu Trp Leu Cys Pro His Arg Leu Tyr Arg Leu Pro
            420                 425                 430
Leu Lys Thr Met Val Tyr Pro Glu Pro Gly Phe Glu Leu Gln Lys Arg
        435                 440                 445
Gln Gly Asp Thr Lys Tyr Ala Gln Met Tyr Thr Asp Val Gly Val Tyr
    450                 455                 460
Tyr Ala Pro Gly Pro Ile Leu Arg Gly Glu Val Phe Asp Gly Ile Glu
465                 470                 475                 480
Ala Val Arg Lys Leu Glu Ser Trp Leu Ile Glu Asn His Gly Phe Gln
                485                 490                 495
Pro Gln Tyr Ala Val Ser Glu Leu Thr Glu Lys Asn Phe Trp Arg Met
            500                 505                 510
Phe Asp Gly Ser Leu Tyr Glu Asn Cys Arg Lys Lys Tyr Arg Ala Ile
        515                 520                 525
Gly Thr Phe Met Ser Val Tyr Tyr Lys Ser Lys Lys Gly Lys Lys Thr
    530                 535                 540
Glu Lys Glu Val Gln Glu Ala Glu Gln Glu Thr Ala Glu Val Glu Thr
545                 550                 555                 560
Pro Glu Val Asp Glu Pro Glu Asp
                565

<210> SEQ ID NO 13
<211> LENGTH: 1686
<212> TYPE: DNA
<213> ORGANISM: Oryza sativa

<400> SEQUENCE: 13
atggcagatc tgcaggagcc cctcgttcgt ccgaagagga gaaggttttt ggtggactac     60
ttggtaaagt tccgatggat tctggtgatc tttgtggtgc tccccatttc cgctctgatc    120
tacttcaata tctatttggg cgatgtctgg tctgccatga atctgagaa acgtcgccag     180 aaggaacatg atgacaatgt gcaaaaagtt gtgaagcggc tcaagcagag gaacccaaag    240
aaggatggcc ttgtttgcac agctaggaag ccctggattg ctgttggcat gcgcaatgta    300
gactacaagc gtgctaggca tttttgaggtt gacctttccg ccttcaggaa cattcttgag    360
attgacagag agagaatggt tgccaaggtt gagcctcttg tcaacatggg ccagataacc    420
agagctacat gcccaatgaa ccttgcccctt gcagttgttg ctgagcttga tgaccttact    480 gttggggggac tgatcaatgg gtatggtatt gaagggagct ctcacctcta tggtcttttc    540
tctgacactg ttgtcgccgt ggaagttgtt cttgcagacg tcgagttgt tagagccact    600 aaggataatg agtactctga ccttttctat ggcattcct ggtcccaggg aacacttggg    660
tttcttgttt ccgctgagat caaactcatt cccatcaagg aatacatgag gctcacatat    720
actccagtta aagggtcact gaaggagata gcacaaggtt attgtgattc gtttgcacca    780
cgagatggtg atcctgcaaa ggtcccagac ttcgttgagg gaatggtgta cacagaaaat    840
gagggtgtca tgatgactgg tgtttatgct tccaaagaag aggcaaagaa gaagggcaat    900
aagatcaact gtgtcgggtg gtggttcaag ccttggtttt accaacatgc tcagacagca    960
ctcaagaagg gtgagtttgt ggagtacatt ccaacaagag agtactacca ccgtcacacc   1020
cggtgtctgt actgggaggg gaagctgatc ttgccattcg gcgaccaatt ctggttcagg   1080
ttcctcttgg gctggctgat gccaccaaag ggtgtctctgc tcaaggccac acagggtgaa   1140
tctatcagga attactacca tgacaaccat gtgattcaag acatgctggt tcccttgtac   1200
```

-continued

```
aaagttggag atgctcttga gtttgttcac aaggaaatgg aggtttatcc actgtggctg    1260
tgcccgcacc ggctctacaa gctccctgtg aaaaccatgg tgtacccaga gcctggcttt    1320
gagcaccacc acaggcaagg tgacactagc tatgcccaga tgttcaccga tgttggtgtg    1380
tactatgctc ctggtgctgt cctgaggggc gaggagttca atggcgctct agctgtccac    1440
aggctggagc agtggctgat tgagaaccac agctaccagc acagtacgcg tgtatctgag    1500
ctcaacgaga aggacttctg gaggatgttt gatgcttctc actacgagca ttgccgccaa    1560
aagtatggtg ccgtcggtac ctttatgagc gtctactaca agtccaagaa gggaaggaag    1620
actgagaagg aggtgcagga agccgaggcc gccatcctcg agccagccta cgctgatgag    1680
gcgtaa                                                               1686
```

<210> SEQ ID NO 14
<211> LENGTH: 561
<212> TYPE: PRT
<213> ORGANISM: Oryza sativa

<400> SEQUENCE: 14

```
Met Ala Asp Leu Gln Glu Pro Leu Val Arg Pro Lys Arg Lys Lys Val
1               5                  10                  15

Leu Val Asp Tyr Leu Val Lys Phe Arg Trp Ile Leu Val Ile Phe Val
            20                  25                  30

Val Leu Pro Ile Ser Ala Leu Ile Tyr Phe Asn Ile Tyr Leu Gly Asp
        35                  40                  45

Val Trp Ser Ala Met Lys Ser Glu Lys Arg Gln Lys Glu His Asp
    50                  55                  60

Asp Asn Val Gln Lys Val Val Lys Arg Leu Lys Gln Arg Asn Pro Lys
65                  70                  75                  80

Lys Asp Gly Leu Val Cys Thr Ala Arg Lys Pro Trp Ile Ala Val Gly
                85                  90                  95

Met Arg Asn Val Asp Tyr Lys Arg Ala Arg His Phe Glu Val Asp Leu
            100                 105                 110

Ser Ala Phe Arg Asn Ile Leu Glu Ile Asp Arg Glu Arg Met Val Ala
        115                 120                 125

Lys Val Glu Pro Leu Val Asn Met Gly Gln Ile Thr Arg Ala Thr Cys
    130                 135                 140

Pro Met Asn Leu Ala Leu Ala Val Val Ala Glu Leu Asp Asp Leu Thr
145                 150                 155                 160

Val Gly Gly Leu Ile Asn Gly Tyr Gly Ile Glu Gly Ser Ser His Leu
                165                 170                 175

Tyr Gly Leu Phe Ser Asp Thr Val Ala Val Glu Val Val Leu Ala
            180                 185                 190

Asp Gly Arg Val Val Arg Ala Thr Lys Asp Asn Glu Tyr Ser Asp Leu
        195                 200                 205

Phe Tyr Gly Ile Pro Trp Ser Gln Gly Thr Leu Gly Phe Leu Val Ser
    210                 215                 220

Ala Glu Ile Lys Leu Ile Pro Ile Lys Glu Tyr Met Arg Leu Thr Tyr
225                 230                 235                 240

Thr Pro Val Lys Gly Ser Leu Lys Glu Ile Ala Gln Gly Tyr Cys Asp
                245                 250                 255

Ser Phe Ala Pro Arg Asp Gly Asp Pro Ala Lys Val Pro Asp Phe Val
            260                 265                 270

Glu Gly Met Val Tyr Thr Glu Asn Glu Gly Val Met Met Thr Gly Val
        275                 280                 285
```

-continued

```
Tyr Ala Ser Lys Glu Glu Ala Lys Lys Gly Asn Lys Ile Asn Cys
    290                 295                 300
Val Gly Trp Trp Phe Lys Pro Trp Phe Tyr Gln His Ala Gln Thr Ala
305                 310                 315                 320
Leu Lys Lys Gly Glu Phe Val Glu Tyr Ile Pro Thr Arg Glu Tyr Tyr
                325                 330                 335
His Arg His Thr Arg Cys Leu Tyr Trp Glu Gly Lys Leu Ile Leu Pro
            340                 345                 350
Phe Gly Asp Gln Phe Trp Phe Arg Phe Leu Leu Gly Trp Leu Met Pro
        355                 360                 365
Pro Lys Val Ser Leu Leu Lys Ala Thr Gln Gly Glu Ser Ile Arg Asn
    370                 375                 380
Tyr Tyr His Asp Asn His Val Ile Gln Asp Met Leu Val Pro Leu Tyr
385                 390                 395                 400
Lys Val Gly Asp Ala Leu Glu Phe Val His Lys Glu Met Glu Val Tyr
                405                 410                 415
Pro Leu Trp Leu Cys Pro His Arg Leu Tyr Lys Leu Pro Val Lys Thr
            420                 425                 430
Met Val Tyr Pro Glu Pro Gly Phe Glu His His Arg Gln Gly Asp
        435                 440                 445
Thr Ser Tyr Ala Gln Met Phe Thr Asp Val Gly Val Tyr Tyr Ala Pro
    450                 455                 460
Gly Ala Val Leu Arg Gly Glu Phe Asn Gly Ala Leu Ala Val His
465                 470                 475                 480
Arg Leu Glu Gln Trp Leu Ile Glu Asn His Ser Tyr Gln Pro Gln Tyr
                485                 490                 495
Ala Val Ser Glu Leu Asn Glu Lys Asp Phe Trp Arg Met Phe Asp Ala
            500                 505                 510
Ser His Tyr Glu His Cys Arg Gln Lys Tyr Gly Ala Val Gly Thr Phe
        515                 520                 525
Met Ser Val Tyr Tyr Lys Ser Lys Lys Gly Arg Lys Thr Glu Lys Glu
    530                 535                 540
Val Gln Glu Ala Glu Ala Ile Leu Glu Pro Ala Tyr Ala Asp Glu
545                 550                 555                 560
Ala
```

<210> SEQ ID NO 15
<211> LENGTH: 1704
<212> TYPE: DNA
<213> ORGANISM: Pisum sativum

<400> SEQUENCE: 15

```
atgtctgatc ttgaggctcc gctgcgcccg aagaggaaga agatttgggt ggactacttt      60
gttaagttta gatggattct tgttattttt gtggttcttc ccatttcctt cacactttat     120
tttcttacat accttgggga tgtgagatct gagtggaagt cctttaagac gcggcagaag     180
gaacacgatg agaatgtcca gaaggttgtc aatcgcctca aaagaggaa tccttcaaag     240
gatgggcttg tgtgcactgc tcgtaagcca tgggttgctg ttgggatgag aaatgttgac     300
tataagaggg ctcgtcattt tgaggttgat ctttctcctt tcaggaacat tcttgatatc     360
gacaaagagc ggatgattgc tagggtagag ccccttgtca catggggca gatcaccagg     420
gtgactgtgc ctatgaatct tgcactcgct gtggttgctg agctcgatga tcttactgtt     480
ggtggcctca taaatggtta tgggatcgaa ggaagttccc acaaatatgg ccttttttct     540
```

```
gatactgttg tagcctttga aattattttg gcagatggat ctcttgttaa agccaccaag    600
gacaatgagt actctgatct attttatgct attccatggt ctcagggaac acttgggctt    660
cttgttgctg ctgaggtcaa gcttataccc attaaggagt acatgaagtt aacttataaa    720
ccagttgttg gtaacctgaa agatattgca caggcatatt ctgattcttt tgctcccaga    780
gacggtgacc aggataatga tgagaaggtt ccagactttg ttgaaactat gatttattcg    840
ccaacacgag ctgtgtgcat gacagggaga tatgcttcaa aggaagaggc caagaaaaag    900
gggaataaga ttaacaatgt agggtggtgg tacaaaacct ggttctacca acatgcagag    960
acagcactca agaaaggtct gtttgtagaa tacattccca ccagagagta ttatcacagg   1020
cacacaaggt gtttgtattg ggagggaaag cttatcctcc catttggtga tcaattttgg   1080
tttagatttc tgtttggctg gttgatgcca cccaaggttt cttttgctcaa ggcaactcaa   1140
ggggaagcta ttagaaacta ttaccatgaa atgcatgtta tccaggacat gcttgttcct   1200
ctgtacaagg tgggagatgc actagaatgg gttgaccgtg agatggaggt atacccatt    1260
tggctctgtc cacataaact gttcaagctg cctatcaaaa ctatgattta cccagaagca   1320
ggctttgagt tgcaacgcag gcagggagac acacagaatg ctcagatgtt cacagatgtt   1380
ggagtttact atgcaccagg tcctgtgtta agggcgagg tgtttgatgg tgcagaagca   1440
gtgcgtaaaa tggagagctg gatgattgag aatcattgtt ttcagccaca gtatgctgtg   1500
tctgagctga atgagaaaaa cttctggagg atgtttgatg ctggtctgta tgagcattgt   1560
aggaggaagt atggagccgt tggaactttt atgagtgtgt actacaaatg caagaagggc   1620
aggaaaactg agaaggaagt gcgtgaagcc gagcaagcac accttgacac tgcgtatgca   1680
gaagttgatc aaccagcaga ctga                                           1704
```

<210> SEQ ID NO 16
<211> LENGTH: 567
<212> TYPE: PRT
<213> ORGANISM: Pisum sativum

<400> SEQUENCE: 16

```
Met Ser Asp Leu Glu Ala Pro Leu Arg Pro Lys Arg Lys Lys Ile Trp
1               5                   10                  15

Val Asp Tyr Phe Val Lys Phe Arg Trp Ile Leu Val Ile Phe Val Val
            20                  25                  30

Leu Pro Ile Ser Phe Thr Leu Tyr Phe Leu Thr Tyr Leu Gly Asp Val
        35                  40                  45

Arg Ser Glu Trp Lys Ser Phe Lys Thr Arg Gln Lys Glu His Asp Glu
    50                  55                  60

Asn Val Gln Lys Val Val Asn Arg Leu Lys Lys Arg Asn Pro Ser Lys
65                  70                  75                  80

Asp Gly Leu Val Cys Thr Ala Arg Lys Pro Trp Val Ala Val Gly Met
                85                  90                  95

Arg Asn Val Asp Tyr Lys Arg Ala Arg His Phe Glu Val Asp Leu Ser
            100                 105                 110

Pro Phe Arg Asn Ile Leu Asp Ile Asp Lys Glu Arg Met Ile Ala Arg
        115                 120                 125

Val Glu Pro Leu Val Asn Met Gly Gln Ile Thr Arg Val Thr Val Pro
    130                 135                 140

Met Asn Leu Ala Leu Ala Val Val Ala Glu Leu Asp Asp Leu Thr Val
145                 150                 155                 160

Gly Gly Leu Ile Asn Gly Tyr Gly Ile Glu Gly Ser Ser His Lys Tyr
                165                 170                 175
```

Gly Leu Phe Ser Asp Thr Val Val Ala Phe Glu Ile Ile Leu Ala Asp
            180                 185                 190

Gly Ser Leu Val Lys Ala Thr Lys Asp Asn Glu Tyr Ser Asp Leu Phe
        195                 200                 205

Tyr Ala Ile Pro Trp Ser Gln Gly Thr Leu Gly Leu Leu Val Ala Ala
    210                 215                 220

Glu Val Lys Leu Ile Pro Ile Lys Glu Tyr Met Lys Leu Thr Tyr Lys
225                 230                 235                 240

Pro Val Val Gly Asn Leu Lys Asp Ile Ala Gln Ala Tyr Ser Asp Ser
                245                 250                 255

Phe Ala Pro Arg Asp Gly Asp Gln Asp Asn Asp Glu Lys Val Pro Asp
            260                 265                 270

Phe Val Glu Thr Met Ile Tyr Ser Pro Thr Arg Ala Val Cys Met Thr
        275                 280                 285

Gly Arg Tyr Ala Ser Lys Glu Glu Ala Lys Lys Gly Asn Lys Ile
    290                 295                 300

Asn Asn Val Gly Trp Trp Tyr Lys Thr Trp Phe Tyr Gln His Ala Glu
305                 310                 315                 320

Thr Ala Leu Lys Lys Gly Leu Phe Val Glu Tyr Ile Pro Thr Arg Glu
                325                 330                 335

Tyr Tyr His Arg His Thr Arg Cys Leu Tyr Trp Glu Gly Lys Leu Ile
            340                 345                 350

Leu Pro Phe Gly Asp Gln Phe Trp Phe Arg Phe Leu Phe Gly Trp Leu
        355                 360                 365

Met Pro Pro Lys Val Ser Leu Leu Lys Ala Thr Gln Gly Glu Ala Ile
    370                 375                 380

Arg Asn Tyr Tyr His Glu Met His Val Ile Gln Asp Met Leu Val Pro
385                 390                 395                 400

Leu Tyr Lys Val Gly Asp Ala Leu Glu Trp Val Asp Arg Glu Met Glu
                405                 410                 415

Val Tyr Pro Ile Trp Leu Cys Pro His Lys Leu Phe Lys Leu Pro Ile
            420                 425                 430

Lys Thr Met Ile Tyr Pro Glu Ala Gly Phe Glu Leu Gln Arg Arg Gln
        435                 440                 445

Gly Asp Thr Gln Asn Ala Gln Met Phe Thr Asp Val Gly Val Tyr Tyr
    450                 455                 460

Ala Pro Gly Pro Val Leu Arg Gly Glu Val Phe Asp Gly Ala Glu Ala
465                 470                 475                 480

Val Arg Lys Met Glu Ser Trp Met Ile Glu Asn His Cys Phe Gln Pro
                485                 490                 495

Gln Tyr Ala Val Ser Glu Leu Asn Glu Lys Asn Phe Trp Arg Met Phe
            500                 505                 510

Asp Ala Gly Leu Tyr Glu His Cys Arg Arg Lys Tyr Gly Ala Val Gly
        515                 520                 525

Thr Phe Met Ser Val Tyr Tyr Lys Cys Lys Lys Gly Arg Lys Thr Glu
    530                 535                 540

Lys Glu Val Arg Glu Ala Glu Gln Ala His Leu Asp Thr Ala Tyr Ala
545                 550                 555                 560

Glu Val Asp Gln Pro Ala Asp
                565

<210> SEQ ID NO 17
<211> LENGTH: 1692
<212> TYPE: DNA

<213> ORGANISM: Populus tremuloides

<400> SEQUENCE: 17

```
atgtctgatc tcgaggcccc cctgcgccca agaggaaga aggtgtgggt agactatttt    60
gtccagttca gatggatctt agttattttt gttgttctcc caatctcctt cacccttac   120
tttctcactt accttgggga tgtcaaatca gagatgaaat cctacaaaca gcgtcagaag   180
gaacatgatg aaaatgttaa aaagtggtg aaacgcctca agagaggaa tccatccaag   240
gatggtcttg tttgcactgc tcgtaaaccc tggattgctg ttggaatgcg aatgttgac    300
tataaacggg ctcggcactt tgaagttgat ttatcatctt ccgtaatat ccttgaaatt    360
gacagagaga gaatggttgc aagagttgag ccacttgtaa atatgggaca gattagcagg   420
gcgagtgtcc caatgaatct tcccttgca gtggttgcag aacttgatga tctcactgtt   480
ggtgggctaa ttaatggtta tgggattgaa ggaagctctc acatctatgg cttgttctct   540
gacactgttg tggcttatga gattgttttg gcagatggcc aggttgttag agccaccaag   600
gacaatgaat actctgatct tttctatgcc atcccttggt ctcagggaac acttgggctt   660
cttgtctctg ctgagatcaa gcttattccc gttaaggaat acatgaggct gacctacaaa   720
cctgtggtgg gtaatctgaa agaacttgca caggcctata tagactcttt tgcacccaga   780
gatggagatc aggataaccc gagcaaggtt ccagactttg tggagactat gatttataac   840
tctaccgatg gtgtgatgat gacagggaga tatgcctcca agaagaggc caagaagaag   900
ggaaatgtga ttaacaatgt tggttggtgg tttaaaccgt ggttctatca gcatgcgcag   960
acagccctaa agaaggggga gtttgtagag tacattccaa ccagagaata ttaccacagg  1020
cacacaaggt gtttgtactg ggaggggaag ctcatacttc catttgctga ccaatggtgg  1080
tttagatttc tcttaggctg gatgatgcct ccaaaggttt ctcttctcaa ggctactcaa  1140
ggtgaagcaa tcagaaacta ttaccatgag atgcatgtca ttcaggatat gcttgttcct  1200
ctttacaagg ttggggatgc cctagaatgg gtcgaccgtg agatggaggt atatcccatt  1260
tggcttttgtc cgcacaggtt gttcaagctt cctgtgaaaa ctatggtgta tcctgagcca  1320
gggtttgagc atcagcacag acaggagac acatcctatg cccagatgta caccgatgtt  1380
ggggtgtatt attcacctgg acctgtgttg aggggtgagg tgtttgaagg tgcagatgca  1440
gttcgtagaa tggaggactg gttgatagaa accacggct tccagcctca gtatgcagtg  1500
tctgagctga atgagaagaa attctggagg atgtttgatg ctgacctcta tgaacacgcc  1560
aggaagaaat atggagctgt gggaaccttc atgagcgtgt actacaaatc caagaaagga  1620
aggaagacgg agaaggaggt gcaggaagca gaacaagccc accttgagac tgcttatgct  1680
gaggctggtt ag                                                       1692
```

<210> SEQ ID NO 18
<211> LENGTH: 563
<212> TYPE: PRT
<213> ORGANISM: Populus tremuloides

<400> SEQUENCE: 18

```
Met Ser Asp Leu Glu Ala Pro Leu Arg Pro Lys Arg Lys Lys Val Trp
1               5                   10                  15

Val Asp Tyr Phe Val Gln Phe Arg Trp Ile Leu Val Ile Phe Val Val
            20                  25                  30

Leu Pro Ile Ser Phe Thr Leu Tyr Phe Leu Thr Tyr Leu Gly Asp Val
        35                  40                  45

Lys Ser Glu Met Lys Ser Tyr Lys Gln Arg Gln Lys Glu His Asp Glu
```

```
            50                  55                  60
Asn Val Lys Lys Val Lys Arg Leu Lys Glu Arg Asn Pro Ser Lys
 65                  70                  75                  80

Asp Gly Leu Val Cys Thr Ala Arg Lys Pro Trp Ile Ala Val Gly Met
                     85                  90                  95

Arg Asn Val Asp Tyr Lys Arg Ala Arg His Phe Glu Val Asp Leu Ser
                    100                 105                 110

Ser Phe Arg Asn Ile Leu Glu Ile Asp Arg Glu Arg Met Val Ala Arg
                    115                 120                 125

Val Glu Pro Leu Val Asn Met Gly Gln Ile Ser Arg Ala Ser Val Pro
                130                 135                 140

Met Asn Leu Ser Leu Ala Val Ala Glu Leu Asp Asp Leu Thr Val
145                 150                 155                 160

Gly Gly Leu Ile Asn Gly Tyr Gly Ile Glu Gly Ser Ser His Ile Tyr
                    165                 170                 175

Gly Leu Phe Ser Asp Thr Val Val Ala Tyr Glu Ile Val Leu Ala Asp
                    180                 185                 190

Gly Gln Val Val Arg Ala Thr Lys Asp Asn Glu Tyr Ser Asp Leu Phe
                195                 200                 205

Tyr Ala Ile Pro Trp Ser Gln Gly Thr Leu Gly Leu Leu Val Ser Ala
210                 215                 220

Glu Ile Lys Leu Ile Pro Val Lys Glu Tyr Met Arg Leu Thr Tyr Lys
225                 230                 235                 240

Pro Val Val Gly Asn Leu Lys Glu Leu Ala Gln Ala Tyr Ile Asp Ser
                    245                 250                 255

Phe Ala Pro Arg Asp Gly Asp Gln Asp Asn Pro Ser Lys Val Pro Asp
                260                 265                 270

Phe Val Glu Thr Met Ile Tyr Asn Ser Thr Asp Gly Val Met Met Thr
                275                 280                 285

Gly Arg Tyr Ala Ser Lys Glu Ala Lys Lys Gly Asn Val Ile
                290                 295                 300

Asn Asn Val Gly Trp Trp Phe Lys Pro Trp Phe Tyr Gln His Ala Gln
305                 310                 315                 320

Thr Ala Leu Lys Lys Gly Glu Phe Val Glu Tyr Ile Pro Thr Arg Glu
                    325                 330                 335

Tyr Tyr His Arg His Thr Arg Cys Leu Tyr Trp Glu Gly Lys Leu Ile
                    340                 345                 350

Leu Pro Phe Ala Asp Gln Trp Trp Phe Arg Phe Leu Leu Gly Trp Met
                    355                 360                 365

Met Pro Pro Lys Val Ser Leu Leu Lys Ala Thr Gln Gly Glu Ala Ile
370                 375                 380

Arg Asn Tyr Tyr His Glu Met His Val Ile Gln Asp Met Leu Val Pro
385                 390                 395                 400

Leu Tyr Lys Val Gly Asp Ala Leu Glu Trp Val Asp Arg Glu Met Glu
                    405                 410                 415

Val Tyr Pro Ile Trp Leu Cys Pro His Arg Leu Phe Lys Leu Pro Val
                    420                 425                 430

Lys Thr Met Val Tyr Pro Glu Pro Gly Phe Glu His Gln His Arg Gln
                    435                 440                 445

Gly Asp Thr Ser Tyr Ala Gln Met Tyr Thr Asp Val Gly Val Tyr Tyr
                450                 455                 460

Ser Pro Gly Pro Val Leu Arg Gly Glu Val Phe Glu Gly Ala Asp Ala
465                 470                 475                 480
```

```
Val Arg Arg Met Glu Asp Trp Leu Ile Glu Asn His Gly Phe Gln Pro
            485                 490                 495

Gln Tyr Ala Val Ser Glu Leu Asn Glu Lys Lys Phe Trp Arg Met Phe
        500                 505                 510

Asp Ala Asp Leu Tyr Glu His Ala Arg Lys Lys Tyr Gly Ala Val Gly
        515                 520                 525

Thr Phe Met Ser Val Tyr Tyr Lys Ser Lys Gly Arg Lys Thr Glu
    530                 535                 540

Lys Glu Val Gln Glu Ala Glu Gln Ala His Leu Glu Thr Ala Tyr Ala
545                 550                 555                 560

Glu Ala Gly

<210> SEQ ID NO 19
<211> LENGTH: 1686
<212> TYPE: DNA
<213> ORGANISM: Triticum aestivum

<400> SEQUENCE: 19
atggcggacc tgcagacgcc gctggtgcga ccaaagagga agaaggttct ggtggactac      60
ctggtgcagt ccgatggat cctcgtcatc ttcgtggtgc ttccgggctc ggggctcatc     120
tacttcaaca tctacctggg cgacatgtgg tccgccatga agtccgagaa gaagcggcag     180
aaggagcacg aggacaacgt gcagaaggtc gtgaagcggc tcaagcagcg caaccccaag     240
aaggacggcc tcgtctgcac ggccaggaag ccgtggatcg ccgtcggcat gcgcaacgtg     300
gactacaagc gcgtcaggca cttcgaggtc gacctctccg ccttcaggaa catcctcgag     360
atcgacgccg agaggatggt cgccaaggtc gagccgctcg tcaacatggg ccagatatcc     420
agggccacct gccccatgaa cctctcccctc gccgtggtgg cggagctcga cgacctcacc     480
gtcggcggcc tcatcaacgg ctacggcatc gaggggagct ctcacatcta cgggctcttc     540
tccgacacgt tgtcgcgct ggagatcgtc ctggctgacg ccgggtcgt ccgagccacc     600 aaggacaacg agtactccga cctcttctac ggcgtgccct ggtcgcaggg aactctcggg     660
ttccttgtct cagccgagat caagctcatc cccatcaagg agtacatgag gctcacctac     720 accctgtga agggccctct gaaggaggtg gcgcaggcat acgccgacgc cgtcgcgccg     780
agggacggcg accccgcaaa ggtccccgac ttcgtggaag ggatggtgta cagcgcgacg     840
gagggcgtga tgatgaccgg cgtgtacgcg tccaaggagg aggccaagaa gaagggcaac     900
aagatcaaca cgtggggtg tgtggttcaag ccatggttct accagcacgc gcagacggcg     960
ctcaagaagg gcgagttcgt ggagtacatc ccgacgaggg agtactacca caggcacacc    1020
cggtgcctgt actgggaggg gaagctcatc ctgcccttcg cgaccagtt ctggttcagg    1080 ttcctcttcg gctggctgat gccccccaag gtgtccctgc tcaaggccac ccagggcgac    1140
gccatcagga actactacca tgacaaccat gtcatccagg acatgctggt gcccctgtac    1200
aaggttggag acgccctcga gttcgtccac cacgagatgg aggtgtaccc gctgtggctg    1260
tgccctcacc ggctgttcaa gctgccggtg aagacgatga tctacccgga gccggggttc    1320
gagcaccagc agcggcaggg ggacacgagc tacgcgcaga tgttcacgga cgtgggggtg    1380
tactacacgc cggcgtgcat cttccgcggg gaggagttcg acggggcgga gtcggtgaag    1440
cggctggagc agtggctgat cgagaaccac agctaccagc gcagtacgc ggtgacggga    1500 ctgaacgaga aggacttctg gcgcatgttc gacgcgtcgc actacgagca ctgccggcac    1560
aagtacggcg ccgtgggcac cttcatgagc gtctactaca agagcaagaa ggggcgcaag    1620
tccgagaagg aggtgcagga ggccgaggcc gccatcctgg agcccgccta cgccgacgag    1680
```

```
gcctag                                                              1686
```

<210> SEQ ID NO 20
<211> LENGTH: 561
<212> TYPE: PRT
<213> ORGANISM: Triticum aestivum

<400> SEQUENCE: 20

```
Met Ala Asp Leu Gln Thr Pro Leu Val Arg Pro Lys Arg Lys Lys Val
1               5                   10                  15

Leu Val Asp Tyr Leu Val Gln Phe Arg Trp Ile Leu Val Ile Phe Val
            20                  25                  30

Val Leu Pro Gly Ser Gly Leu Ile Tyr Phe Asn Ile Tyr Leu Gly Asp
        35                  40                  45

Met Trp Ser Ala Met Lys Ser Glu Lys Lys Arg Gln Lys Glu His Glu
    50                  55                  60

Asp Asn Val Gln Lys Val Val Lys Arg Leu Lys Gln Arg Asn Pro Lys
65                  70                  75                  80

Lys Asp Gly Leu Val Cys Thr Ala Arg Lys Pro Trp Ile Ala Val Gly
                85                  90                  95

Met Arg Asn Val Asp Tyr Lys Arg Val Arg His Phe Glu Val Asp Leu
            100                 105                 110

Ser Ala Phe Arg Asn Ile Leu Glu Ile Asp Ala Glu Arg Met Val Ala
        115                 120                 125

Lys Val Glu Pro Leu Val Asn Met Gly Gln Ile Ser Arg Ala Thr Cys
130                 135                 140

Pro Met Asn Leu Ser Leu Ala Val Val Ala Glu Leu Asp Asp Leu Thr
145                 150                 155                 160

Val Gly Gly Leu Ile Asn Gly Tyr Gly Ile Glu Gly Ser Ser His Ile
                165                 170                 175

Tyr Gly Leu Phe Ser Asp Thr Val Ala Leu Glu Ile Val Leu Ala
            180                 185                 190

Asp Gly Arg Val Val Arg Ala Thr Lys Asp Asn Glu Tyr Ser Asp Leu
        195                 200                 205

Phe Tyr Gly Val Pro Trp Ser Gln Gly Thr Leu Gly Phe Leu Val Ser
    210                 215                 220

Ala Glu Ile Lys Leu Ile Pro Ile Lys Glu Tyr Met Arg Leu Thr Tyr
225                 230                 235                 240

Thr Pro Val Lys Gly Pro Leu Lys Glu Val Ala Gln Tyr Ala Asp
                245                 250                 255

Ala Val Ala Pro Arg Asp Gly Asp Pro Ala Lys Val Pro Asp Phe Val
            260                 265                 270

Glu Gly Met Val Tyr Ser Ala Thr Glu Gly Val Met Met Thr Gly Val
        275                 280                 285

Tyr Ala Ser Lys Glu Glu Ala Lys Lys Gly Asn Lys Ile Asn Ser
    290                 295                 300

Val Gly Trp Trp Phe Lys Pro Trp Phe Tyr Gln His Ala Gln Thr Ala
305                 310                 315                 320

Leu Lys Lys Gly Glu Phe Val Glu Tyr Ile Pro Thr Arg Glu Tyr Tyr
                325                 330                 335

His Arg His Thr Arg Cys Leu Tyr Trp Glu Gly Lys Leu Ile Leu Pro
            340                 345                 350

Phe Gly Asp Gln Phe Trp Phe Arg Phe Leu Phe Gly Trp Leu Met Pro
        355                 360                 365
```

```
Pro Lys Val Ser Leu Leu Lys Ala Thr Gln Gly Asp Ala Ile Arg Asn
        370                 375                 380

Tyr Tyr His Asp Asn His Val Ile Gln Asp Met Leu Val Pro Leu Tyr
385                 390                 395                 400

Lys Val Gly Asp Ala Leu Glu Phe Val His His Glu Met Glu Val Tyr
                405                 410                 415

Pro Leu Trp Leu Cys Pro His Arg Leu Phe Lys Leu Pro Val Lys Thr
            420                 425                 430

Met Ile Tyr Pro Glu Pro Gly Phe Glu His Gln Gln Arg Gln Gly Asp
        435                 440                 445

Thr Ser Tyr Ala Gln Met Phe Thr Asp Val Gly Val Tyr Tyr Thr Pro
    450                 455                 460

Ala Cys Ile Phe Arg Gly Glu Glu Phe Asp Gly Ala Glu Ser Val Lys
465                 470                 475                 480

Arg Leu Glu Gln Trp Leu Ile Glu Asn His Ser Tyr Gln Pro Gln Tyr
                485                 490                 495

Ala Val Thr Glu Leu Asn Glu Lys Asp Phe Trp Arg Met Phe Asp Ala
                500                 505                 510

Ser His Tyr Glu His Cys Arg His Lys Tyr Gly Ala Val Gly Thr Phe
            515                 520                 525

Met Ser Val Tyr Tyr Lys Ser Lys Lys Gly Arg Lys Ser Glu Lys Glu
        530                 535                 540

Val Gln Glu Ala Glu Ala Ile Leu Glu Pro Ala Tyr Ala Asp Glu
545                 550                 555                 560

Ala

<210> SEQ ID NO 21
<211> LENGTH: 1689
<212> TYPE: DNA
<213> ORGANISM: Zea mays

<400> SEQUENCE: 21
atggcggacg tgcacgaacc tttggtgcgc cgtaagagga agaaggtttt ggtggactac      60
ttggtgaagt tccgatggat cctcgtgatc ttcgtggtcc ttcctatttc aactctgatc     120
tacttcaaca tcttcctggg cgacatgtgg tccgccatga agtcggagaa gaagcgccag     180
aagcagcacg acgagaacgt gcagaaggtc gtgaagcggc tcaagcagag gaacccgaag     240
aaggacggtc ttgtttgcac ggccaggaag ccctggatcg ctgttggcat gcgcaacgtg     300
gactacaagc gtgcgaggca tttcgaggtc gacctttctt ccttcaggaa catccttgag     360
atcgacaaag agaggatggt tgccaaggtc gagccccttg tcaacatggg tcagataacc     420
agagctacct gcccaatgaa ccttgccctt gcggtcgtcg ccgagctcga cgacctcact     480
gttggtgggc tgatcaacgg ttacggcatc gaggggagct ctcacctcta tggcctttc     540
tccgacacgg ttgtcgcgat ggaggttgtt ctcgcagatg gccgggtcgt cagagccacc     600
aaggacaacg agtactctga ccttttctat ggaattccct ggtcccaggg aacactgggg     660
ttccttgtct ctgcagagat caagctgatc cccatcaagg agtacatgaa gctcacctac     720
actccagtca aggggggtct aaaggagatc gcgcaggcct acgcggattc tttcgctccg     780
agggacggtg acccggcaaa ggtccctgac tttgttgaag gatggtgta cacagagagc     840
gagggtgtca tgatgacggg cgtgtacgct tcgaaagaag aggcgaagaa gaagggcaac     900
aagatcaact gctgggggtg gtggtttaag ccctggttct accagcacgc tcagacggcg     960
ctgaataggg gcgagtttgt ggagtacatc ccgacgaggg agtactacca ccggcacacc    1020
```

```
cggtgcctgt actgggaggg gaagctgatc ctgcccttcg gcgaccagtt ctggttcagg    1080
ttcctgctgg gctggctgat gccaccgaag gtgtccctgc tgaaggcgac ccagggcgag    1140
gctatcagga actactacca cgacaaccat gtgatccagg acatgctggt gccgctgtac    1200
aaggttgggg atgcgctgga gttcgtgcac cgcgagatgg aggtgtatcc tctgtggctg    1260
tgccctcacc ggctgtacaa gctgccggtg aagacgatgg tgtacccgga gcctgggttc    1320
gagcaccagc acaggcaggg cgacgcgagc tacgcacaga tgttcacgga cgtgggcgtg    1380
tactacgccc ccggggcggt gctgaggggg gaggagttca acggcgcgga ggctgtgcac    1440
aggctggagc agtggctgat cgagaaccac agctaccagc cgcagtacgc ggtgtcggag    1500
ctgaacgaga aggactcctg gcgcatgttc gacgcgtcgc actacgagca ctgccgccaa    1560
aagtacgggg cggtgggcac gttcatgagc gtgtactaca agtccaagaa ggggcgcaag    1620
acggagaagg aggtgcagga ggcggaggcg gccatactgg agccggccta cgcggacgag    1680
gaggcctaa                                                            1689
```

<210> SEQ ID NO 22
<211> LENGTH: 562
<212> TYPE: PRT
<213> ORGANISM: Zea mays

<400> SEQUENCE: 22

```
Met Ala Asp Val His Glu Pro Leu Val Arg Arg Lys Arg Lys Lys Val
1               5                   10                  15

Leu Val Asp Tyr Leu Val Lys Phe Arg Trp Ile Leu Ile Phe Val
            20                  25                  30

Val Leu Pro Ile Ser Thr Leu Ile Tyr Phe Asn Ile Phe Leu Gly Asp
        35                  40                  45

Met Trp Ser Ala Met Lys Ser Glu Lys Lys Arg Gln Lys Gln His Asp
    50                  55                  60

Glu Asn Val Gln Lys Val Val Lys Arg Leu Lys Gln Arg Asn Pro Lys
65                  70                  75                  80

Lys Asp Gly Leu Val Cys Thr Ala Arg Lys Pro Trp Ile Ala Val Gly
                85                  90                  95

Met Arg Asn Val Asp Tyr Lys Arg Ala Arg His Phe Glu Val Asp Leu
            100                 105                 110

Ser Ser Phe Arg Asn Ile Leu Glu Ile Asp Lys Glu Arg Met Val Ala
        115                 120                 125

Lys Val Glu Pro Leu Val Asn Met Gly Gln Ile Thr Arg Ala Thr Cys
    130                 135                 140

Pro Met Asn Leu Ala Leu Ala Val Val Ala Glu Leu Asp Asp Leu Thr
145                 150                 155                 160

Val Gly Gly Leu Ile Asn Gly Tyr Gly Ile Glu Gly Ser Ser His Leu
                165                 170                 175

Tyr Gly Leu Phe Ser Asp Thr Val Ala Met Glu Val Leu Ala
            180                 185                 190

Asp Gly Arg Val Val Arg Ala Thr Lys Asp Asn Glu Tyr Ser Asp Leu
        195                 200                 205

Phe Tyr Gly Ile Pro Trp Ser Gln Gly Thr Leu Gly Phe Leu Val Ser
    210                 215                 220

Ala Glu Ile Lys Leu Ile Pro Ile Lys Glu Tyr Met Lys Leu Thr Tyr
225                 230                 235                 240

Thr Pro Val Lys Gly Gly Leu Val Glu Ile Ala Gln Ala Tyr Ala Asp
                245                 250                 255
```

Ser Phe Ala Pro Arg Asp Gly Asp Pro Ala Lys Val Pro Asp Phe Val
                260                 265                 270

Glu Gly Met Val Tyr Thr Ser Glu Gly Val Met Thr Gly Val
        275                 280                 285

Tyr Ala Ser Lys Glu Glu Ala Lys Lys Gly Asn Lys Ile Asn Cys
290                 295                 300

Val Gly Trp Trp Phe Lys Pro Trp Phe Tyr Gln His Ala Gln Thr Ala
305                 310                 315                 320

Leu Asn Arg Gly Glu Phe Val Glu Tyr Ile Pro Thr Arg Glu Tyr Tyr
                325                 330                 335

His Arg His Thr Arg Cys Leu Tyr Trp Glu Gly Lys Leu Ile Leu Pro
            340                 345                 350

Phe Gly Asp Gln Phe Trp Phe Arg Phe Leu Leu Gly Trp Leu Met Pro
        355                 360                 365

Pro Lys Val Ser Leu Leu Lys Ala Thr Gln Gly Glu Ala Ile Arg Asn
    370                 375                 380

Tyr Tyr His Asp Asn His Val Ile Gln Asp Met Leu Val Pro Leu Tyr
385                 390                 395                 400

Lys Val Gly Asp Ala Leu Glu Phe Val His Arg Glu Met Glu Val Tyr
                405                 410                 415

Pro Leu Trp Leu Cys Pro His Arg Leu Tyr Lys Leu Pro Val Lys Thr
            420                 425                 430

Met Val Tyr Pro Glu Pro Gly Phe Glu His Gln His Arg Gln Gly Asp
        435                 440                 445

Ala Ser Tyr Ala Gln Met Phe Thr Asp Val Gly Val Tyr Ala Pro
    450                 455                 460

Gly Ala Val Leu Arg Gly Glu Phe Asn Gly Ala Glu Ala Val His
465                 470                 475                 480

Arg Leu Glu Gln Trp Leu Ile Glu Asn His Ser Tyr Gln Pro Gln Tyr
                485                 490                 495

Ala Val Ser Glu Leu Asn Glu Lys Asp Ser Trp Arg Met Phe Asp Ala
            500                 505                 510

Ser His Tyr Glu His Cys Arg Gln Lys Tyr Gly Ala Val Gly Thr Phe
        515                 520                 525

Met Ser Val Tyr Tyr Lys Ser Lys Lys Gly Arg Lys Thr Glu Lys Glu
    530                 535                 540

Val Gln Glu Ala Glu Ala Ala Ile Leu Glu Pro Ala Tyr Ala Asp Glu
545                 550                 555                 560

Glu Ala

<210> SEQ ID NO 23
<211> LENGTH: 1692
<212> TYPE: DNA
<213> ORGANISM: Zinnia elegans

<400> SEQUENCE: 23
atgtctgatc ttgaagctcc attggtccgt ccgaaaagaa agaaggtttg ggttgactat      60
tttgtccaat tcagatggat tattgtcatt tttgttgtac taccaatctc cttcactcta    120
tacttcctca cttatcttgg ggacgtcaga tcagattgga aatcatacaa caacgccaa     180 aaggaacacg aagaaaatgt caaaaaagta gtcaaacgtc ttcaagaaag aaacccatcg    240
aaagacgggc gcgtatgtac agccagaaaa ccctggattg ctgttggaat gagaaacgtt    300
gactacaaac gagcccgtca tttcgaagtt gacctgtcag ctttccggaa cattcttgaa    360
atcaatcaag aaacaatgat tgcaaaatgt gagccactgg tcaacatggg tcgaatcacc    420

```
cgagccaccg tcccattgaa tcttgcactt gctgctgttg ctgaacttga tgatctaacc      480
gttggtgggc tgatcaatgg ttatggtatt gagggtagtt ctcatctata tgggcttttt      540
tctgatactg ttgtggctta tgaaatcgtt cttgctggcg ggaaggtcgt tcgggctaca      600
aaagataatg aatactctga tcttttctat gcaattccat ggtctcaagg aactttaggg      660
ctactagtgt ctgctgaaat caaacttata ccaattaaag aatacatgaa gttaacttac      720 acaccgtta gaggtagtgt aaaagaactt ggaaaagcat atattgactc atttgctcca       780
cgattcgggg aagaaaacag tgaagaagtt cctgattttg tggaaggtat gatttacaat      840
ccccatgaag gtgtttgtat gacaggaaaa tacgcctcta agaagaagc ggagaaaaaa       900 ggaaataaga ttaatagtgt ggggtggtgg tttaaaccat ggttttatca acatgctcaa      960
accgcactta caaaaggga atttgttgag tacatcccaa ctagggaata ctatcatagg      1020
cacacacggt gtttgtattg ggaagggaag cttattctgc catttggtga tcaatggtgg     1080
tttagatttc tacttgggtg gatgatgcca ccaaaggttt ctttgctgaa agcgacacaa     1140
ggtgaagcaa ttagaaatta ttatcatgaa atgcatgtta ttcaagatat gcttgttccg     1200
ctttacaaag ttcctgatgc tttggaatgg gttgatcgtg agatggaggt atatcccta     1260 tggctttgcc cacaccgact atacaagctc cctacaaaa caatggtgta ccccgaacca     1320
ggatttgagg aacactgcag gcaaggtgac acaccctatg ctcaaatgta cagacgtt     1380 ggtgtctact atgcaccagg acccgtgtta aggggtgagg ttttttgatgg agtcgatgca     1440 gttcgtagaa tggaaagttg gttaatcgag aaccacgggt tccagccaca atacgcagtt     1500
tctgaactga acgagaagaa ttttttggagg atgtttgatg cagggcttta tgaacagtgt     1560
aggaataagt atggagctgt gggaacgttt atgagcgtgt attacaagtg taagaaaggt     1620
aagaagaccg agaaggaggt tcaggaagcc gagcaagctc aagttgaagt cccgtatgct     1680
gaaactgatt ag                                                         1692
```

<210> SEQ ID NO 24
<211> LENGTH: 563
<212> TYPE: PRT
<213> ORGANISM: Zinnia elegans

<400> SEQUENCE: 24

```
Met Ser Asp Leu Glu Ala Pro Leu Val Arg Pro Lys Arg Lys Lys Val
1               5                   10                  15

Trp Val Asp Tyr Phe Val Gln Phe Arg Trp Ile Ile Val Ile Phe Val
            20                  25                  30

Val Leu Pro Ile Ser Phe Thr Leu Tyr Phe Leu Thr Tyr Leu Gly Asp
        35                  40                  45

Val Arg Ser Asp Trp Lys Ser Tyr Lys Gln Arg Gln Lys Glu His Glu
    50                  55                  60

Glu Asn Val Lys Lys Val Val Lys Arg Leu Gln Glu Arg Asn Pro Ser
65                  70                  75                  80

Lys Asp Gly Arg Val Cys Thr Ala Arg Lys Pro Trp Ile Ala Val Gly
                85                  90                  95

Met Arg Asn Val Asp Tyr Lys Arg Ala Arg His Phe Glu Val Asp Leu
            100                 105                 110

Ser Ala Phe Arg Asn Ile Leu Glu Ile Asn Gln Glu Thr Met Ile Ala
        115                 120                 125

Lys Cys Glu Pro Leu Val Asn Met Gly Arg Ile Thr Arg Ala Thr Val
    130                 135                 140
```

-continued

```
Pro Leu Asn Leu Ala Leu Ala Val Ala Glu Leu Asp Asp Leu Thr
145                 150                 155                 160
Val Gly Gly Leu Ile Asn Gly Tyr Gly Ile Glu Gly Ser Ser His Leu
            165                 170                 175
Tyr Gly Leu Phe Ser Asp Thr Val Val Ala Tyr Glu Ile Val Leu Ala
            180                 185                 190
Gly Gly Lys Val Val Arg Ala Thr Lys Asp Asn Glu Tyr Ser Asp Leu
            195                 200                 205
Phe Tyr Ala Ile Pro Trp Ser Gln Gly Thr Leu Gly Leu Leu Val Ser
            210                 215                 220
Ala Glu Ile Lys Leu Ile Pro Ile Lys Glu Tyr Met Lys Leu Thr Tyr
225                 230                 235                 240
Thr Pro Val Arg Gly Ser Val Lys Glu Leu Gly Lys Ala Tyr Ile Asp
                245                 250                 255
Ser Phe Ala Pro Arg Phe Gly Glu Glu Asn Ser Glu Val Pro Asp
                260                 265                 270
Phe Val Glu Gly Met Ile Tyr Asn Pro His Glu Gly Val Cys Met Thr
            275                 280                 285
Gly Lys Tyr Ala Ser Lys Glu Glu Ala Glu Lys Lys Gly Asn Lys Ile
290                 295                 300
Asn Ser Val Gly Trp Trp Phe Lys Pro Trp Phe Tyr Gln His Ala Gln
305                 310                 315                 320
Thr Ala Leu Thr Lys Gly Glu Phe Val Glu Tyr Ile Pro Thr Arg Glu
                325                 330                 335
Tyr Tyr His Arg His Thr Arg Cys Leu Tyr Trp Glu Gly Lys Leu Ile
                340                 345                 350
Leu Pro Phe Gly Asp Gln Trp Trp Phe Arg Phe Leu Leu Gly Trp Met
            355                 360                 365
Met Pro Pro Lys Val Ser Leu Leu Lys Ala Thr Gln Gly Glu Ala Ile
    370                 375                 380
Arg Asn Tyr Tyr His Glu Met His Val Ile Gln Asp Met Leu Val Pro
385                 390                 395                 400
Leu Tyr Lys Val Pro Asp Ala Leu Glu Trp Val Asp Arg Glu Met Glu
                405                 410                 415
Val Tyr Pro Leu Trp Leu Cys Pro His Arg Leu Tyr Lys Leu Pro Tyr
                420                 425                 430
Lys Thr Met Val Tyr Pro Glu Pro Gly Phe Glu Glu His Cys Arg Gln
            435                 440                 445
Gly Asp Thr Pro Tyr Ala Gln Met Tyr Thr Asp Val Gly Val Tyr Tyr
    450                 455                 460
Ala Pro Gly Pro Val Leu Arg Gly Glu Val Phe Asp Gly Val Asp Ala
465                 470                 475                 480
Val Arg Arg Met Glu Ser Trp Leu Ile Glu Asn His Gly Phe Gln Pro
                485                 490                 495
Gln Tyr Ala Val Ser Glu Leu Asn Glu Lys Asn Phe Trp Arg Met Phe
            500                 505                 510
Asp Ala Gly Leu Tyr Glu Gln Cys Arg Asn Lys Tyr Gly Ala Val Gly
            515                 520                 525
Thr Phe Met Ser Val Tyr Tyr Lys Cys Lys Lys Gly Lys Lys Thr Glu
            530                 535                 540
Lys Glu Val Gln Glu Ala Glu Gln Ala Gln Val Glu Val Pro Tyr Ala
545                 550                 555                 560
Glu Thr Asp
```

<210> SEQ ID NO 25
<211> LENGTH: 1551
<212> TYPE: DNA
<213> ORGANISM: Homo sapiens

<400> SEQUENCE: 25

```
atggagcccg ccgtgtcgct ggccgtgtgc gcgctgctct tcctgctgtg ggtgcgcctg      60
aaggggctgg agttcgtgct catccaccag cgctgggtgt cgtgtgcct cttcctcctg     120
ccgctctcgc ttatcttcga tatctactac tacgtgcgcg cctgggtggt gttcaagctc     180
agcagcgctc cgcgcctgca cgagcagcgc gtgcgggaca tccagaagca ggtgcgggaa     240
tggaaggagc agggtagcaa gaccttcatg tgcacggggc gccctggctg gctcactgtc     300
tcactacgtg tcgggaagta caagaagaca cacaaaaaca tcatgatcaa cctgatggac     360
attctggaag tggacaccaa gaaacagatt gtccgtgtgg agcccttggt gaccatgggc     420
caggtgactg ccctgctgac ctccattggc tggactctcc ccgtgttgcc tgagcttgat     480
gacctcacag tggggggctt gatcatgggc acaggcatcg agtcatcatc ccacaagtac     540
ggcctgttcc aacacatctg cactgcttac gagctggtcc tggctgatgg cagctttgtg     600
cgatgcactc cgtccgaaaa ctcagacctg ttctatgccg taccctggtc ctgtgggacg     660
ctgggttttcc tggtggccgc tgagatccgc atcatccctg caagaagta cgtcaagctg     720
cgtttcgagc cagtgcgggg cctggaggct atctgtgcca agttcaccca cgagtcccag     780
cggcaggaga accacttcgt ggaagggctg ctctactccc tggatgaggc tgtcattatg     840
acagggtcga tgacagatga ggcagagccc agcaagctga atagcattgg caattactac     900
aagccgtggt tctttaagca tgtggagaac tatctgaaga caaaccgaga gggcctggag     960
tacattccct tgagacacta ctaccaccgc cacacgcgca gcatcttctg ggagctccag    1020
gacatcatcc cctttggcaa caaccccatc ttccgctacc tctttggctg gatggtgcct    1080
cccaagatct ccctcctgaa gctgacccag ggtgagaccc tgcgcaagct gtacgagcag    1140
caccacgtgg tgcaggacat gctggtgccc atgaagtgcc tgcagcaggc cctgcacacc    1200
ttccaaaacg acatccacgt ctaccccatc tggctgtgtc gttcatcct gcccagccca    1260
ccaggcctag tgcaccccaa aggaaatgag gcagagctct acatcgacat tggagcatat    1320
ggggagccgc gtgtgaaaca ctttgaagcc aggtcctgca tgaggcagct ggagaagttt    1380
gtccgcagcg tgcatggctt ccagatgctg tatgccgact gctacatgaa ccgggaggag    1440
ttctggagaga tgtttgatgg ctccttgtac cacaagctgc gagagaagct gggttgccag    1500
gacgccttcc ccgaggtgta cgacaagatc tgcaaggccg ccaggcactg a              1551
```

<210> SEQ ID NO 26
<211> LENGTH: 516
<212> TYPE: PRT
<213> ORGANISM: Homo sapiens

<400> SEQUENCE: 26

```
Met Glu Pro Ala Val Ser Leu Ala Val Cys Ala Leu Leu Phe Leu Leu
1               5                   10                  15

Trp Val Arg Leu Lys Gly Leu Glu Phe Val Leu Ile His Gln Arg Trp
            20                  25                  30

Val Phe Val Cys Leu Phe Leu Leu Pro Leu Ser Leu Ile Phe Asp Ile
        35                  40                  45

Tyr Tyr Tyr Val Arg Ala Trp Val Val Phe Lys Leu Ser Ser Ala Pro
    50                  55                  60
```

-continued

Arg Leu His Glu Gln Arg Val Arg Asp Ile Gln Lys Gln Val Arg Glu
65                  70                  75                  80

Trp Lys Glu Gln Gly Ser Lys Thr Phe Met Cys Thr Gly Arg Pro Gly
            85                  90                  95

Trp Leu Thr Val Ser Leu Arg Val Gly Lys Tyr Lys Lys Thr His Lys
        100                 105                 110

Asn Ile Met Ile Asn Leu Met Asp Ile Leu Glu Val Asp Thr Lys Lys
    115                 120                 125

Gln Ile Val Arg Val Glu Pro Leu Val Thr Met Gly Gln Val Thr Ala
130                 135                 140

Leu Leu Thr Ser Ile Gly Trp Thr Leu Pro Val Leu Pro Glu Leu Asp
145                 150                 155                 160

Asp Leu Thr Val Gly Gly Leu Ile Met Gly Thr Gly Ile Glu Ser Ser
                165                 170                 175

Ser His Lys Tyr Gly Leu Phe Gln His Ile Cys Thr Ala Tyr Glu Leu
            180                 185                 190

Val Leu Ala Asp Gly Ser Phe Val Arg Cys Thr Pro Ser Glu Asn Ser
        195                 200                 205

Asp Leu Phe Tyr Ala Val Pro Trp Ser Cys Gly Thr Leu Gly Phe Leu
210                 215                 220

Val Ala Ala Glu Ile Arg Ile Ile Pro Ala Lys Lys Tyr Val Lys Leu
225                 230                 235                 240

Arg Phe Glu Pro Val Arg Gly Leu Glu Ala Ile Cys Ala Lys Phe Thr
                245                 250                 255

His Glu Ser Gln Arg Gln Glu Asn His Phe Val Glu Gly Leu Leu Tyr
            260                 265                 270

Ser Leu Asp Glu Ala Val Ile Met Thr Gly Val Met Thr Asp Glu Ala
        275                 280                 285

Glu Pro Ser Lys Leu Asn Ser Ile Gly Asn Tyr Tyr Lys Pro Trp Phe
290                 295                 300

Phe Lys His Val Glu Asn Tyr Leu Lys Thr Asn Arg Glu Gly Leu Glu
305                 310                 315                 320

Tyr Ile Pro Leu Arg His Tyr Tyr His Arg His Thr Arg Ser Ile Phe
                325                 330                 335

Trp Glu Leu Gln Asp Ile Ile Pro Phe Gly Asn Asn Pro Ile Phe Arg
            340                 345                 350

Tyr Leu Phe Gly Trp Met Val Pro Pro Lys Ile Ser Leu Leu Lys Leu
        355                 360                 365

Thr Gln Gly Glu Thr Leu Arg Lys Leu Tyr Glu Gln His His Val Val
370                 375                 380

Gln Asp Met Leu Val Pro Met Lys Cys Leu Gln Gln Ala Leu His Thr
385                 390                 395                 400

Phe Gln Asn Asp Ile His Val Tyr Pro Ile Trp Leu Cys Pro Phe Ile
                405                 410                 415

Leu Pro Ser Gln Pro Gly Leu Val His Pro Lys Gly Asn Glu Ala Glu
            420                 425                 430

Leu Tyr Ile Asp Ile Gly Ala Tyr Gly Glu Pro Arg Val Lys His Phe
        435                 440                 445

Glu Ala Arg Ser Cys Met Arg Gln Leu Glu Lys Phe Val Arg Ser Val
450                 455                 460

His Gly Phe Gln Met Leu Tyr Ala Asp Cys Tyr Met Asn Arg Glu Glu
465                 470                 475                 480

Phe Trp Glu Met Phe Asp Gly Ser Leu Tyr His Lys Leu Arg Glu Lys
                485                 490                 495

```
Leu Gly Cys Gln Asp Ala Phe Pro Glu Val Tyr Asp Lys Ile Cys Lys
            500                 505                 510

Ala Ala Arg His
        515

<210> SEQ ID NO 27
<211> LENGTH: 1551
<212> TYPE: DNA
<213> ORGANISM: Danio rerio

<400> SEQUENCE: 27
atggatccgt tattgtattt gggagggtta gctgtgttgt ttttgatatg gatcaaagtg      60
aaaggcttgg agtacgtgat tatacaccag agatggatct tcgtgtgcct gtttctcctg     120
cccttgtccg tcgtgtttga tgtgtactat cacctgcgcg cctggatcat cttcaagatg     180
tgctccgcgc ccaaacagca cgaccagcgg gtcagagaca ttcagagaca ggtgcgagaa     240
tggaggaaag atggagggaa gaaatatatg tgcacgggac gtccgggatg gctgactgtg     300
tccctcagag tgggaaaata caagaaaact cacaagaaca tcatgattaa catgatggac     360
atcctggagg ttgacacaaa acgaaaggta gtgcgtgtgg agcctttagc taacatgggt     420
caggtgactg ctctgctcaa ctctattggc tggacactgc cggtgctgcc agaactcgat     480
gacctcactg ttggcgggct ggtgatggga acaggcattg agtcttcatc tcacatctac     540
ggcctgtttc agcacatctg tgtagccttt gagctggtgt tggctgacgg cagtctggtc     600
cgctgcactg agaaagaaaa ctctgacctg ttttatgccg ttccctggtc tgcgggact     660 ctggggtttc tggttgcggc agagatccgg ataattccag ctcagaaatg ggtgaagctg     720
cactatgaac ctgttcgcgg cttggatgca atttgcaaaa agtttgctga ggaatctgcc     780
aataaggaga ccagtttgt tgagggactt cagtactctc gggacgaggc tgtgattatg     840
accggcgtca tgacggatca tgcagagcct gacaagacta actgtatagg ttattattac     900
aagccgtggt tctttcggca tgtggagagt ttcctgaagc agaaccgcgt tgcagtggag     960
tacattcctc tccgccacta ttaccacaga cacacccgca gcatcttctg ggagttacaa    1020
gacattattc cattcgggaa taacccgttg ttccggtatg tgtttggctg gatggttcct    1080
ccaaagatct ctctgctaaa gcttactcag ggagagacca tccgcaaaact gtacgagcag    1140 caccatgtgg tgcaggacat gctggtcccc atgaaggaca tcaaggctgc catccagcgt    1200
ttccatgagg acattcatgt gtatcctctg tggctgtgtc cattcctttt gcccaaccag    1260
ccaggaatgg tgcatcctaa aggagatgaa gatgaactgt atgttgatat cggagcatat    1320
ggagaaccaa aggtcaaaca ctttgaggcc acatcatcca cacggcagct ggagaagttt    1380
gtcagagacg ttcacggatt ccagatgttg tatgctgatg tatacatgga acgcaaggaa    1440
ttctgggaga tgtttgacgg cactttgtat cacaaactca gagaggagct cggctgtaaa    1500
gatgcattcc ctgaagtctt tgacaaaatc tgcaagtctg caagacattg a             1551

<210> SEQ ID NO 28
<211> LENGTH: 516
<212> TYPE: PRT
<213> ORGANISM: Danio rerio

<400> SEQUENCE: 28

Met Asp Pro Leu Leu Tyr Leu Gly Gly Leu Ala Val Leu Phe Leu Ile
1               5                   10                  15

Trp Ile Lys Val Lys Gly Leu Glu Tyr Val Ile Ile His Gln Arg Trp
            20                  25                  30
```

```
Ile Phe Val Cys Leu Phe Leu Leu Pro Leu Ser Val Val Phe Asp Val
             35                  40                  45

Tyr Tyr His Leu Arg Ala Trp Ile Ile Phe Lys Met Cys Ser Ala Pro
 50                  55                  60

Lys Gln His Asp Gln Arg Val Arg Asp Ile Gln Arg Gln Val Arg Glu
 65                  70                  75                  80

Trp Arg Lys Asp Gly Gly Lys Lys Tyr Met Cys Thr Gly Arg Pro Gly
                 85                  90                  95

Trp Leu Thr Val Ser Leu Arg Val Gly Lys Tyr Lys Lys Thr His Lys
                100                 105                 110

Asn Ile Met Ile Asn Met Met Asp Ile Leu Glu Val Asp Thr Lys Arg
                115                 120                 125

Lys Val Val Arg Val Glu Pro Leu Ala Asn Met Gly Gln Val Thr Ala
                130                 135                 140

Leu Leu Asn Ser Ile Gly Trp Thr Leu Pro Val Leu Pro Glu Leu Asp
145                 150                 155                 160

Asp Leu Thr Val Gly Gly Leu Val Met Gly Thr Gly Ile Glu Ser Ser
                165                 170                 175

Ser His Ile Tyr Gly Leu Phe Gln His Ile Cys Val Ala Phe Glu Leu
                180                 185                 190

Val Leu Ala Asp Gly Ser Leu Val Arg Cys Thr Glu Lys Glu Asn Ser
                195                 200                 205

Asp Leu Phe Tyr Ala Val Pro Trp Ser Cys Gly Thr Leu Gly Phe Leu
                210                 215                 220

Val Ala Ala Glu Ile Arg Ile Ile Pro Ala Gln Lys Trp Val Lys Leu
225                 230                 235                 240

His Tyr Glu Pro Val Arg Gly Leu Asp Ala Ile Cys Lys Lys Phe Ala
                245                 250                 255

Glu Glu Ser Ala Asn Lys Glu Asn Gln Phe Val Glu Gly Leu Gln Tyr
                260                 265                 270

Ser Arg Asp Glu Ala Val Ile Met Thr Gly Val Met Thr Asp His Ala
                275                 280                 285

Glu Pro Asp Lys Thr Asn Cys Ile Gly Tyr Tyr Lys Pro Trp Phe
                290                 295                 300

Phe Arg His Val Glu Ser Phe Leu Lys Gln Asn Arg Val Ala Val Glu
305                 310                 315                 320

Tyr Ile Pro Leu Arg His Tyr His Arg His Thr Arg Ser Ile Phe
                325                 330                 335

Trp Glu Leu Gln Asp Ile Ile Pro Phe Gly Asn Asn Pro Leu Phe Arg
                340                 345                 350

Tyr Val Phe Gly Trp Met Val Pro Pro Lys Ile Ser Leu Leu Lys Leu
                355                 360                 365

Thr Gln Gly Glu Thr Ile Arg Lys Leu Tyr Glu Gln His His Val Val
                370                 375                 380

Gln Asp Met Leu Val Pro Met Lys Asp Ile Lys Ala Ala Ile Gln Arg
385                 390                 395                 400

Phe His Glu Asp Ile His Val Tyr Pro Leu Trp Leu Cys Pro Phe Leu
                405                 410                 415

Leu Pro Asn Gln Pro Gly Met Val His Pro Lys Gly Asp Glu Asp
                420                 425                 430

Leu Tyr Val Asp Ile Gly Ala Tyr Gly Glu Pro Lys Val Lys His Phe
                435                 440                 445

Glu Ala Thr Ser Ser Thr Arg Gln Leu Glu Lys Phe Val Arg Asp Val
```

```
                450             455             460
His Gly Phe Gln Met Leu Tyr Ala Asp Val Tyr Met Glu Arg Lys Glu
465                 470                 475                 480

Phe Trp Glu Met Phe Asp Gly Thr Leu Tyr His Lys Leu Arg Glu Glu
                485                 490                 495

Leu Gly Cys Lys Asp Ala Phe Pro Glu Val Phe Asp Lys Ile Cys Lys
                500                 505                 510

Ser Ala Arg His
        515

<210> SEQ ID NO 29
<211> LENGTH: 328
<212> TYPE: PRT
<213> ORGANISM: Saccharum officinarum
<220> FEATURE:
<221> NAME/KEY: DOMAIN
<222> LOCATION: (1)..(328)
<223> OTHER INFORMATION: substrate binding domain of SEQ ID NO: 2

<400> SEQUENCE: 29

Glu Tyr Met Lys Leu Thr Tyr Ile Pro Val Lys Gly Ser Leu Lys Glu
1               5                   10                  15

Ile Ala Gln Ala Tyr Ala Asp Ser Phe Ala Pro Arg Asp Gly Asp Pro
                20                  25                  30

Ala Lys Val Pro Asp Phe Val Glu Gly Met Val Tyr Thr Glu Ser Glu
                35                  40                  45

Gly Val Met Met Thr Gly Val Tyr Ala Ser Lys Glu Glu Ala Lys Lys
50                  55                  60

Lys Gly Asn Lys Ile Asn Cys Val Gly Trp Trp Phe Lys Pro Trp Phe
65                  70                  75                  80

Tyr Gln His Ala Gln Thr Ala Leu Lys Arg Gly Glu Phe Val Glu Tyr
                85                  90                  95

Ile Pro Thr Arg Glu Tyr Tyr His Arg His Thr Arg Cys Leu Tyr Trp
                100                 105                 110

Glu Gly Lys Leu Ile Leu Pro Phe Gly Asp Gln Phe Trp Phe Arg Phe
                115                 120                 125

Leu Leu Gly Trp Leu Met Pro Pro Lys Val Ser Leu Leu Lys Ala Thr
130                 135                 140

Gln Gly Glu Ala Ile Arg Asn Tyr Tyr His Asp Asn His Val Ile Gln
145                 150                 155                 160

Asp Met Leu Val Pro Leu Tyr Lys Val Gly Asp Ala Leu Glu Phe Val
                165                 170                 175

His Arg Glu Met Glu Val Tyr Pro Leu Trp Leu Cys Pro His Arg Leu
                180                 185                 190

Tyr Lys Leu Pro Val Lys Thr Met Val Tyr Pro Glu Pro Gly Phe Glu
                195                 200                 205

His Gln His Arg Gln Gly Asp Thr Ser Tyr Ala Gln Met Phe Thr Asp
                210                 215                 220

Val Gly Val Tyr Tyr Ala Pro Ala Ala Val Leu Arg Gly Glu Glu Phe
225                 230                 235                 240

Asn Gly Val Glu Ala Val His Arg Leu Glu Gln Trp Leu Ile Glu Asn
                245                 250                 255

His Ser Tyr Gln Pro Gln Tyr Ala Val Ser Glu Leu Asn Glu Lys Asp
                260                 265                 270

Phe Trp Arg Met Phe Asp Ala Ser His Tyr Glu His Cys Arg His Lys
                275                 280                 285
```

```
Tyr Gly Ala Val Gly Thr Phe Met Ser Val Tyr Tyr Lys Ser Lys
            290                 295                 300

Gly Arg Lys Thr Glu Lys Glu Val Gln Glu Ala Glu Ala Ala Ile Leu
305                 310                 315                 320

Glu Pro Ala Tyr Ala Asp Glu Ala
            325

<210> SEQ ID NO 30
<211> LENGTH: 54
<212> TYPE: DNA
<213> ORGANISM: Artificial sequence
<220> FEATURE:
<223> OTHER INFORMATION: primer: prm05930

<400> SEQUENCE: 30
ggggacaagt ttgtacaaaa aagcaggctt cacaatggcg gacgtgcatg aacc         54

<210> SEQ ID NO 31
<211> LENGTH: 49
<212> TYPE: DNA
<213> ORGANISM: Artificial sequence
<220> FEATURE:
<223> OTHER INFORMATION: primer: prm05931

<400> SEQUENCE: 31
ggggaccact ttgtacaaga aagctgggtt taggcctcgt ccgcgtagg              49

<210> SEQ ID NO 32
<211> LENGTH: 2193
<212> TYPE: DNA
<213> ORGANISM: Oryza sativa

<400> SEQUENCE: 32
aatccgaaaa gtttctgcac cgttttcacc ccctaactaa caatataggg aacgtgtgct    60
aaatataaaa tgagaccttà tatatgtagc gctgataact agaactatgc aagaaaaact   120
catccaccta ctttagtggc aatcgggcta ataaaaaag agtcgctaca ctagtttcgt    180
tttccttagt aattaagtgg gaaaatgaaa tcattattgc ttagaatata cgttcacatc   240
tctgtcatga agttaaatta ttcgaggtag ccataattgt catcaaactc ttcttgaata   300
aaaaaatctt tctagctgaa ctcaatgggt aaagagagag atttttttta aaaaaataga   360
atgaagatat tctgaacgta ttggcaaaga tttaaacata taattatata attttatagt   420
ttgtgcattc gtcatatcgc acatcattaa ggacatgtct tactccatcc caattttat    480 ttagtaatta aagacaattg acttatttt attatttatc tttttcgat tagatgcaag     540 gtacttacgc acacactttg tgctcatgtg catgtgtgag tgcacctcct caatacgt     600 tcaactagca acacatctct aatatcactc gcctatttaa tacatttagg tagcaatatc   660
tgaattcaag cactccacca tcaccagacc actttttaata atatctaaaa tacaaaaaat  720
aattttacag aatagcatga aaagtatgaa acgaactatt taggtttttc acatacaaaa   780
aaaaaaagaa ttttgctcgt gcgcgagcgc caatctccca tattgggcac acaggcaaca   840
acagagtggc tgcccacaga acaacccaca aaaacgatg atctaacgga ggacagcaag    900
tccgcaacaa cctttaaca gcaggctttg cggccaggag agaggaggag aggcaaagaa   960
aaccaagcat cctcctcctc ccatctataa attcctcccc ccttttcccc tctctatata  1020
ggaggcatcc aagccaagaa gagggagagc accaaggaca cgcgactagc agaagccgag  1080
cgaccgcctt cttcgatcca tatcttccgg tcgagttctt ggtcgatctc ttccctcctc  1140
cacctcctcc tcacagggta tgtgcccttc ggttgttctt ggatttattg ttctaggttg  1200
```

```
tgtagtacgg gcgttgatgt taggaaaggg gatctgtatc tgtgatgatt cctgttcttg    1260
gatttgggat agaggggttc ttgatgttgc atgttatcgg ttcggtttga ttagtagtat    1320
ggttttcaat cgtctggaga gctctatgga aatgaaatgg tttagggtac ggaatcttgc    1380
gattttgtga gtacctttg tttgaggtaa atcagagca ccggtgattt tgcttggtgt      1440
aataaaagta cggttgtttg gtcctcgatt ctggtagtga tgcttctcga tttgacgaag    1500
ctatcctttg tttattccct attgaacaaa aataatccaa ctttgaagac ggtcccgttg    1560
atgagattga atgattgatt cttaagcctg tccaaaattt cgcagctggc ttgtttagat    1620
acagtagtcc ccatcacgaa attcatgaaa acagttataa tcctcaggaa caggggattc    1680
cctgttcttc cgatttgctt tagtcccaga atttttttc ccaaatatct taaaaagtca     1740
ctttctggtt cagttcaatg aattgattgc tacaaataat gcttttatag cgttatccta    1800
gctgtagttc agttaatagg taataccct atagtttagt caggagaaga acttatccga     1860
tttctgatct ccattttaa ttatatgaaa tgaactgtag cataagcagt attcatttgg     1920
attatttttt ttattagctc tcacccctc attattctga gctgaaagtc tggcatgaac     1980
tgtcctcaat tttgttttca aattcacatc gattatctat gcattatcct cttgtatcta    2040
cctgtagaag tttcttttg gttattcctt gactgcttga ttacagaaag aaatttatga     2100
agctgtaatc gggatagtta tactgcttgt tcttatgatt catttccttt gtgcagttct    2160
tggtgtagct tgccactttc accagcaaag ttc                                 2193

<210> SEQ ID NO 33
<211> LENGTH: 1686
<212> TYPE: DNA
<213> ORGANISM: Saccharum officinarum

<400> SEQUENCE: 33
atggcggacg tgcatgaacc tttggtgcgc cgcaagagga agaaggtttt ggtggactac      60
ttcgtgcagt tccgatggat cctcgtgatc ttcgtggtcc ttcctatttc atctctgatc     120
tacttcaata tctttctggg cgacatgtgg tctgccatga agtcagagaa gaagcgccag     180
aagcaacacg atgagaatgt gcagaaggtt gtgaagcggc tcaagcagag gaacccaaag     240
aaggatggtc ttgtttgcac agccaggaag ccctggattg ctgttggcat gcgcaatgtg     300
gactacaagc gtgcgaggca ttttgaggtt gaccttctt ccttcaggaa catccttgag      360
attgacaaag agaggatggt tgccaaggtt gagccccttg taaacatggg tcagataacc     420
agagctacct gcccaatgaa ccttgccctt gcagtcgtcg ctgagcttga cgacctcact    480
gttggtgggc tgatcaatgg ttatggaatt gaggggagct ctcacctcta tggccttttc    540
tctgacacgg ttgttgcaat ggaagttgtt cttgcagatg gccgggttgt tagggccacc    600
aaggataatg agtactctga cctttttctat ggcattccct ggtcccaggg aacacttggg   660
ttccttgtct ctgctgagat caagctgatt cccatcaagg agtacatgaa gctcacctac   720
attccagtga aagggagtct gaaggaaatc gcgcaggcct atgctgattc tttcgcgcca   780
agagatggtg acccagcaaa ggtccctgac tttgttgaag gaatggtgta cacagaaagc   840
gagggtgtca tgatgactgg tgtgtatgct tcgaaagaag aggcgaagaa gaagggcaac   900
aagatcaact gcgtggggtg gtggtttaag ccctggttct accagcatgc tcagacagcg   960
ctcaagaggg gcgagtttgt ggagtacatc ccaacaagag agtactacca ccgccacacc  1020
cggtgcctgt actggagggg aaagctgatc ctgccattcg gtgaccagtt ctggttcagg  1080
ttcctgctgg gttggctcat gccaccaaag gtgtctcttc tgaaggcgac tcagggtgag  1140
```

-continued

```
gctatcagga actactacca tgacaaccat gtgatccagg acatgctggt gccgctgtac    1200
aaggttggag atgctctcga gttcgtgcac cgcgagatgg aggtgtatcc tctgtggctg    1260
tgccctcacc gcctgtacaa gctgcccgtg aagacaatgg tgtaccctga gcctgggttc    1320
gagcaccagc acaggcaggg cgacacaagc tacgcacaga tgttcacgga cgtgggcgtg    1380
tactacgctc ctgctgcggt cctaagggga gaggagttca atggcgtgga ggcggtgcac    1440
aggctggagc agtggctgat cgagaaccac agctaccagc acagtacgc ggtgtcggag     1500 ctgaatgaga aggacttctg gcacatgttc gacgcgtccc actacgagca ctgccggcac    1560
aagtatgggg cggtgggcac gttcatgagc gtgtactaca agtcgaagaa ggggcgcaag    1620
acggagaagg aggtgcagga ggcggaggcg gccatcctgg agccggccta cgcggacgag    1680
gcctaa                                                                1686
```

<210> SEQ ID NO 34
<211> LENGTH: 561
<212> TYPE: PRT
<213> ORGANISM: Saccharum officinarum

<400> SEQUENCE: 34

```
Met Ala Asp Val His Glu Pro Leu Val Arg Arg Lys Arg Lys Lys Val
1               5                   10                  15

Leu Val Asp Tyr Phe Val Gln Phe Arg Trp Ile Leu Val Ile Phe Val
            20                  25                  30

Val Leu Pro Ile Ser Ser Leu Ile Tyr Phe Asn Ile Phe Leu Gly Asp
        35                  40                  45

Met Trp Ser Ala Met Lys Ser Glu Lys Lys Arg Gln Lys Gln His Asp
    50                  55                  60

Glu Asn Val Gln Lys Val Val Lys Arg Leu Lys Gln Arg Asn Pro Lys
65                  70                  75                  80

Lys Asp Gly Leu Val Cys Thr Ala Arg Lys Pro Trp Ile Ala Val Gly
                85                  90                  95

Met Arg Asn Val Asp Tyr Lys Arg Ala Arg His Phe Glu Val Asp Leu
            100                 105                 110

Ser Ser Phe Arg Asn Ile Leu Glu Ile Asp Lys Glu Arg Met Val Ala
        115                 120                 125

Lys Val Glu Pro Leu Val Asn Met Gly Gln Ile Thr Arg Ala Thr Cys
    130                 135                 140

Pro Met Asn Leu Ala Leu Ala Val Val Ala Glu Leu Asp Asp Leu Thr
145                 150                 155                 160

Val Gly Gly Leu Ile Asn Gly Tyr Gly Ile Glu Gly Ser Ser His Leu
                165                 170                 175

Tyr Gly Leu Phe Ser Asp Thr Val Val Ala Met Glu Val Val Leu Ala
            180                 185                 190

Asp Gly Arg Val Val Arg Ala Thr Lys Asp Asn Glu Tyr Ser Asp Leu
        195                 200                 205

Phe Tyr Gly Ile Pro Trp Ser Gln Gly Thr Leu Gly Phe Leu Val Ser
    210                 215                 220

Ala Glu Ile Lys Leu Ile Pro Ile Lys Glu Tyr Met Lys Leu Thr Tyr
225                 230                 235                 240

Ile Pro Val Lys Gly Ser Leu Lys Glu Ile Ala Gln Ala Tyr Ala Asp
                245                 250                 255

Ser Phe Ala Pro Arg Asp Gly Asp Pro Ala Lys Val Pro Asp Phe Val
            260                 265                 270
```

Glu Gly Met Val Tyr Thr Glu Ser Glu Gly Val Met Met Thr Gly Val
            275                 280                 285

Tyr Ala Ser Lys Glu Glu Ala Lys Lys Lys Gly Asn Lys Ile Asn Cys
290                 295                 300

Val Gly Trp Trp Phe Lys Pro Trp Phe Tyr Gln His Ala Gln Thr Ala
305                 310                 315                 320

Leu Lys Arg Gly Glu Phe Val Glu Tyr Ile Pro Thr Arg Glu Tyr Tyr
            325                 330                 335

His Arg His Thr Arg Cys Leu Tyr Trp Gly Lys Leu Ile Leu Pro
                340                 345                 350

Phe Gly Asp Gln Phe Trp Phe Arg Phe Leu Leu Gly Trp Leu Met Pro
            355                 360                 365

Pro Lys Val Ser Leu Leu Lys Ala Thr Gln Gly Glu Ala Ile Arg Asn
370                 375                 380

Tyr Tyr His Asp Asn His Val Ile Gln Asp Met Leu Val Pro Leu Tyr
385                 390                 395                 400

Lys Val Gly Asp Ala Leu Glu Phe Val His Arg Glu Met Glu Val Tyr
            405                 410                 415

Pro Leu Trp Leu Cys Pro His Arg Leu Tyr Lys Leu Pro Val Lys Thr
            420                 425                 430

Met Val Tyr Pro Glu Pro Gly Phe Glu His Gln His Arg Gln Gly Asp
            435                 440                 445

Thr Ser Tyr Ala Gln Met Phe Thr Asp Val Gly Val Tyr Tyr Ala Pro
450                 455                 460

Ala Ala Val Leu Arg Gly Glu Glu Phe Asn Gly Val Glu Ala Val His
465                 470                 475                 480

Arg Leu Glu Gln Trp Leu Ile Glu Asn His Ser Tyr Gln Pro Gln Tyr
            485                 490                 495

Ala Val Ser Glu Leu Asn Glu Lys Asp Phe Trp His Met Phe Asp Ala
            500                 505                 510

Ser His Tyr Glu His Cys Arg His Lys Tyr Gly Ala Val Gly Thr Phe
            515                 520                 525

Met Ser Val Tyr Tyr Lys Ser Lys Gly Arg Lys Thr Glu Lys Glu
530                 535                 540

Val Gln Glu Ala Glu Ala Ala Ile Leu Glu Pro Ala Tyr Ala Asp Glu
545                 550                 555                 560

Ala

<210> SEQ ID NO 35
<211> LENGTH: 1686
<212> TYPE: DNA
<213> ORGANISM: Sorghum bicolor

<400> SEQUENCE: 35

```
atggcggacg tgcatgaacc tttggtgcgc cgcaagagga agaaggtttt ggtggactac      60
ttggtgcagt tccgatggat ccttgtgatc ttcgtggtcc ttcctatttc atctctgatc     120
tacttcaata tctttctggg cgacatgtgg tctgccatga agtcagagaa gaagcgccag     180
aagcaacacg atgagaatgt gcagaaggtt gtgaagcggc tcaagcagag gaatccaaag     240
aaggatggtc ttgtttgcac agccaggaag ccctggattg ctgttggcat gcgcaatgtg     300
gactacaagc gtgcgaggca tttcgaggtt gacctttctt ccttcaggaa catccttgag     360
attgacaaag agaggatggt tgccaaggtt gagccccttg taaacatggg tcagataacc     420
agagctacct gcccaatgaa ccttgccctt gcagttgtcg ctgagcttga cgacctcact     480
```

```
gttggtgggc tgatcaatgg ttatggaatt gaggggagct ctcacctata tggccttttc    540
tctgacacag ttgtcgcaat ggaagttgtt cttgcagatg gccgggtcgt tagagccacc    600
aaggataacg agtactctga cctattctat ggcattccct ggtcccaggg aacacttggg    660
ttccttgtct ctgctgagat caagctgatt cccatcaagg agtacatgaa gctcacctac    720
attccagtga aggggagtct gaaggaaatc gcgcaggcat atgctgattc tttcgcgcca    780
agagatggtg acccagcaaa ggtccctgac tttgttgaag aatggtgta cacagaaagc    840 gagggtgtca tgatgactgg tgtgtatgct tcgaaagaag aggcgaagaa aagggcaac    900 aagatcaact gtgtggggtg gtggtttaag ccctggttct accagcatgc tcagacggca    960
cttaagaggg gcgagtttgt ggagtacgtc ccaacaagag aatactacca tcgccacacc   1020
cggtgcctgt actgggaggg gaagctgatc ctgccattcg gtgaccagtt ctggttcagg   1080
ttcctgctgg gttggctcat gccaccaaag gtgtctctgc tgaaggcgac tcagggtgag   1140
gctatcagga actactacca tgacaaccat gtgatccagg acatgctggt gccactgtac   1200
aaggttggag atgctcttga gtttgtgcat cgcgagatgg aggtgtatcc tctgtggctg   1260
tgccctcacc gcctgtacaa gctgcccgtg aagacgatgg tgtaccctga gcctgggttc   1320
gagcaccagc acaggcaggg cgacacaagc tacgcacaga tgttcacaga tgtgggcgtg   1380
tactacgccc ctggtgcagt cctaagggga gaggagttca acggcgcgga ggcggtgcac   1440
aggctggagc agtggctgat cgagaaccac agctaccagc cacagtacgc ggtgtctgag   1500
ctgaacgaga aggacttctg cgcatgtttt gacgcgtccc actacgagca ctgccgccac   1560
aaatacgggg cggtgggcac gttcatgagc gtgtactaca agtcgaagaa ggggcgcaag   1620
acggagaagg aggtgcagga ggcggaggcg gccatcctgg agccggccta cgcggacgag   1680
gcctaa                                                              1686

<210> SEQ ID NO 36
<211> LENGTH: 561
<212> TYPE: PRT
<213> ORGANISM: Sorghum bicolor

<400> SEQUENCE: 36

Met Ala Asp Val His Glu Pro Leu Val Arg Arg Lys Arg Lys Lys Val
1               5                   10                  15

Leu Val Asp Tyr Leu Val Gln Phe Arg Trp Ile Leu Val Ile Phe Val
                20                  25                  30

Val Leu Pro Ile Ser Ser Leu Ile Tyr Phe Asn Ile Phe Leu Gly Asp
            35                  40                  45

Met Trp Ser Ala Met Lys Ser Glu Lys Lys Arg Gln Lys Gln His Asp
        50                  55                  60

Glu Asn Val Gln Lys Val Val Lys Arg Leu Lys Gln Arg Asn Pro Lys
65                  70                  75                  80

Lys Asp Gly Leu Val Cys Thr Ala Arg Lys Pro Trp Ile Ala Val Gly
                85                  90                  95

Met Arg Asn Val Asp Tyr Lys Arg Ala Arg His Phe Glu Val Asp Leu
                100                 105                 110

Ser Ser Phe Arg Asn Ile Leu Glu Ile Asp Lys Glu Arg Met Val Ala
            115                 120                 125

Lys Val Glu Pro Leu Val Asn Met Gly Gln Ile Thr Arg Ala Thr Cys
        130                 135                 140

Pro Met Asn Leu Ala Leu Ala Val Val Ala Glu Leu Asp Asp Leu Thr
145                 150                 155                 160
```

```
Val Gly Gly Leu Ile Asn Gly Tyr Gly Ile Glu Gly Ser Ser His Leu
                165                 170                 175

Tyr Gly Leu Phe Ser Asp Thr Val Val Ala Met Glu Val Val Leu Ala
            180                 185                 190

Asp Gly Arg Val Val Arg Ala Thr Lys Asp Asn Glu Tyr Ser Asp Leu
        195                 200                 205

Phe Tyr Gly Ile Pro Trp Ser Gln Gly Thr Leu Gly Phe Leu Val Ser
    210                 215                 220

Ala Glu Ile Lys Leu Ile Pro Ile Lys Glu Tyr Met Lys Leu Thr Tyr
225                 230                 235                 240

Ile Pro Val Lys Gly Ser Leu Lys Glu Ile Ala Gln Ala Tyr Ala Asp
                245                 250                 255

Ser Phe Ala Pro Arg Asp Gly Asp Pro Ala Lys Val Pro Asp Phe Val
            260                 265                 270

Glu Gly Met Val Tyr Thr Glu Ser Glu Gly Val Met Met Thr Gly Val
        275                 280                 285

Tyr Ala Ser Lys Glu Glu Ala Lys Lys Lys Gly Asn Lys Ile Asn Cys
    290                 295                 300

Val Gly Trp Trp Phe Lys Pro Trp Phe Tyr Gln His Ala Gln Thr Ala
305                 310                 315                 320

Leu Lys Arg Gly Glu Phe Val Glu Tyr Val Pro Thr Arg Glu Tyr Tyr
                325                 330                 335

His Arg His Thr Arg Cys Leu Tyr Trp Glu Gly Lys Leu Ile Leu Pro
            340                 345                 350

Phe Gly Asp Gln Phe Trp Phe Arg Phe Leu Leu Gly Trp Leu Met Pro
        355                 360                 365

Pro Lys Val Ser Leu Leu Lys Ala Thr Gln Gly Glu Ala Ile Arg Asn
    370                 375                 380

Tyr Tyr His Asp Asn His Val Ile Gln Asp Met Leu Val Pro Leu Tyr
385                 390                 395                 400

Lys Val Gly Asp Ala Leu Glu Phe Val His Arg Glu Met Glu Val Tyr
                405                 410                 415

Pro Leu Trp Leu Cys Pro His Arg Leu Tyr Lys Leu Pro Val Lys Thr
            420                 425                 430

Met Val Tyr Pro Glu Pro Gly Phe Glu His Gln His Arg Gln Gly Asp
        435                 440                 445

Thr Ser Tyr Ala Gln Met Phe Thr Asp Val Gly Val Tyr Tyr Ala Pro
    450                 455                 460

Gly Ala Val Leu Arg Gly Glu Glu Phe Asn Gly Ala Glu Ala Val His
465                 470                 475                 480

Arg Leu Glu Gln Trp Leu Ile Glu Asn His Ser Tyr Gln Pro Gln Tyr
                485                 490                 495

Ala Val Ser Glu Leu Asn Glu Lys Asp Phe Trp Arg Met Phe Asp Ala
            500                 505                 510

Ser His Tyr Glu His Cys Arg His Lys Tyr Gly Ala Val Gly Thr Phe
        515                 520                 525

Met Ser Val Tyr Tyr Lys Ser Lys Gly Arg Lys Thr Glu Lys Glu
    530                 535                 540

Val Gln Glu Ala Glu Ala Ala Ile Leu Glu Pro Ala Tyr Ala Asp Glu
545                 550                 555                 560

Ala

<210> SEQ ID NO 37
<211> LENGTH: 1692
```

```
<212> TYPE: DNA
<213> ORGANISM: Vitis vinifera

<400> SEQUENCE: 37
atgtcggatc ttcaggctcc cttgcgtccc aagaggaaaa aaatttgggt ggactatttt      60
gttcacttcc gatggattat tgtcattttt gttgtccttc ctatctcctt cactttgtac     120
ttcctcacat atcttggaga tgtcagatct gaatcraaat cttcaagca gcgtcaggag      180 gaacataatg aaaatgtcaa aaaagtcata aaacgtctca agagaggaa yccatcaagg      240 gatggccttg tctgcacagc ccggaaacca tggattgctg ttggaatgag aaatgttgac     300
tataagcggg ctcggcattt tgaagttgat cttcagctt tcagaaatat cctggacatt      360
gacaaagaga gaatgattgc cagatgtgaa ccctagtca acatgggca gattagcagg       420 gttagtgtcc caatgaatct tgcccttgct gtggttgctg agcttgatga tcttacagtt     480
ggtggcctca tcaatggcta tggaattgaa ggaagctctc acatttatgg cctattctct     540
gacactgttg tggcttatga aatcattttg gctgatgggc ggctagttag agctaccaaa    600
gacaatgagt actctgatct tttctatgct attccatggt ctcaggaac actggggctt      660 cttgttgccg ctgagatcaa gcttataccc attaaggaat acatgaagtt gacttacaaa    720
ccagtagtgg gaaatctgaa agaccttgcr cagggttatt tggattcttt tgctcccaga   780
gacggagatc aggataatcm tgagaaggtt ccagactttg tagaaaccat gatttacaat     840
cctactgaag ctgtgtgtat gacagggaga tatgcctcaa agaagaggc taagaagaaa     900 ggaaatgtga ttaacagtgt tgggtggtgg tacaagccct ggttctatca acatgcacag    960
acagccctaa agaaggggga gtttgtggag tacatcccaa ccagggaata ttaccatagg   1020
cacactaggt gtctgtattg ggagggaaaa cttattcttc catttgcaga tcaatggtgg    1080
tttaggtttt tgtttgggtg gttgatgcca ccaaaggttt ctctcctcaa ggctactcaa    1140
ggtgaagcta tcagaaacta ttaccatgag atgcatgtaa ttcaggacat gcttgttccg    1200
ctgtacaaag ttggggatgc tctagaatgg gtacatcatg agatggaggt atacccaatt    1260
tggctctgcc cacaccgatt gtacaagctt cctgtcaaaa caatgatata tcctgaacca    1320
ggctttgagc tgcatcgcag acagggtgac acacattatg cccagatgta cacagatgtg    1380
ggggtgtact atgcgccagg gcctgtcttg aggggtgagc agtttgatgg tgcagaagca    1440
gttcgccgaa tggagaactg gttgattgaa aaccatggat tccagccaca atatgcagtg    1500
tctgagctga ctgaaaagaa cttctggagg atgtttgatg ctgggcttta tgagcactgc    1560
agaaagaagt atggagcagt ggggacttttt atgagtgttt actacaaatg caagaagggg    1620
aagaagaccg agaaggaagt gcaggaggcg gagcaagcac aacttgagac accttatgct   1680
gaggctgatt ga                                                        1692

<210> SEQ ID NO 38
<211> LENGTH: 563
<212> TYPE: PRT
<213> ORGANISM: Vitis vinifera
<220> FEATURE:
<221> NAME/KEY: UNSURE
<222> LOCATION: (267)..(267)
<223> OTHER INFORMATION: Xaa can be any naturally occurring amino acid

<400> SEQUENCE: 38

Met Ser Asp Leu Gln Ala Pro Leu Arg Pro Lys Arg Lys Lys Ile Trp
1               5                   10                  15

Val Asp Tyr Phe Val His Phe Arg Trp Ile Ile Val Ile Phe Val Val
            20                  25                  30
```

```
Leu Pro Ile Ser Phe Thr Leu Tyr Phe Leu Thr Tyr Leu Gly Asp Val
            35                  40                  45

Arg Ser Glu Ser Lys Ser Phe Lys Gln Arg Gln Glu His Asn Glu
 50                  55                  60

Asn Val Lys Lys Val Ile Lys Arg Leu Lys Glu Arg Asn Pro Ser Arg
 65                  70                  75                  80

Asp Gly Leu Val Cys Thr Ala Arg Lys Pro Trp Ile Ala Val Gly Met
                85                  90                  95

Arg Asn Val Asp Tyr Lys Arg Ala Arg His Phe Glu Val Asp Leu Ser
                100                 105                 110

Ala Phe Arg Asn Ile Leu Asp Ile Asp Lys Glu Arg Met Ile Ala Arg
            115                 120                 125

Cys Glu Pro Leu Val Asn Met Gly Gln Ile Ser Arg Val Ser Val Pro
            130                 135                 140

Met Asn Leu Ala Leu Ala Val Ala Glu Leu Asp Asp Leu Thr Val
145                 150                 155                 160

Gly Gly Leu Ile Asn Gly Tyr Gly Ile Glu Gly Ser Ser His Ile Tyr
                165                 170                 175

Gly Leu Phe Ser Asp Thr Val Val Ala Tyr Glu Ile Ile Leu Ala Asp
            180                 185                 190

Gly Arg Leu Val Arg Ala Thr Lys Asp Asn Glu Tyr Ser Asp Leu Phe
            195                 200                 205

Tyr Ala Ile Pro Trp Ser Gln Gly Thr Leu Gly Leu Leu Val Ala Ala
            210                 215                 220

Glu Ile Lys Leu Ile Pro Ile Lys Glu Tyr Met Lys Leu Thr Tyr Lys
225                 230                 235                 240

Pro Val Val Gly Asn Leu Lys Asp Leu Ala Gln Gly Tyr Leu Asp Ser
                245                 250                 255

Phe Ala Pro Arg Asp Gly Asp Gln Asp Asn Xaa Glu Lys Val Pro Asp
            260                 265                 270

Phe Val Glu Thr Met Ile Tyr Asn Pro Thr Glu Ala Val Cys Met Thr
            275                 280                 285

Gly Arg Tyr Ala Ser Lys Glu Ala Lys Lys Gly Asn Val Ile
            290                 295                 300

Asn Ser Val Gly Trp Trp Tyr Lys Pro Trp Phe Tyr Gln His Ala Gln
305                 310                 315                 320

Thr Ala Leu Lys Lys Gly Glu Phe Val Glu Tyr Ile Pro Thr Arg Glu
            325                 330                 335

Tyr Tyr His Arg His Thr Arg Cys Leu Tyr Trp Gly Lys Leu Ile
            340                 345                 350

Leu Pro Phe Ala Asp Gln Trp Trp Phe Arg Phe Leu Phe Gly Trp Leu
            355                 360                 365

Met Pro Pro Lys Val Ser Leu Leu Lys Ala Thr Gln Gly Glu Ala Ile
370                 375                 380

Arg Asn Tyr Tyr His Glu Met His Val Ile Gln Asp Met Leu Val Pro
385                 390                 395                 400

Leu Tyr Lys Val Gly Asp Ala Leu Glu Trp Val His Glu Met Glu
            405                 410                 415

Val Tyr Pro Ile Trp Leu Cys Pro His Arg Leu Tyr Lys Leu Pro Val
            420                 425                 430

Lys Thr Met Ile Tyr Pro Glu Pro Gly Phe Glu Leu His Arg Arg Gln
            435                 440                 445

Gly Asp Thr His Tyr Ala Gln Met Tyr Thr Asp Val Gly Val Tyr Tyr
```

```
                450            455            460
Ala Pro Gly Pro Val Leu Arg Gly Glu Gln Phe Asp Gly Ala Glu Ala
465                 470                 475                 480

Val Arg Arg Met Glu Asn Trp Leu Ile Glu Asn His Gly Phe Gln Pro
                485                 490                 495

Gln Tyr Ala Val Ser Glu Leu Thr Glu Lys Asn Phe Trp Arg Met Phe
            500                 505                 510

Asp Ala Gly Leu Tyr Glu His Cys Arg Lys Tyr Gly Ala Val Gly
                515                 520                 525

Thr Phe Met Ser Val Tyr Tyr Lys Cys Lys Lys Gly Lys Lys Thr Glu
530                 535                 540

Lys Glu Val Gln Glu Ala Glu Gln Ala Gln Leu Glu Thr Pro Tyr Ala
545                 550                 555                 560

Glu Ala Asp

<210> SEQ ID NO 39
<211> LENGTH: 2194
<212> TYPE: DNA
<213> ORGANISM: Oryza sativa

<400> SEQUENCE: 39
aatccgaaaa gtttctgcac cgttttcacc ccctaactaa caatataggg aacgtgtgct      60
aaatataaaa tgagaccttta tatatgtagc gctgataact agaactatgc aagaaaaact    120
catccaccta ctttagtggc aatcgggcta aataaaaaag agtcgctaca ctagtttcgt    180
tttccttagt aattaagtgg gaaaatgaaa tcattattgc ttagaatata cgttcacatc    240
tctgtcatga agttaaatta ttcgaggtag ccataattgt catcaaactc ttcttgaata    300
aaaaaatctt tctagctgaa ctcaatgggt aaagagagag atttttttta aaaaaataga    360
atgaagatat tctgaacgta ttggcaaaga tttaaacata taattatata attttatagt    420
ttgtgcattc gtcatatcgc acatcattaa ggacatgtct tactccatcc caattttttat   480 ttagtaatta aagacaattg acttattttt attatttatc ttttttcgat tagatgcaag    540
gtacttacgc acacactttg tgctcatgtg catgtgtgag tgcacctcct caatacacgt    600
tcaactagca acacatctct aatatcactc gcctatttaa tacatttagg tagcaatatc    660
tgaattcaag cactccacca tcaccagacc acttttaata atatctaaaa tacaaaaaat    720
aattttacag aatagcatga aaagtatgaa acgaactatt taggttttttc acatacaaaa   780 aaaaaaagaa ttttgctcgt gcgcgagcgc caatctccca tattgggcac acaggcaaca    840
acagagtggc tgcccacaga caacccaca aaaaacgatg atctaacgga ggacagcaag     900
tccgcaacaa ccttttaaca gcaggctttg cggccaggag agaggaggag aggcaaagaa    960
aaccaagcat cctccttctc ccatctataa attcctcccc cctttccccc tctctatata   1020
ggaggcatcc aagccaagaa gagggagagc accaaggaca cgcgactagc agaagccgag   1080
cgaccgcctt ctcgatccat atcttccggt cgagttcttg gtcgatctct tccctcctcc   1140
acctcctcct cacagggtat gtgcctccct tcggttgttc ttggatttat tgttctaggt   1200
tgtgtagtac gggcgttgat gttaggaaag gggatctgta tctgtgatga ttcctgttct   1260
tggatttggg atagagggt tcttgatgtt gcatgttatc ggtcggttt gattagtagt     1320 atggttttca atcgtctgga gagctctatg gaaatgaaat ggtttaggga tcggaatctt   1380
gcgattttgt gagtaccttt tgtttgaggt aaaatcagag caccggtgat tttgcttggt   1440
gtaataaagt acggttgttt ggtcctcgat tctggtagtg atgcttctcg atttgacgaa   1500
```

```
gctatcctttt gtttattccc tattgaacaa aaataatcca actttgaaga cggtcccgtt    1560
gatgagattg aatgattgat tcttaagcct gtccaaaatt tcgcagctgg cttgtttaga    1620
tacagtagtc cccatcacga aattcatgga aacagttata atcctcagga acagggatt    1680 ccctgttctt ccgatttgct ttagtcccag aattttttt cccaaatatc ttaaaaagtc    1740
actttctggt tcagttcaat gaattgattg ctacaaataa tgcttttata gcgttatcct    1800
agctgtagtt cagttaatag gtaataccc tatagtttag tcaggagaag aacttatccg    1860
atttctgatc tccattttta attatatgaa atgaactgta gcataagcag tattcatttg    1920 gattatttt tttattagct ctcaccctt cattattctg agctgaaagt ctggcatgaa    1980
ctgtcctcaa ttttgttttc aaattcacat cgattatcta tgcattatcc tcttgtatct    2040
acctgtagaa gtttcttttt ggttattcct tgactgcttg attacagaaa gaaatttatg    2100
aagctgtaat cgggatagtt atactgcttg ttcttatgat tcatttcctt tgtgcagttc    2160
ttggtgtagc ttgccactt caccagcaaa gttc                                 2194
```

PLANTS HAVING ENHANCED YIELD-RELATED TRAITS AND A METHOD FOR MAKING THE SAME

RELATED APPLICATIONS

This application is a national stage application (under 35 U.S.C. §371) of PCT/EP2008/051154, filed Jan. 30, 2008, which claims benefit of European application 07101436.9, filed Jan. 30, 2007 and U.S. Provisional Application 60/890, 845 filed on Feb. 21, 2007.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_14546_00050_US. The size of the text tile is 127 KB, and the text file was created on Jul. 14, 2009.

The present invention relates generally to the field of molecular biology and concerns a method for enhancing various economically important yield-related traits in plants. More specifically, the present invention concerns a method for increasing seed yield in plants by increasing expression in a plant of a nucleic acid sequence encoding a Dwarf1 (DWF1) polypeptide. The present invention also concerns plants having increased expression of a nucleic acid sequence encoding a DWF1 polypeptide, which plants have increased seed yield relative to control plants. The invention also provides constructs useful in performing the methods of the invention.

The ever-increasing world population and the dwindling supply of arable land available for agriculture fuels research towards increasing the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

A trait of particular economic interest is increased yield. Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance and early vigour may also be important factors in determining yield. Optimizing the above-mentioned factors may therefore contribute to increasing crop yield.

Seed yield is a particularly important trait, since the seeds of many plants are important for human and animal nutrition. Crops such as, corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain.

The ability to increase plant yield would have many applications in areas such as agriculture, including in the production of ornamental plants, arboriculture, horticulture and forestry. Increasing yield may also find use in the production of algae for use in bioreactors (for the biotechnological production of substances such as pharmaceuticals, antibodies or vaccines, or for the bioconversion of organic waste) and other such areas.

BACKGROUND

The present invention concerns a method for increasing seed yield in plants relative to control plants by increasing expression in a plant of a nucleic acid sequence encoding a Dwarf1 (DWF1) polypeptide.

Brassinosteroids (BRs) are a class of plant hormones that are important for promoting plant growth, division and development. The term BR collectively refers to more than forty naturally occurring poly-hydroxylated sterol derivatives, with structural similarity to animal (essentially cholesterol) and fungal (essentially ergosterol) steroid hormones. Among the plant BRs, brassinolide has been shown to be the most biologically active (for review, Clouse (2002) Brassinosteroids In The Arabidopsis Book: 1-23).

The BR biosynthetic pathway has been elucidated using biochemical and mutational analyses. BRs are synthesized via at least two branched biochemical pathways starting from the same initial precursor, cycloartenol (Klahre et al. (1998) Plant Cell 10: 1677-1690). The Arabidopsis Dwarf1 protein (DWF1; also called DIM for Diminuto, or CBB1 for Cabbage1) is involved in the conversion of an early precursor of BRs, 24-methylenecholesterol, to campesterol, as well as the conversion of isofucosterol to sitosterol, using flavin adenine dinucleotide (FAD) as a co-factor. This conversion proceeds in two sequential steps: an isomerization step (of the $\Delta^{24(28)}$ bond into a $\Delta^{24(25)}$ bond) and a subsequent reduction step of the new double bond.

Transgenic Arabidopsis plants that overexpress DWF1 did not display any clearly visible phenotype (Klahre et al. (1998), supra). Transgenic rice constitutively overexpressing the rice DWF1 orthologue have been produced, and typically display increased plant height, increased internode length, and increased number of spikelets per panicle (Hong et al., (2005) Plant Cell 17:2243-2254). Japanese patent application JP1999290082 describes a nucleic acid sequence encoding the rice DWF1 orthologue and its potential use to produce dwarfed plants upon reduced expression of the nucleic acid sequence.

Surprisingly, it has now been found that increasing expression in a plant of a nucleic acid sequence encoding a DWF1 polypeptide gives plants having increased seed yield relative to control plants.

Definitions

Polypeptide(s)/Protein(s)

The terms "polypeptide" and "protein" are used interchangeably herein and refer to amino acids in a polymeric form of any length.

Polynucleotide(s)/Nucleic Acid(s)/Nucleic Acid Sequence(s)/nucleotide Sequence(s)

The terms "polynucleotide(s)", "nucleic acid sequence(s)", "nucleotide sequence(s)" are used interchangeably herein and refer to nucleotides, either ribonucleotides or deoxyribonucleotides or a combination of both, in a polymeric form of any length.

Control Plant(s)

The choice of suitable control plants is a routine part of an experimental setup and may include corresponding wild type plants or corresponding plants without the gene of interest. The control plant is typically of the same plant species or even of the same variety as the plant to be assessed. The control plant may also be a nullizygote of the plant to be assessed. A "control plant" as used herein refers not only to whole plants, but also to plant parts, including seeds and seed parts.

Homologue(s)

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intrasequence insertions of single or multiple amino acids. Generally, insertions within the polypeptide sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company and Table 1 below).

TABLE 1

Examples of conserved amino acid substitutions

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Derivatives

"Derivatives" include peptides, oligopeptides, polypeptides which may, compared to the polypeptide sequence of the naturally-occurring form of the protein, such as the one presented in SEQ ID NO: 2, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the polypeptide sequence from which it is derived, for example a reporter molecule or other ligand, covalently or non-covalently bound to the polypeptide sequence, such as a reporter molecule which is bound to facilitate its detection, and non-naturally occurring amino acid residues relative to the polypeptide sequence of a naturally-occurring protein.

Orthologue(s)/Paralogue(s)

Orthologues and paralogues encompass evolutionary concepts used to describe the ancestral relationships of genes. Paralogues are genes within the same species that have originated through duplication of an ancestral gene and orthologues are genes from different organisms that have originated through speciation.

Domain

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or activity of a protein. Identified by their high degree of conservation in aligned sequences of a family of protein homologues, they can be used as identifiers to determine if any polypeptide in question belongs to a previously identified polypeptide family.

Motif/Consensus Sequence/Signature

The term "motif" or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Hybridisation

The term "hybridisation" as defined herein is a process wherein substantially homologous complementary nucleotide sequences anneal to each other. The hybridisation process can occur entirely in solution, i.e. both complementary nucleic acid sequences are in solution. The hybridisation process can also occur with one of the complementary nucleic acid sequences immobilised to a matrix such as magnetic beads, Sepharose beads or any other resin. The hybridisation process can furthermore occur with one of the complementary nucleic acid sequences immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acid molecules.

The term "stringency" refers to the conditions under which a hybridisation takes place. The stringency of hybridisation is influenced by conditions such as temperature, salt concentration, ionic strength and hybridisation buffer composition. Generally, low stringency conditions are selected to be about 30° C. lower than the thermal melting point (Tm) for the specific sequence at a defined ionic strength and pH. Medium stringency conditions are when the temperature is 20° C. below Tm, and high stringency conditions are when the temperature is 10° C. below Tm. High stringency hybridisation conditions are typically used for isolating hybridising sequences that have high sequence similarity to the target nucleic acid sequence. However, nucleic acid sequences may deviate in sequence and still encode a substantially identical polypeptide, due to the degeneracy of the genetic code. Therefore medium stringency hybridisation conditions may sometimes be needed to identify such nucleic acid molecules.

The Tm is the temperature under defined ionic strength and pH, at which 50% of the target sequence hybridises to a perfectly matched probe. The Tm is dependent upon the solution conditions and the base composition and length of the probe. For example, longer sequences hybridise specifically at higher temperatures. The maximum rate of hybridisation is obtained from about 16° C. up to 32° C. below Tm. The presence of monovalent cations in the hybridisation solution reduce the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the Tm decreases about 1° C. per % base mismatch. The Tm may be calculated using the following equations, depending on the types of hybrids:

1) DNA-DNA Hybrids (Meinkoth and Wahl, Anal. Biochem., 138: 267-284, 1984):
$Tm=81.5°\ C.+16.6\times\log\ 10[Na^+]^a+0.41\times\%[G/C^b]-500\times[L^c]-1-0.61\times\%$ formamide 2) DNA-RNA or RNA-RNA Hybrids:
$Tm=79.8+18.5(\log_{10}[Na^+]^a)+0.58(\%\ G/C^b)+11.8(\%\ G/C^b)\ 2-820/L^c$ 3) Oligo-DNA or Oligo-RNA$^d$ Hybrids:
For <20 nucleotides: $Tm=2(ln)$
For 20-35 nucleotides: $Tm=22+1.46(ln)$ $^a$ or for other monovalent cation, but only accurate in the 0.01-0.4 M range.
$^b$ only accurate for % GC in the 30% to 75% range.
$^c$ L=length of duplex in base pairs.
$^d$ Oligo, oligonucleotide; ln, effective length of primer=2× (no. of G/C)+(no. of A/T).

Non-specific binding may be controlled using any one of a number of known techniques such as, for example, blocking the membrane with solutions containing proteins, additions of heterologous RNA, DNA, and SDS to the hybridisation buffer, and treatment with Rnase. For non-homologous probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridisation and which will either maintain or change the stringency conditions.

Besides the hybridisation conditions, specificity of hybridisation typically also depends on the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. A positive hybridisation gives a signal that is at least twice of that of the background. Generally, suitable stringent conditions for nucleic acid hybridisation assays or gene amplification detection procedures are as set forth above. More or less stringent conditions may also be selected. The skilled artisan is aware of various parameters which may be altered during washing and which will either maintain or change the stringency conditions.

For example, typical high stringency hybridisation conditions for DNA hybrids longer than 50 nucleotides encompass hybridisation at 65° C. in 1×SSC or at 42° C. in 1×SSC and 50% formamide, followed by washing at 65° C. in 0.3×SSC. Examples of medium stringency hybridisation conditions for DNA hybrids longer than 50 nucleotides encompass hybridisation at 50° C. in 4×SSC or at 40° C. in 6×SSC and 50% formamide, followed by washing at 50° C. in 2×SSC. The length of the hybrid is the anticipated length for the hybridising nucleic acid sequence. When nucleic acids of known sequence are hybridised, the hybrid length may be determined by aligning the sequences and identifying the conserved regions described herein. 1×SSC is 0.15M NaCl and 15 mM sodium citrate; the hybridisation solution and wash solutions may additionally include 5×Denhardt's reagent, 0.5-1.0% SDS, 100 µg/ml denatured, fragmented salmon sperm DNA, 0.5% sodium pyrophosphate.

For the purposes of defining the level of stringency, reference can be made to Sambrook et al. (2001) Molecular Cloning: a laboratory manual, 3rd Edition Cold Spring Harbor Laboratory Press, CSH, New York or to Current Protocols in Molecular Biology, John Wiley & Sons, N.Y. (1989 and yearly updates).

Splice Variant

The term "splice variant" as used herein encompasses variants of a nucleic acid sequence in which selected introns and/or exons have been excised, replaced, displaced or added, or in which introns have been shortened or lengthened. Such variants will be ones in which the biological activity of the protein is substantially retained; this may be achieved by selectively retaining functional segments of the protein. Such splice variants may be found in nature or may be manmade. Methods for predicting and isolating such splice variants are well known in the art (see for example Foissac and Schiex, BMC Bioinformatics. 2005; 6: 25).

Allelic Variant

Alleles or allelic variants are alternative forms of a given gene, located at the same chromosomal position. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

Gene Shuffling/Directed Evolution

Gene shuffling or directed evolution consists of iterations of DNA shuffling followed by appropriate screening and/or selection to generate variants of nucleic acid sequences or portions thereof encoding proteins having a modified biological activity (Castle et al., (2004) Science 304(5674): 1151-4; U.S. Pat. Nos. 5,811,238 and 6,395,547).

Regulatory Element/Control Sequence/Promoter

The terms "regulatory element", "control sequence" and "promoter" are all used interchangeably herein and are to be taken in a broad context to refer to regulatory nucleic acid sequences capable of effecting expression of the sequences to which they are ligated. The term "promoter" typically refers to a nucleic acid control sequence located upstream from the transcriptional start of a gene and which is involved in recognising and binding of RNA polymerase and other proteins, thereby directing transcription of an operably linked nucleic acid sequence. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid sequence in a cell, tissue or organ.

A "plant promoter" comprises regulatory elements, which mediate the expression of a coding sequence segment in plant cells. Accordingly, a plant promoter need not be of plant origin, but may originate from viruses or micro-organisms, for example from viruses which attack plant cells. The "plant promoter" can also originate from a plant cell, e.g. from the plant which is transformed with the nucleic acid sequence to be expressed in the inventive process and described herein. This also applies to other "plant" regulatory signals, such as "plant" terminators. The promoters upstream of the nucleotide sequences useful in the methods of the present invention can be modified by one or more nucleotide substitution(s), insertion(s) and/or deletion(s) without interfering with the functionality or activity of either the promoters, the open reading frame (ORF) or the 3'-regulatory region such as terminators or other 3' regulatory regions which are located away from the ORF. It is furthermore possible that the activity of the promoters is increased by modification of their sequence, or that they are replaced completely by more active promoters, even promoters from heterologous organisms. For expression in plants, the nucleic acid sequence must, as described above, be linked operably to or comprise a suitable promoter which expresses the gene at the right point in time and with the required spatial expression pattern.

Operably Linked

The term "operably linked" as used herein refers to a functional linkage between the promoter sequence and the gene of interest, such that the promoter sequence is able to initiate transcription of the gene of interest.

Constitutive Promoter

A "constitutive promoter" refers to a promoter that is transcriptionally active during most, but not necessarily all, phases of growth and development and under most environmental conditions, in at least one cell, tissue or organ. Table 2 below gives examples of constitutive promoters.

TABLE 2

Examples of constitutive promoters

| Gene Source | Expression Pattern | Reference |
|---|---|---|
| Actin | Constitutive | McElroy et al., Plant Cell, 2: 163-171, 1990 |
| CAMV 35S | Constitutive | Odell et al., Nature, 313: 810-812, 1985 |
| CaMV 19S | Constitutive | Nilsson et al., Physiol. Plant. 100: 456-462, 1997 |
| GOS2 | Constitutive | de Pater et al., Plant J Nov; 2(6): 837-44, 1992 |
| Ubiquitin | Constitutive | Christensen et al., Plant Mol. Biol. 18: 675-689, 1992 |
| Rice cyclophilin | Constitutive | Buchholz et al., Plant Mol Biol. 25(5): 837-43, 1994 |
| Maize H3 histone | Constitutive | Lepetit et al., Mol. Gen. Genet. 231: 276-285, 1992 |
| Actin 2 | Constitutive | An et al., Plant J. 10(1); 107-121, 1996 |

Ubiquitous Promoter

A Ubiquitous promoter is active in substantially all tissues or cells of an organism.

Developmentally-Regulated Promoter

A developmentally-regulated promoter is active during certain developmental stages or in parts of the plant that undergo developmental changes.

Inducible Promoter

An inducible promoter has induced or increased transcription initiation in response to a chemical (for a review see Gatz 1997, Annu. Rev. Plant Physiol. Plant Mol. Biol., 48:89-108), environmental or physical stimulus, or may be "stress-inducible", i.e. activated when a plant is exposed to various stress conditions, or a "pathogen-inducible" i.e. activated when a plant is exposed to exposure to various pathogens.

Organ-Specific/Tissue-Specific Promoter

An organ-specific or tissue-specific promoter is one that is capable of preferentially initiating transcription in certain organs or tissues, such as the leaves, roots, seed tissue etc. For example, a "root-specific promoter" is a promoter that is transcriptionally active predominantly in plant roots, substantially to the exclusion of any other parts of a plant, whilst still allowing for any leaky expression in these other plant parts. Promoters able to initiate transcription in certain cells only are referred to herein as "cell-specific".

Terminator

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

Selectable Marker (Gene)/Reporter Gene

"Selectable marker", "selectable marker gene" or "reporter gene" includes any gene that confers a phenotype on a cell in which it is expressed to facilitate the identification and/or selection of cells that are transfected or transformed with a nucleic acid construct of the invention. These marker genes enable the identification of a successful transfer of the nucleic acid sequences via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example bar which provides resistance to Basta®; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilisation of xylose, or antinutritive markers such as the resistance to 2-deoxyglucose). Expression of visual marker genes results in the formation of colour (for example β-glucuronidase, GUS or β-galactosidase with its coloured substrates, for example X-Gal), luminescence (such as the luciferin/luciferase system) or fluorescence (Green Fluorescent Protein, GFP, and derivatives thereof). This list represents only a small number of possible markers. The skilled worker is familiar with such markers. Different markers are preferred, depending on the organism and the selection method.

Transgenic/Transgene/Recombinant

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or (b) genetic control sequence(s) which is operably linked with the nucleic acid sequence according to the invention, for example a promoter, or (c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acid sequences used in the method of the invention are not at their natural locus in the genome of said plant, it being possible for the nucleic acid sequences to be expressed homologously or heterologously. However, as mentioned, transgenic also means that, while the nucleic acid sequences according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acid sequences according to the invention at an unnatural locus in the genome, i.e. homologous or, preferably, heterologous expression of the nucleic acid sequences takes place. Preferred transgenic plants are mentioned herein.

Transformation

The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic plants, including transgenic crop plants, are preferably produced via Agrobacterium-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for Agrobacterium-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acid sequences or the construct to be expressed is preferably cloned into a vector, which is suitable for transforming Agrobacterium tumefaciens, for example pBin19 (Bevan et al., Nucl. Acids Res. 12 (1984) 8711). Agrobacteria transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of Agrobacterium tumefaciens is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of Arabidopsis are treated with agrobacteria and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, eds, Methods in Arabidopsis Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of Arabidopsis, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J und Bent, A F (1998). The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3): 425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229).

TILLING

TILLING (Targeted Induced Local Lesions In Genomes) is a mutagenesis technology useful to generate and/or identify nucleic acid sequences encoding proteins with modified expression and/or activity. TILLING also allows selection of plants carrying such mutant variants. These mutant variants may exhibit modified expression, either in strength or in location or in timing (if the mutations affect the promoter for example). These mutant variants may exhibit higher activity than that exhibited by the gene in its natural form. TILLING combines high-density mutagenesis with high-throughput screening methods. The steps typically followed in TILLING are: (a) EMS mutagenesis (Redei GP and Koncz C (1992) In Methods in Arabidopsis Research, Koncz C, Chua N H, Schell J. eds. Singapore, World Scientific Publishing Co, pp. 16-82; Feldmann et al., (1994) In Meyerowitz E M, Somerville C R, eds, Arabidopsis. Cold Spring Harbor Laboratory Press, Cold Spring Harbor, N.Y., pp 137-172; Lightner J and Caspar T (1998) In J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum et al., (2000) Nat Biotechnol 18: 455-457; reviewed by Stemple (2004) Nat Rev Genet 5(2): 145-50).

Homologous Recombination

Homologous recombination allows introduction in a genome of a selected nucleic acid sequence at a defined selected position. Homologous recombination is a standard technology used routinely in biological sciences for lower organisms such as yeast or the moss *Physcomitrella*. Methods for performing homologous recombination in plants have been described not only for model plants (Offringa et al. (1990) EMBO J 9(10): 3077-84) but also for crop plants, for example rice (Terada et al. (2002) Nat Biotech 20(10): 1030-4; Iida and Terada (2004) Curr Opin Biotech 15(2): 132-8).

Yield

The term "yield" in general means a measurable produce of economic value, typically related to a specified crop, to an area, and to a period of time. Individual plant parts directly contribute to yield based on their number, size and/or weight, or the actual yield is the yield per acre for a crop and year, which is determined by dividing total production (includes both harvested and appraised production) by planted acres.

Increase/Improve/Enhance

The terms "increase", "improve" or "enhance" are interchangeable and shall mean in the sense of the application at least a 5%, 6%, 7%, 8%, 9% or 10%, preferably at least 15% or 20%, more preferably 25%, 30%, 35% or 40% more yield and/or growth in comparison to control plants as defined herein.

Seed Yield

Increased seed yield may manifest itself as one or more of the following: a) an increase in seed biomass (total seed weight) which may be on an individual seed basis and/or per plant and/or per hectare or acre; b) increased number of flowers per plant; c) increased number of (filled) seeds; d) increased seed filling rate (which is expressed as the ratio between the number of filled seeds divided by the total number of seeds); e) increased harvest index, which is expressed as a ratio of the yield of harvestable parts, such as seeds, divided by the total biomass; and f) increased thousand kernel weight (TKW), which is extrapolated from the number of filled seeds counted and their total weight. An increased TKW may result from an increased seed size and/or seed weight, and may also result from an increase in embryo and/or endosperm size.

An increase in seed yield may also be manifested as an increase in seed size and/or seed volume. Furthermore, an increase in seed yield may also manifest itself as an increase in seed area and/or seed length and/or seed width and/or seed perimeter. Increased yield may also result in modified architecture, or may occur because of modified architecture.

Plant

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid sequence of interest. The term "plant" also encompasses plant cells, suspension cultures, callus tissue, embryos, meristematic regions, gametophytes, sporophytes, pollen and microspores, again wherein each of the aforementioned comprises the gene/nucleic acid sequence of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana*, *Agropyron* spp., *Agrostis stolonifera*, *Allium* spp., *Amaranthus* spp., *Ammophila arenaria*, *Ananas comosus*, *Annona* spp., *Apium graveolens*, *Arachis* spp, *Artocarpus* spp., *Asparagus officinalis*, *Avena* spp. (e.g. *Avena sativa*, *Avena fatua*, *Avena byzantina*, *Avena fatua* var. *sativa*, *Avena hybrida*), *Averrhoa carambola*, *Bambusa* sp., *Benincasa hispida*, *Bertholletia excelsea*, *Beta vulgaris*, *Brassica* spp. (e.g. *Brassica napus*, *Brassica rapa* ssp. [canola, oilseed rape, turnip rape]), *Cadaba farinosa*, *Camellia sinensis*, *Canna indica*, *Cannabis sativa*, *Capsicum* spp., *Carex elata*, *Carica papaya*, *Carissa macrocarpa*, *Carya* spp., *Carthamus tinctorius*, *Castanea* spp., *Ceiba pentandra*, *Cichorium endivia*, *Cinnamomum* spp., *Citrullus lanatus*, *Citrus* spp., *Cocos* spp., *Coffea* spp., *Colocasia esculenta*, *Cola* spp., *Corchorus* sp., *Coriandrum sativum*, *Corylus* spp., *Crataegus* spp., *Crocus sativus*, *Cucurbita* spp., *Cucumis* spp., *Cynara* spp., *Daucus carota*, *Desmodium* spp., *Dimocarpus longan*, *Dioscorea* spp., *Diospyros* spp., *Echinochloa* spp., *Elaeis* (e.g. *Elaeis guineensis*, *Elaeis oleifera*), *Eleusine coracana*, *Erianthus* sp., *Eriobotrya japonica*, *Eucalyptus* sp., *Eugenia uniflora*, *Fagopyrum* spp., *Fagus* spp., *Festuca arundinacea*, *Ficus carica*, *Fortunella* spp., *Fragaria* spp., *Ginkgo biloba*, *Glycine* spp. (e.g. *Glycine max*, *Soja hispida* or *Soja max*), *Gossypium hirsutum*, *Helianthus* spp. (e.g. *Helianthus annuus*), *Hemerocallis fulva*, *Hibiscus* spp., *Hordeum* spp. (e.g. *Hordeum vulgare*), *Ipomoea batatas*, *Juglans* spp., *Lactuca sativa*, *Lathyrus* spp., *Lens culinaris*, *Linum usitatissimum*, *Litchi chinensis*, *Lotus* spp., *Luffa acutangula*, *Lupinus* spp., *Luzula sylvatica*, *Lycopersicon* spp. (e.g. *Lycopersicon esculentum*, *Lycopersicon lycopersicum*, *Lycopersicon pyriforme*), *Macrotyloma* spp., *Malus* spp., *Malpighia emarginata*, *Mammea americana*, *Mangifera indica*, *Manihot* spp., *Manikara zapota*, *Medicago sativa*, *Melilotus* spp., *Mentha* spp., *Miscanthus sinensis*, *Momordica* spp., *Morus nigra*, *Musa* spp., *Nicotiana* spp., *Olea* spp., *Opuntia* spp., *Ornithopus* spp., *Oryza* spp. (e.g. *Oryza sativa*, *Oryza latifolia*), *Panicum miliaceum*, *Panicum virgatum*, *Passiflora edulis*, *Pastinaca sativa*, *Pennisetum* sp., *Persea* spp., *Petroselinum crispum*, *Phalaris arundinacea*, *Phaseolus* spp., *Phleum pratense*, *Phoenix* spp., *Phragmites australis*, *Physalis* spp., *Pinus* spp., *Pistacia vera*, *Pisum* spp., *Poa* spp., *Populus* spp., *Prosopis* spp., *Prunus* spp., *Psidium* spp., *Punica granatum*, *Pyrus communis*, *Quercus* spp., *Raphanus sativus*, *Rheum rhabarbarum*, *Ribes* spp., *Ricinus communis*, *Rubus* spp., *Saccharum* spp., *Salix* sp., *Sambucus* spp., *Secale cereale*, *Sesamum* spp., *Sinapis* sp., *Solanum* spp. (e.g. *Solanum tuberosum*, *Solanum integrifolium* or *Solanum lycopersicum*), *Sorghum bicolor*, *Spinacia* spp., *Syzygium* spp., *Tagetes* spp., *Tamarindus indica*, *Theobroma cacao*, *Trifolium* spp., *Triticosecale rimpaui*, *Triticum* spp. (e.g. *Triticum aestivum*, *Triticum durum*, *Triticum turgidum*, *Triticum hybernum*, *Triticum macha*, *Triticum sativum* or *Triticum vulgare*), *Tropaeolum minus*, *Tropaeolum majus*, *Vaccinium* spp., *Vicia* spp., *Vigna* spp., *Viola odorata*, *Vitis* spp., *Zea mays*, *Zizania palustris*, *Ziziphus* spp., amongst others.

DETAILED DESCRIPTION OF THE INVENTION

According to a first embodiment, the present invention provides a method for increasing seed yield in plants relative to control plants, comprising increasing expression in a plant of a nucleic acid sequence encoding a DWF1 polypeptide.

A preferred method for increasing expression of a nucleic acid sequence encoding a DWF1 polypeptide is by introducing and expressing in a plant a nucleic acid sequence encoding a DWF1 polypeptide.

Any reference hereinafter to a "protein useful in the methods of the invention" is taken to mean a DWF1 polypeptide as defined herein. Any reference hereinafter to a "nucleic acid sequence useful in the methods of the invention" is taken to mean a nucleic acid sequence capable of encoding such a DWF1 polypeptide. The nucleic acid sequence to be introduced into a plant (and therefore useful in performing the methods of the invention) is any nucleic acid sequence encoding the type of protein, which will now be described, hereafter also named "DWF1 nucleic acid sequence" or "DWF1 gene".

A "DWF1 polypeptide" as defined herein refers to any polypeptide comprising from N-terminus to C-terminus: (i) a transmembrane domain; (ii) an FAD-binding domain; and (iii) a substrate-binding domain having in increasing order of preference at least 75%, 80%, 85%, 90%, 95%, 98% or more sequence identity to the substrate-binding domain as represented by SEQ ID NO: 29.

Alternatively or additionally, a "DWF1 polypeptide" as defined herein refers to any polypeptide having in increasing order of preference at least 75%, 80%, 85%, 90%, 95%, 98%, or more sequence identity to the DWF1 polypeptide as represented by SEQ ID NO: 2 or by SEQ ID NO: 34, or to any of the polypeptide sequences given in Table A herein.

Alternatively or additionally, a "DWF1 polypeptide" as defined herein refers to any polypeptide sequence which when used in the construction of a phylogenetic tree, such as the one depicted in FIG. 5, clusters with the clade of DWF1 polypeptides comprising the polypeptide sequence as represented by SEQ ID NO: 2 (of plant origin) rather than with any other DWF1 clade (of non-plant origin).

Furthermore, DWF1 polypeptides (at least in their native form) catalyse the conversion of 24-methylenecholesterol to campesterol (also the conversion of isofucosterol to sitosterol), consisting of an isomerization step (of the $\Delta^{24(28)}$ bond into a $\Delta^{24(25)}$ bond) and a subsequent reduction step of the new double bond. Tools and techniques for measuring plant endogenous sterols and metabolites of substrate feeding experiments are well known in the art. Complementation assays of mutant plants lacking DWF1 activity may also be performed to identify DWF1 polypeptides useful in performing the methods of the invention. Such methods are also well known in the art (more detailed in Example 6).

The terms "domain" and "motif" are defined in the "definitions" section herein. Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318, Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., (2004) Nucl. Acids. Res. 32: D134-D137), or Pfam (Bateman et al., (2002) Nucleic Acids Research 30(1): 276-280). A set of tools for in silico analysis of protein sequences is available on the ExPASY proteomics server (hosted by the Swiss Institute of Bioinformatics (Gasteiger et al., (2003) ExPASy: the proteomics server for in-depth protein knowledge and analysis, Nucleic Acids Res 31: 3784-3788). Domains may also be identified using routine techniques, such as by sequence alignment.

Analysis of the polypeptide sequence of SEQ ID NO: 2 is presented below in Examples 2 and 4. Various enzymes use flavin adenine dinucleotide (FAD) as a co-factor (which functions in electron transfers), most of these enzymes are oxygen-dependent oxidoreductases. The FAD-binding domain of the DWF1 polypeptides useful in performing the methods of the invention is represented in the InterPro database by accession number IPR006094, in the Pfam database by accession number PF01565, in the Superfamily database by accession number SSF56176. The FAD-binding domain comprises subdomains for the binding of pyrophosphate, ADP, isoalloxazine, and adenine (Fraaije et al. (1998) Trends Biochem Sci 23: 206-207; Choe et al. (1999) Plant Physiol 119: 897-907). These are boxed in FIG. 4.

The substrate-binding domain (such as SEQ ID NO: 29 comprised in the DWF1 polypeptide of SEQ ID NO: 2), is defined as the domain located downstream (from N-terminus to C-terminus) of the FAD-binding domain (as identified by the Superfamily accession number SSF56176 on the DWF1 polypeptide of SEQ ID NO: 2). The substrates for DWF1 polypeptide are 24-methylenecholesterol or isofucosterol, which are converted respectively into campesterol and sitosterol. This conversion proceeds in two steps: an isomerisation of the $\Delta^{24(28)}$ bond into a $\Delta^{24(25)}$ bond, followed by a reduction of the new double bond (Khlare et al. (1998) Plant Cell 10: 1677-1690). This substrate-binding domain may be identified in DWF1 polypeptides by alignment with the DWF1 polypeptide as represented by SEQ ID NO: 2, or with the substrate-binding domain as represented by SEQ ID NO: 29.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences). Minor manual editing may be performed to optimise alignment between conserved motifs, as would be apparent to a person skilled in the art. Furthermore, instead of using full-length sequences for the identification of homologues, specific domains may also be used. The sequence identity values, which are indicated below in Example 3 as a percentage were determined over the entire nucleic acid or polypeptide sequence (Table B herein), and/or over selected domains (such as the substrate-binding domain as represented by SEQ ID NO: 29; Table B1 herein) or conserved motif(s), using the programs mentioned above using the default parameters.

The present invention is illustrated by transforming plants with the nucleic acid sequence represented by SEQ ID NO: 1 or SEQ ID NO: 33, encoding the polypeptide sequence of SEQ ID NO: 2 or of SEQ ID NO: 34. However, performance of the invention is not restricted to these sequences; the methods of the invention may advantageously be performed using any DWF1-encoding nucleic acid sequence or DWF1 polypeptides as defined herein.

Examples of nucleic acid sequences encoding plant DWF1 polypeptides are given in Table A of Example 1 herein. Such nucleic acid sequences are useful in performing the methods of the invention. The polypeptide sequences given in Table A of Example 1 are example sequences of orthologues and paralogues of the DWF1 polypeptides represented by SEQ ID NO: 2, or by SEQ ID NO: 34, the terms "orthologues" and "paralogues" being as defined herein. Further orthologues and paralogues may readily be identified by performing a so-called reciprocal blast search. Typically, this involves a first BLAST involving BLASTing a query sequence (for example using any of the sequences listed in Table A of Example 1) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 1, SEQ ID NO: 2, SEQ ID NO: 33, SEQ ID NO: 34) or the second BLAST would therefore be against *Saccharum* sequences). The results of the first and second BLASTs are then compared. A paralogue is identified if a high-ranking hit from the first blast is from the same species as from which the query sequence is derived, a BLAST back then ideally results in the query sequence amongst the highest hits; an orthologue is identified if a high-ranking hit in the first BLAST is not from the same species as from which the query sequence is derived, and preferably results upon BLAST back in the query sequence being among the highest hits.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbour joining tree, to help visualize clustering of related genes and to identify orthologues and paralogues (see FIG. 5).

The task of protein subcellular localisation prediction is important and well studied. Experimental methods for protein localization range from immunolocalization to tagging of proteins using green fluorescent protein (GFP). Such methods are accurate although labor-intensive compared with computational methods. Recently much progress has been made in computational prediction of protein localisation from sequence data. Among algorithms well known to a person skilled in the art are available at the ExPASy Proteomics tools hosted by the Swiss Institute for Bioinformatics, for example, PSort, TargetP, ChloroP, Predotar, LipoP, MITOPROT, PATS, PTS1, SignalP and others.

For membrane-spanning proteins, the prediction of the location and orientation of alpha helices is done using the TMHMM2.0 algorithm based on a hidden Markov model (HMM). For example, analysis performed on the DWF1 polypeptide as represented by SEQ ID NO: 2 shows it comprises only one membrane spanning domain, the majority of the protein is facing the cytosol, while the N-terminus is anchored in a membrane, most likely an endomembrane system such as the endoplasmic reticulum (ER), the Golgi apparatus, and mitochondria (see Example 5 and FIGS. 2 and 3 herein).

Nucleic acid variants may also be useful in practising the methods of the invention. Examples of such variants include nucleic acid sequences encoding homologues and derivatives of any one of the polypeptide sequences given in Table A of Example 1, the terms "homologue" and "derivative" being as defined herein. Also useful in the methods of the invention are nucleic acid sequences encoding homologues and derivatives of orthologues or paralogues of any one of the polypeptide sequences given in Table A of Example 1. Homologues and derivatives useful in the methods of the present invention have substantially the same biological and functional activity as the unmodified protein from which they are derived.

Further nucleic acid variants useful in practising the methods of the invention include portions of nucleic acid sequences encoding DWF1 polypeptides, nucleic acid sequences hybridising to nucleic acid sequences encoding DWF1 polypeptides, splice variants of nucleic acid sequences encoding DWF1 polypeptides, allelic variants of nucleic acid sequences encoding DWF1 polypeptides, and variants of nucleic acid sequences encoding DWF1 polypeptides obtained by gene shuffling. The terms hybridising sequence, splice variant, allelic variant and gene shuffling are as described herein.

Nucleic acid sequences encoding DWF1 polypeptides need not be full-length nucleic acid sequences, since performance of the methods of the invention does not rely on the use of full-length nucleic acid sequences. According to the present invention, there is provided a method for increasing seed yield in plants, comprising introducing and expressing in a plant a portion of any one of the nucleic acid sequences given in Table A of Example 1, or a portion of a nucleic acid sequence encoding an orthologue, paralogue or homologue of any of the polypeptide sequences given in Table A of Example 1.

A portion of a nucleic acid sequence may be prepared, for example, by making one or more deletions to the nucleic acid sequence. The portions may be used in isolated form or they may be fused to other coding (or non-coding) sequences in order to, for example, produce a protein that combines several activities. When fused to other coding sequences, the resultant polypeptide produced upon translation may be bigger than that predicted for the protein portion.

Portions useful in the methods of the invention, encode DWF1 polypeptides as defined herein, and have substantially the same biological activity as the polypeptide sequences given in Table A of Example 1. Preferably, the portion is a portion of any one of the nucleic acid sequences given in Table A of Example 1, or is a portion of a nucleic acid sequence encoding an orthologue or paralogue of any one of the polypeptide sequences given in Table A of Example 1. Preferably the portion is, in increasing order of preference at least 300, 400, 500 or 600 consecutive nucleotides in length, the consecutive nucleotides being of any one of the nucleic acid sequences given in Table A of Example 1, or of a nucleic acid sequence encoding an orthologue or paralogue of any one of the polypeptide sequences given in Table A of Example 1. Most preferably the portion is a portion of the nucleic acid sequence of SEQ ID NO: 1 or of SEQ ID NO: 33. Preferably, the portion encodes a polypeptide sequence comprising any one or more of the domains or motifs defined herein. Preferably, the portion encodes a polypeptide sequence which when used in the construction of a phylogenetic tree, such as the one depicted in FIG. 5, clusters with the clade of DWF1 polypeptides comprising the polypeptide sequence as represented by SEQ ID NO: 2 (of plant origin) rather than with any other DWF1 clade (of non-plant origin).

Another nucleic acid variant useful in the methods of the invention is a nucleic acid sequence capable of hybridising, under reduced stringency conditions, preferably under stringent conditions, with a nucleic acid sequence encoding a DWF1 polypeptide as defined herein, or with a portion as defined herein.

According to the present invention, there is provided a method for increasing seed yield in plants, comprising introducing and expressing in a plant a nucleic acid sequence capable of hybridizing to any one of the nucleic acid sequences given in Table A of Example 1, or comprising introducing and expressing in a plant a nucleic acid sequence capable of hybridising to a nucleic acid sequence encoding an orthologue, paralogue or homologue of any of the nucleic acid sequences given in Table A of Example 1.

Hybridising sequences useful in the methods of the invention encode a DWF1 polypeptide as defined herein, and have substantially the same biological activity as the polypeptide sequences given in Table A of Example 1. Preferably, the hybridising sequence is capable of hybridising to any one of the nucleic acid sequences given in Table A of Example 1, or to a portion of any of these sequences, a portion being as defined above, or wherein the hybridising sequence is capable of hybridising to a nucleic acid sequence encoding an orthologue or paralogue of any one of the polypeptide sequences given in Table A of Example 1. Most preferably, the hybridising sequence is capable of hybridising to a nucleic acid sequence as represented by SEQ ID NO: 1 or to a portion thereof, or by SEQ ID NO: 33 or to a portion thereof. Preferably, the hybridising sequence encodes a polypeptide sequence comprising any one or more of the motifs or domains as defined herein. Preferably, the hybridising sequence encodes a polypeptide sequence which when used in the construction of a phylogenetic tree, such as the one depicted in FIG. 5, clusters with the lade of DWF1 polypeptides comprising the polypeptide sequence as represented by SEQ ID NO: 2 (of plant origin) rather than with any other DWF1 lade (of non-plant origin).

Another nucleic acid variant useful in the methods of the invention is a splice variant encoding a DWF1 polypeptide as defined hereinabove, a splice variant being as defined herein.

According to the present invention, there is provided a method for increasing seed yield in plants, comprising introducing and expressing in a plant a splice variant of any one of the nucleic acid sequences given in Table A of Example 1, or a splice variant of a nucleic acid sequence encoding an orthologue, paralogue or homologue of any of the polypeptide sequences given in Table A of Example 1.

The splice variants useful in the methods of the present invention have substantially the same biological activity as the DWF1 polypeptide of SEQ ID NO: 2 or of SEQ ID NO: 34, and any of the polypeptide sequences depicted in Table A of Example 1. Preferably, the polypeptide sequence encoded by the splice variant comprises any one or more of the motifs or domains as defined herein. Preferably, the polypeptide sequence encoded by the splice variant, when used in the construction of a phylogenetic tree, such as the one depicted in FIG. 5, clusters with the lade of DWF1 polypeptides comprising the polypeptide sequence as represented by SEQ ID NO: 2 (of plant origin) rather than with any other DWF1 lade (of non-plant origin).

Another nucleic acid variant useful in performing the methods of the invention is an allelic variant of a nucleic acid sequence encoding a DWF1 polypeptide as defined hereinabove, an allelic variant being as defined herein.

According to the present invention, there is provided a method for increasing seed yield in plants, comprising introducing and expressing in a plant an allelic variant of any one of the nucleic acid sequences given in Table A of Example 1, or comprising introducing and expressing in a plant an allelic variant of a nucleic acid sequence encoding an orthologue, paralogue or homologue of any of the polypeptide sequences given in Table A of Example 1.

The allelic variants useful in the methods of the present invention have substantially the same biological activity as the DWF1 polypeptide of SEQ ID NO: 2 or of SEQ ID NO: 34, and any of the polypeptide sequences depicted in Table A of Example 1. Allelic variants exist in nature, and encompassed within the methods of the present invention is the use of these natural alleles. Preferably, the allelic variant is an allelic variant of SEQ ID NO: 1 or of SEQ ID NO: 33, or an allelic variant of a nucleic acid sequence encoding an orthologue or paralogue of SEQ ID NO: 2 or of SEQ ID NO: 34. Preferably, the polypeptide sequence encoded by the allelic variant comprises any one or more of the motifs or domains as defined herein. Preferably, the polypeptide sequence encoded by the allelic variant, when used in the construction of a phylogenetic tree, such as the one depicted in FIG. 5, clusters with the lade of DWF1 polypeptides comprising the polypeptide sequence as represented by SEQ ID NO: 2 (of plant origin) rather than with any other DWF1 lade (of non-plant origin).

Gene shuffling or directed evolution may also be used to generate variants of nucleic acid sequences encoding DWF1 polypeptides as defined above; the term "gene shuffling" being as defined herein.

According to the present invention, there is provided a method for increasing seed yield in plants, comprising introducing and expressing in a plant a variant of any one of the nucleic acid sequences given in Table A of Example 1, or comprising introducing and expressing in a plant a variant of a nucleic acid sequence encoding an orthologue, paralogue or homologue of any of the polypeptide sequences given in Table A of Example 1, which variant nucleic acid sequence is obtained by gene shuffling.

The variant nucleic acid sequences obtained by gene shuffling useful in the methods of the present invention have substantially the same biological activity as the DWF1 polypeptide of SEQ ID NO: 2 or of SEQ ID NO: 34, and any of the polypeptide sequences depicted in Table A of Example 1. Preferably, the variant nucleic acid sequence obtained by gene shuffling encodes a polypeptide sequence comprising any one or more of the motifs or domains as defined herein. Preferably, the polypeptide sequence encoded by the variant nucleic acid sequence obtained by gene shuffling, when used in the construction of a phylogenetic tree, such as the one depicted in FIG. 5, clusters with the lade of DWF1 polypeptides comprising the polypeptide sequence as represented by SEQ ID NO: 2 (of plant origin) rather than with any other DWF1 lade (of non-plant origin).

Furthermore, nucleic acid variants may also be obtained by site-directed mutagenesis. Several methods are available to achieve site-directed mutagenesis, the most common being PCR based methods (Current Protocols in Molecular Biology, Wiley Eds.).

Nucleic acid sequences encoding DWF1 polypeptides may be derived from any natural or artificial source. The nucleic acid sequence may be modified from its native form in composition and/or genomic environment through deliberate human manipulation. Preferably the DWF1 polypeptide-encoding nucleic acid sequence is from a plant, further preferably from a monocotyledonous plant, more preferably from the family Poaceae, more preferably from the genus *Saccharum*, most preferably from *Saccharum officinarum*.

Performance of the methods of the invention gives plants having increased seed yield relative to control plants. The terms "seed yield" is described in more detail in the "definitions" section herein.

Reference herein to enhanced yield-related traits is taken to mean an increase in biomass (weight) of one or more parts of a plant, which may include aboveground (harvestable) parts and/or (harvestable) parts below ground. In particular, such harvestable parts are seeds, and performance of the methods of the invention results in plants having increased seed yield relative to the seed yield of control plants.

Taking corn as an example, a yield increase may be manifested as one or more of the following: increase in the number of plants established per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

The present invention provides a method for increasing seed yield of plants relative to control plants, which method comprises increasing expression in a plant of a nucleic acid sequence encoding a DWF1 polypeptide as defined herein. Preferably, increased seed yield is one or both of: increased thousand kernel weight (TKW) or increased total seed weight per plant.

Since the transgenic plants according to the present invention have increased seed yield, it is likely that these plants exhibit an increased growth rate (during at least part of their life cycle), relative to the growth rate of control plants at a corresponding stage in their life cycle.

The increased growth rate may be specific to one or more parts of a plant (including seeds), or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, greenness index, flowering time and speed of seed maturation. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible (a similar effect may be obtained with earlier flowering time). If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of corn plants followed by, for example, the sowing and optional harvesting of soybean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

According to a preferred feature of the present invention, performance of the methods of the invention gives plants having an increased growth rate relative to control plants. Therefore, according to the present invention, there is provided a method for increasing the growth rate of plants, which method comprises increasing expression in a plant of a nucleic acid sequence encoding a DWF1 polypeptide as defined herein.

An increase in yield and/or growth rate occurs whether the plant is under non-stress conditions or whether the plant is exposed to various stresses compared to control plants grown under comparable conditions. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the everyday biotic and/or abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, nematodes, fungi and insects. The term "non-stress" conditions as used herein are those environmental conditions that allow optimal growth of plants. Persons skilled in the art are aware of normal soil conditions and climatic conditions for a given location.

Performance of the methods of the invention gives plants grown under non-stress conditions or under mild drought conditions increased seed yield relative to control plants grown under comparable conditions. Therefore, according to the present invention, there is provided a method for increasing seed yield in plants grown under non-stress conditions or under mild drought conditions, which method comprises increasing expression in a plant of a nucleic acid sequence encoding a DWF1 polypeptide as defined above.

Performance of the methods according to the present invention results in plants grown under abiotic stress, having increased seed yield relative to control plants grown under comparable conditions. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signaling pathways and cellular responses, such as the production of stress proteins, up-regulation of antioxidants, accumulation of compatible solutes and growth arrest. Since diverse environmental stresses activate similar pathways, an exemplification with drought stress, for example, should not be seen as a limitation to drought stress, but more as a screen to indicate the involvement of DWF1 polypeptides as defined above, in increasing seed yield relative to control plants grown in comparable stress conditions, in abiotic stresses in general.

The term "abiotic stress" as defined herein is taken to mean any one or more of: water stress (due to drought or excess water), anaerobic stress, salt stress, temperature stress (due to hot, cold or freezing temperatures), chemical toxicity stress and oxidative stress. According to one aspect of the invention, the abiotic stress is an osmotic stress, selected from water stress, salt stress, oxidative stress and ionic stress. Preferably, the water stress is drought stress. The term salt stress is not restricted to common salt (NaCl), but may be any stress caused by one or more of: NaCl, KCl, LiCl, $MgCl_2$, $CaCl_2$, amongst others.

Performance of the methods of the invention gives plants having increased seed yield, under abiotic stress conditions relative to control plants grown in comparable stress conditions. Therefore, according to the present invention, there is provided a method for increasing seed yield in plants grown under abiotic stress conditions, which method comprises increasing expression in a plant of a nucleic acid sequence encoding a DWF1 polypeptide. According to one aspect of the invention, the abiotic stress is an osmotic stress, selected from one or more of the following: water stress, salt stress, oxidative stress and ionic stress.

Another example of abiotic environmental stress is the reduced availability of one or more nutrients that need to be assimilated by the plants for growth and development. Because of the strong influence of nutrition utilization efficiency on plant yield and product quality, a huge amount of fertilizer is poured onto fields to optimize plant growth and quality. Productivity of plants ordinarily is limited by three primary nutrients, phosphorous, potassium and nitrogen, which is usually the rate-limiting element in plant growth of these three. Therefore the major nutritional element required for plant growth is nitrogen (N). It is a constituent of numerous important compounds found in living cells, including amino acids, proteins (enzymes), nucleic acids, and chlorophyll. 1.5% to 2% of plant dry matter is nitrogen and approximately 16% of total plant protein. Thus, nitrogen availability is a major limiting factor for crop plant growth and production (Frink et al. (1999) Proc Natl Acad Sci USA 96(4): 1175-1180), and has as well a major impact on protein accumulation and amino acid composition. Therefore, of great interest are crop plants with increased yield-related traits (such as seed yield), when grown under nitrogen-limiting conditions.

Performance of the methods of the invention gives plants grown under conditions of reduced nutrient availability, particularly under conditions of reduced nitrogen availability, having increased seed yield relative to control plants grown under comparable conditions. Therefore, according to the present invention, there is provided a method for increasing seed yield in plants grown under conditions of reduced nutrient availability, preferably reduced nitrogen availability, which method comprises increasing expression in a plant, of a nucleic acid sequence encoding a DWF1 polypeptide. Reduced nutrient availability may result from a deficiency or excess of nutrients such as nitrogen, phosphates and other phosphorous-containing compounds, potassium, calcium, cadmium, magnesium, manganese, iron and boron, amongst others. Preferably, reduced nutrient availability is reduced nitrogen availability.

The present invention encompasses plants or parts thereof (including seeds) obtainable by the methods according to the present invention. The plants, plant parts or plant cells comprise a nucleic acid transgene encoding a DWF1 polypeptide as defined above.

The invention also provides genetic constructs and vectors to facilitate introduction and/or expression in plants of nucleic acid sequences encoding DWF1 polypeptides. The gene constructs may be inserted into vectors, which may be commercially available, suitable for transforming into plants and suitable for expression of the gene of interest in the transformed cells. The invention also provides use of a gene construct as defined herein in the methods of the invention.

More specifically, the present invention provides a construct comprising:
 (a) a nucleic acid sequence encoding a DWF1 polypeptide as defined above;
 (b) one or more control sequences capable of driving expression of the nucleic acid sequence of (a); and optionally
 (c) a transcription termination sequence.

The term "control sequence" and "termination sequence" are as defined herein.

Plants are transformed with a vector comprising any of the nucleic acid sequences described above. The skilled artisan is well aware of the genetic elements that must be present on the vector in order to successfully transform, select and propagate host cells containing the sequence of interest. The sequence of interest is operably linked to one or more control sequences (at least to a promoter).

Advantageously, any type of promoter may be used to drive expression of the nucleic acid sequence. A constitutive promoter is particularly useful in the methods of the invention. It should be clear that the applicability of the present invention is not restricted to the nucleic acid sequence encoding a DWF1 polypeptide, as represented by SEQ ID NO: 1 or by SEQ ID NO: 33, nor is the applicability of the invention restricted to expression of a nucleic acid sequence encoding a DWF1 polypeptide, when driven by a constitutive promoter.

The constitutive promoter is preferably a GOS2 promoter, preferably a GOS2 promoter from rice, more preferably a GOS2 promoter as represented by SEQ ID NO: 32 or SEQ ID NO: 39. See Table 2 in the "Definitions" section herein for further examples of constitutive promoters.

For the identification of functionally equivalent promoters, the promoter strength and/or expression pattern of a candidate promoter may be analysed for example by operably linking the promoter to a reporter gene and assaying the expression level and pattern of the reporter gene in various tissues of the plant. Suitable well-known reporter genes include for example beta-glucuronidase or beta galactosidase. The promoter activity is assayed by measuring the enzymatic activity of the beta-glucuronidase or beta-galactosidase. The promoter strength and/or expression pattern may then be compared to that of a reference promoter (such as the one used in the methods of the present invention). Alternatively, promoter strength may be assayed by quantifying mRNA levels or by comparing mRNA levels of the nucleic acid sequence used in the methods of the present invention, with mRNA levels of housekeeping genes such as 18S rRNA, using methods known in the art, such as Northern blotting with densitometric analysis of autoradiograms, quantitative realtime PCR or RT-PCR (Heid et al., 1996 Genome Methods 6: 986-994). Generally by "weak promoter" is intended a promoter that drives expression of a coding sequence at a low level. By "low level" is intended at levels of about 1/10,000 transcripts to about 1/100,000 transcripts, to about 1/500, 0000 transcripts per cell. Conversely, a "strong promoter" drives expression of a coding sequence at high level, or at about 1/10 transcripts to about 1/100 transcripts to about 1/1,000 transcripts per cell.

Optionally, one or more terminator sequences may be used in the construct introduced into a plant. Additional regulatory elements may include transcriptional as well as translational enhancers. Those skilled in the art will be aware of terminator and enhancer sequences that may be suitable for use in performing the invention. Such sequences would be known or may readily be obtained by a person skilled in the art.

An intron sequence may also be added to the 5' untranslated region (UTR) or in the coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, Mol. Cell Biol. 8:4395-4405 (1988); Callis et al., Genes Dev. 1:1183-1200 (1987)). Such intron enhancement of gene expression is typically greatest when placed near the 5' end of the transcription unit. Use of the maize introns Adh1-S intron 1, 2, and 6, the Bronze-1 intron are known in the art. For general information, see The Maize Handbook, Chapter 116, Freeling and Walbot, Eds., Springer, N.Y. (1994).

Other control sequences (besides promoter, enhancer, silencer, intron sequences, 3'UTR and/or 5'UTR regions) may be protein and/or RNA stabilizing elements. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

For the detection of the successful transfer of the nucleic acid sequences as used in the methods of the invention and/or selection of transgenic plants comprising these nucleic acid sequences, it is advantageous to use marker genes (or reporter genes). Therefore, the genetic construct may optionally comprise a selectable marker gene. Selectable markers are described in more detail in the "definitions" section herein.

It is known that upon stable or transient integration of nucleic acid sequences into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid sequences encoding a selectable marker can be introduced into a host cell on the same vector that comprises the sequence encoding the polypeptides of the invention or used in the methods of the invention, or else in a separate vector. Cells which have been stably transfected with the introduced nucleic acid sequence can be identified for example by selection (for example, cells which have integrated the selectable marker survive whereas the other cells die).

Since the marker genes, particularly genes for resistance to antibiotics and herbicides, are no longer required or are undesired in the transgenic host cell once the nucleic acid sequences have been introduced successfully, the process according to the invention for introducing the nucleic acid sequences advantageously employs techniques, which enable the removal or excision of these marker genes. One such a method is what is known as co-transformation. The co-transformation method employs two vectors simultaneously for the transformation, one vector bearing the nucleic acid sequence according to the invention and a second bearing the marker gene(s). A large proportion of transformants receives or, in the case of plants, comprises (up to 40% or more of the transformants), both vectors. In case of transformation with Agrobacteria, the transformants usually receive only a part of the vector, i.e. the sequence flanked by the T-DNA, which usually represents the expression cassette. The marker genes can subsequently be removed from the transformed plant by performing crosses. In another method, marker genes integrated into a transposon are used for the transformation together with desired nucleic acid sequence (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible. Naturally, these methods can also be applied to microorganisms such as yeast, fungi or bacteria.

The invention also provides a method for the production of transgenic plants having increased seed yield relative to control plants, comprising introduction and expression in a plant of any nucleic acid sequence encoding a DWF1 polypeptide as defined hereinabove. More specifically, the present invention provides a method for the production of transgenic plants having increased seed yield, which method comprises:

(i) introducing and expressing in a plant or plant cell a nucleic acid sequence encoding DWF1 polypeptide; and
(ii) cultivating the plant cell under conditions promoting plant growth and development.

The nucleic acid sequence may be introduced directly into a plant cell or into the plant itself (including introduction into a tissue, organ or any other part of a plant). According to a preferred feature of the present invention, the nucleic acid sequence is preferably introduced into a plant by transformation. The term "transformation" is described in more detail in the "definitions" section herein.

The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis or quantitative PCR, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated nucleic acid sequence encoding a DWF1 polypeptide as defined hereinabove. Preferred host cells according to the invention are plant cells. Host plants for the nucleic acid sequences or the vector used in the method according to the invention, the expression cassette or construct or vector are, in principle, advantageously all plants, which are capable of synthesizing the polypeptides used in the inventive method.

The methods of the invention are advantageously applicable to any plant.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs. According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, triticale, sorghum and oats.

The invention also extends to harvestable parts of a plant such as, but not limited to seeds, leaves, fruits, flowers, stems, rhizomes, tubers and bulbs. The invention furthermore relates to products derived, preferably directly derived, from a harvestable part of such a plant, such as dry pellets or powders, oil, fat and fatty acids, starch or proteins.

Methods for increasing expression of nucleic acid sequences or genes, or gene products, are well documented in the art and include, for example, overexpression driven by appropriate promoters, the use of transcription enhancers or translation enhancers. Isolated nucleic acid sequences which serve as promoter or enhancer elements may be introduced in an appropriate position (typically upstream) of a non-heterologous form of a polynucleotide so as to upregulate expression. For example, endogenous promoters may be altered in vivo by mutation, deletion, and/or substitution (see, Kmiec, U.S. Pat. No. 5,565,350; Zarling et al., PCT/US93/03868), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

As mentioned above, a preferred method for increasing expression of a nucleic acid sequence encoding a DWF1 polypeptide is by introducing and expressing in a plant a nucleic acid sequence encoding a DWF1 polypeptide; however the effects of performing the method, i.e. increasing seed yield, may also be achieved using other well known techniques. A description of some of these techniques will now follow.

One such technique is T-DNA activation tagging (Hayashi et al. Science (1992) 1350-1353), which involves insertion of T-DNA, usually containing a promoter (may also be a translation enhancer or an intron), in the genomic region of the gene of interest or 10 kb up- or downstream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through Agrobacterium infection and leads to modified expression of genes near the inserted T-DNA. The resulting transgenic plants show dominant phenotypes due to modified expression of genes close to the introduced promoter.

The effects of the invention may also be reproduced using the technique of TILLING (Targeted Induced Local Lesions In Genomes); for a description of the same see the "definitions" section.

The effects of the invention may also be reproduced using homologous recombination; for a description of the same see the "definitions" section.

The present invention also encompasses use of nucleic acid sequences encoding DWF1 polypeptides as described herein and use of these DWF1 polypeptides in increasing seed yield in plants relative to control plants. Preferably, increased seed yield is one or both of increased TKW or increased total seed weight per plant.

Nucleic acid sequences encoding DWF1 polypeptides described herein, or the DWF1 polypeptides themselves, may find use in breeding programmes in which a DNA marker is identified, which may be genetically linked to a gene encoding a DWF1 polypeptide. The genes/nucleic acid sequences or the DWF1 polypeptides themselves may be used to define a molecular marker. This DNA or protein marker may then be used in breeding programmes to select plants having increased seed yield as defined hereinabove in the methods of the invention.

Allelic variants of a gene/nucleic acid sequence encoding a DWF1 polypeptide may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give increased seed yield. Selection is typically carried out by monitoring growth performance of plants containing different allelic variants of the sequence in question. Growth performance may be monitored in a greenhouse or in the field. Further optional steps include crossing plants in which the superior allelic variant was identified with another plant. This could be used, for example, to make a combination of interesting phenotypic features.

Nucleic acid sequences encoding DWF1 polypeptides may also be used as probes for genetically and physically mapping the genes that they are a part of, and as markers for traits linked to those genes. Such information may be useful in plant breeding in order to develop lines with desired phenotypes. Such use of nucleic acid sequences encoding a DWF1 polypeptide requires only a nucleic acid sequence of at least 15 nucleotides in length. The nucleic acid sequences encoding a DWF1 polypeptide may be used as restriction fragment length polymorphism (RFLP) markers. Southern blots (Sambrook J. Fritsch E F and Maniatis T (1989) Molecular Cloning, A Laboratory Manual) of restriction-digested plant genomic DNA may be probed with nucleic acid sequences encoding the DWF1 polypeptide. The resulting banding patterns may then be subjected to genetic analyses using computer programs such as MapMaker (Lander et al. (1987) Genomics 1: 174-181) in order to construct a genetic map. In addition, the nucleic acid sequences may be used to probe Southern blots containing restriction endonuclease-treated genomic DNAs of a set of individuals representing parent and progeny of a defined genetic cross. Segregation of the DNA polymorphisms is noted and used to calculate the position of the nucleic acid sequence encoding the DWF1 polypeptide in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridisation (FISH) mapping (Trask (1991) Trends Genet. 7:149-154). Although current methods of FISH mapping favour use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acid sequences. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having increased seed yield relative to control plants, as described hereinbefore. This trait may also be combined with other economically advantageous traits, such as further yield-enhancing traits, tolerance to other abiotic and biotic stresses, traits modifying various architectural features and/or biochemical and/or physiological features.

DESCRIPTION OF FIGURES

The present invention will now be described with reference to the following figures in which:

FIG. 4A-J show a CLUSTAL W (1;83) multiple sequence alignment of DWF1 polypeptides from various source species. A signal peptide and a single transmembrane domain as identified by TMHMM2.0, are boxed. The FAD-binding domain as predicted by the SuperFamily accession SSF56176 is underlined with Xs, by the InterPro accession IPR006094underlined with Ys, and by Choe et al. ((1999) Plant Physiol 119: 897-907) underlined with Zs. Within the FAD-binding domain, are boxed subdomains for the binding of pyrophosphate, ADP, isoalloxazine, and adenine (according to Fraaije et al. (1998) Trends Biochem Sci 23: 206-207; Choe et al. (1999) Plant Physiol 119: 897-907). The substrate-binding domain, for example as represented by SEQ ID NO: 29 comprised in SEQ ID NO: 2, is underlined with a thick black line. The sequences shown are: Arath_DWF1, SEQ ID NO: 4; Brara_DWF1, SEQ ID NO: 6; Glyma_DWF1, SEQ ID NO: 8; Pissa DWF1, SEQ ID NO: 16; Poptr_DWF1, SEQ ID NO: 18; Goshi_DWF1, SEQ ID NO: 10; Lyces DWF1, SEQ ID NO: 12; Zinel_DWF1, SEQ ID NO: 24; Sacof_DWF1, SEQ ID NO: 34; Zeama_DWF1, SEQ ID NO: 22; Orysa_DWF1, SEQ ID NO: 14; Triae_DWF1, SEQ ID NO: 20; Danre_dhcr24, SEQ ID NO: 28; Homsa_DWF1, SEQ ID NO: 26.

FIG. 7A-Q detail examples of sequences useful in performing the methods according to the present invention.

EXAMPLES

Figure 1:
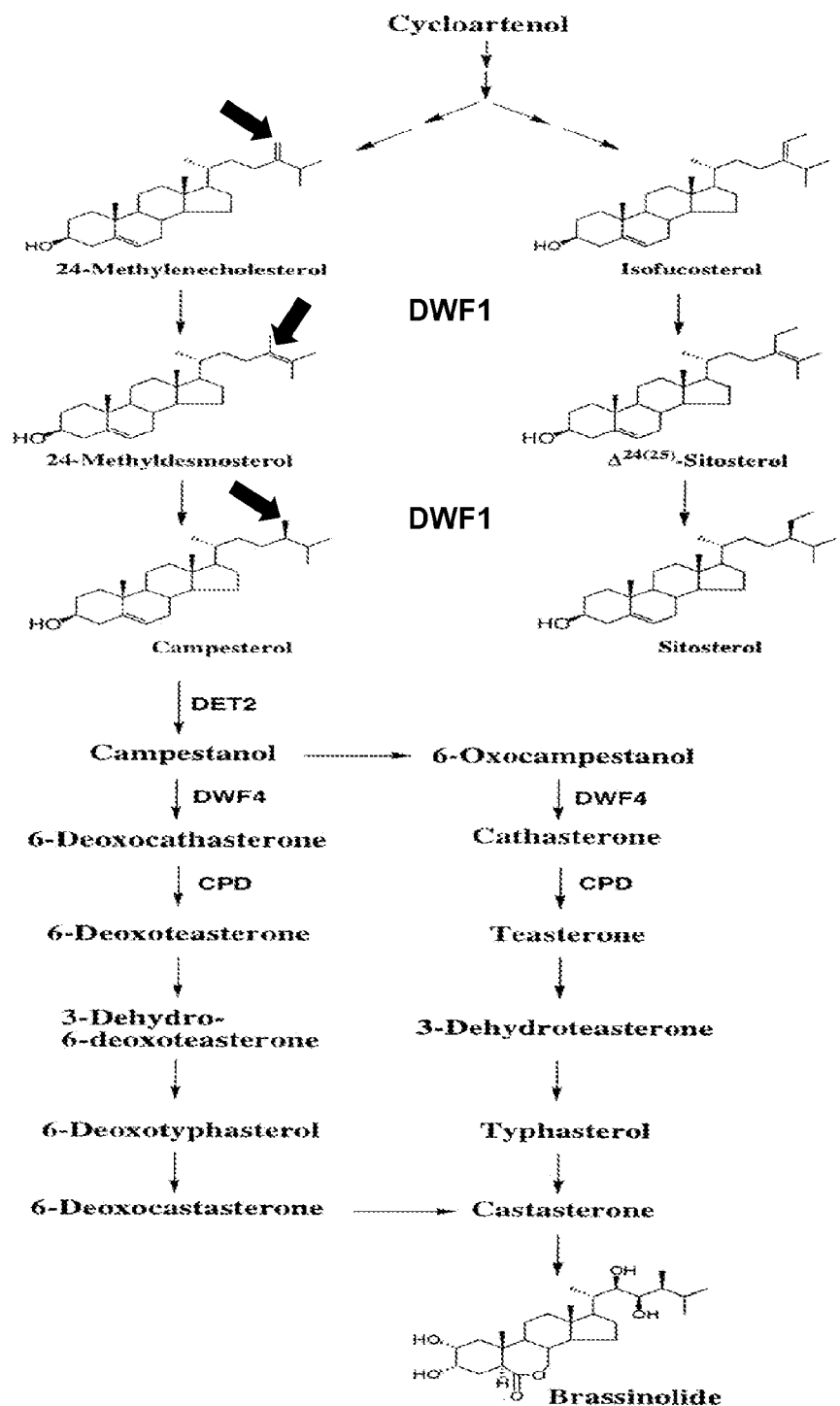
FIG. 1 shows the branched brassinosteroid biosynthetic pathway (from Klahre et al. (1998) Plant Cell 10: 1677-1690). In Arabidopsis, the DWF1/DIM polypeptide is a bifunctional protein which catalyzes the conversion of 24-methylenecholesterol into campesterol, by isomerizing the $\Delta^{24(28)}$ bond into a $\Delta^{24(25)}$ bond and subsequently reducing the double bond (see black arrows). Campesterol is ultimately converted to brassinolide, the active steroid. A similar reaction is catalyzed in the conversion of isofucosterol to sitosterol via $\Delta^{24(25)}$ sitosterol. The reactions that are catalyzed by other enzymes of BR biosynthesis are indicated. DWF4 (Aziproz et al., 1998; Choe et al. 1998 Down), DET2 (Li et al. 1996 Down; Fujioka et al. 1997 Down), and CPD (Szekeres et al. 1996 Down) are shown.

The present invention will now be described with reference to the following examples, which are by way of illustration alone. The following examples are not intended to completely define or to otherwise limit the scope of the invention.

Example 1

Identification of Sequences Related to SEQ ID NO: 1 and SEQ ID NO: 2

Sequences (full length cDNA, ESTs or genomic) related to SEQ ID NO: 1 and/or protein sequences related to SEQ ID NO: 2 were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program was used to find regions of local similarity between sequences by comparing nucleic acid or polypeptide sequences to sequence databases and by calculating the statistical significance of matches. The polypeptide encoded by SEQ ID NO: 1 was used for the TBLASTN algorithm, with default settings and the filter to ignore low complexity sequences set off. The output of the analysis was viewed by pairwise comparison, and ranked according to the probability score (E-value), where the score reflects the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search.

Table A provides a list of nucleic acid and polypeptide sequences related to the nucleic acid sequence as represented by SEQ ID NO: 1 and the polypeptide sequence represented by SEQ ID NO: 2.

TABLE A

Nucleic acid sequences encoding DWF1 polypeptides and DWF1 polypeptides.

| Name | Source organism | Database accession number | Nucleic acid sequence SEQ ID NO: | Polypeptide sequence SEQ ID NO: |
|---|---|---|---|---|
| Sacof_DWF1 | *Saccharum officinarum* | CA272246.1 | 1 | 2 |
|  |  | CA178977.1 |  |  |
|  |  | CA147398.1 |  |  |
| Arath_DWF1 | *Arabidopsis thaliana* | AK226335 | 3 | 4 |
| Brara_DWF1 | *Brassica rapa* | AC189427 | 5 | 6 |
| Glyma_DWF1 | *Glycine max* | CA783178.1 | 7 | 8 |
|  |  | CA801748.1 |  |  |
|  |  | CX548424.1 |  |  |
| Goshi_DWF1 | *Gossypium hirsutum* | AF513859 | 9 | 10 |
| Lyces_DWF1 | *Lycopersicon exculentum* | AY584532 | 11 | 12 |

TABLE A-continued

Nucleic acid sequences encoding DWF1 polypeptides and DWF1 polypeptides.

| Name | Source organism | Database accession number | Nucleic acid sequence SEQ ID NO: | Polypeptide sequence SEQ ID NO: |
|---|---|---|---|---|
| Orysa_DWF1 | *Oryza sativa* | Os10g0397400 | 13 | 14 |
| Pissa_DWF1 | *Pisum sativum* | AF325121 | 15 | 16 |
| Poptr_DWF1 | *Populus tremuloides* | CK091640.1 CK101745.1 CN549251.1 DT491786.1 | 17 | 18 |
| Triae_DWF1 | *Triticum aestivum* | CK217814 | 19 | 20 |
| Zeama_DWF1 | *Zea mays* | AY523572 | 21 | 22 |
| Zinel_DWF1 | *Zinnia elegans* | AB231156 | 23 | 24 |
| Homsa_DWF1 | *Homo sapiens* | AF261758 | 25 | 26 |
| Danre_dhcr24 | *Danio rerio* | NM_001008645 | 27 | 28 |
| Sacof_DWF1 variant I | *Saccharum officinarum* | n.a. | 33 | 34 |
| Sorbi_DWF1 | *Sorghum bicolor* | CD462169 BI075936.1 AW923039 CN136146.1 | 35 | 36 |
| Vitvi_DWF1 | *Vitis vinifera* | AM470510 | 37 | 38 |

Example 2

Alignment of DWF1 Polypeptide Sequences

Figure 4A:
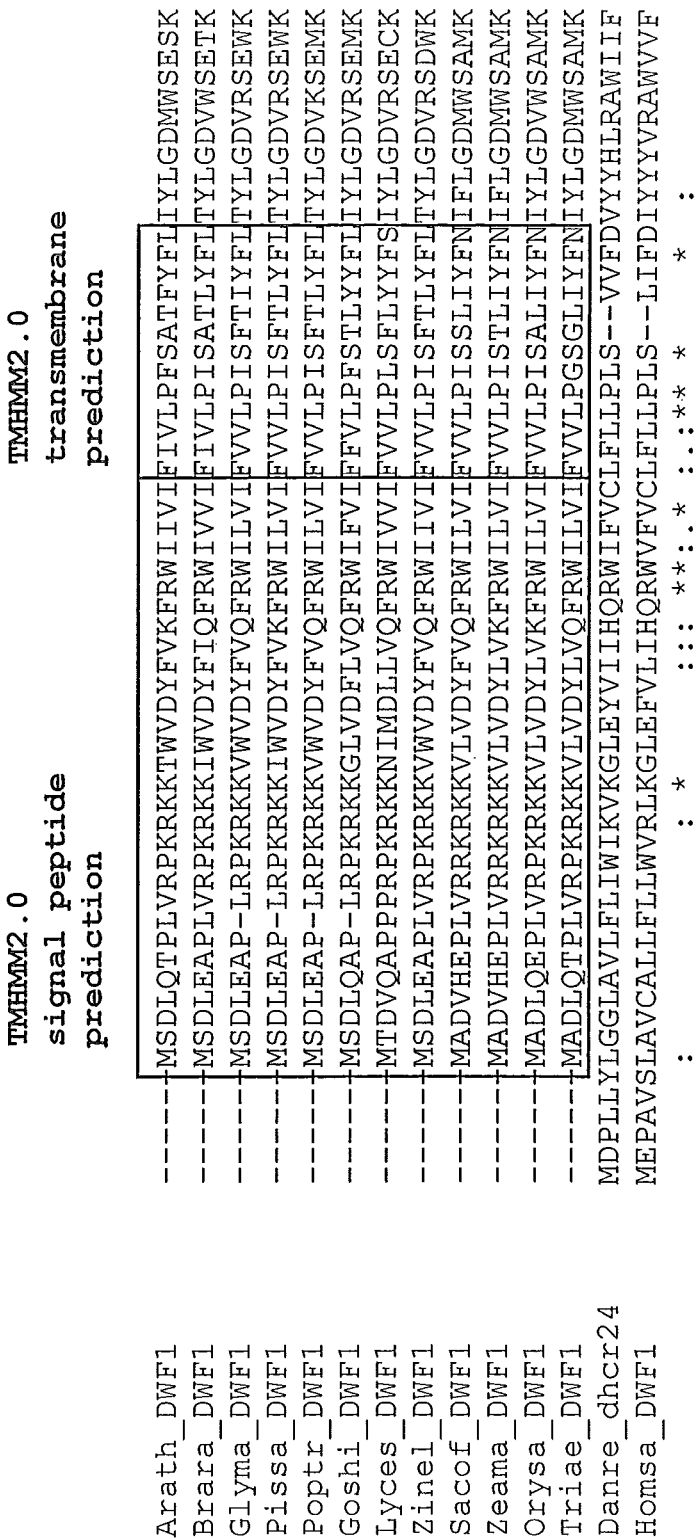

Alignment of polypeptide sequences was performed using the AlignX programme from the Vector NTI (Invitrogen) which is based on the popular Clustal algorithm of progressive alignment (Thompson et al. (1997) Nucleic Acids Res 25:4876-4882; Chenna et al. (2003). Nucleic Acids Res 31:3497-3500). Default values are for the gap open penalty of 10, for the gap extension penalty of 0.1 and the selected weight matrix is Blosum 62 (if polypeptides are aligned). Results in FIG. 4 show that DWF1 polypeptides share regions of high sequence conservation. Among the features highlighted are: (i) a signal peptide (as identified by TMHMM2.0, Example 5); (ii) a single transmembrane domain (as identified by TMHMM2.0, Example 5); (iii) an FAD-binding domain according to Superfamily accession SSF56176, according to the InterPro accession IPR006094, and according to Choe et al. ((1999) Plant Physiol 119: 897-907); within the FAD-binding domain, are boxed subdomains for the binding of pyrophosphate, ADP, isoalloxazine, and adenine (according to Fraaije et al. (1998) Trends Biochem Sci 23: 206-207; Choe et al. (1999) Plant Physiol 119: 897-907); and (iv) the substrate-binding domain, for example as represented by SEQ ID NO: 29 comprised in SEQ ID NO: 2.

Figure 5:
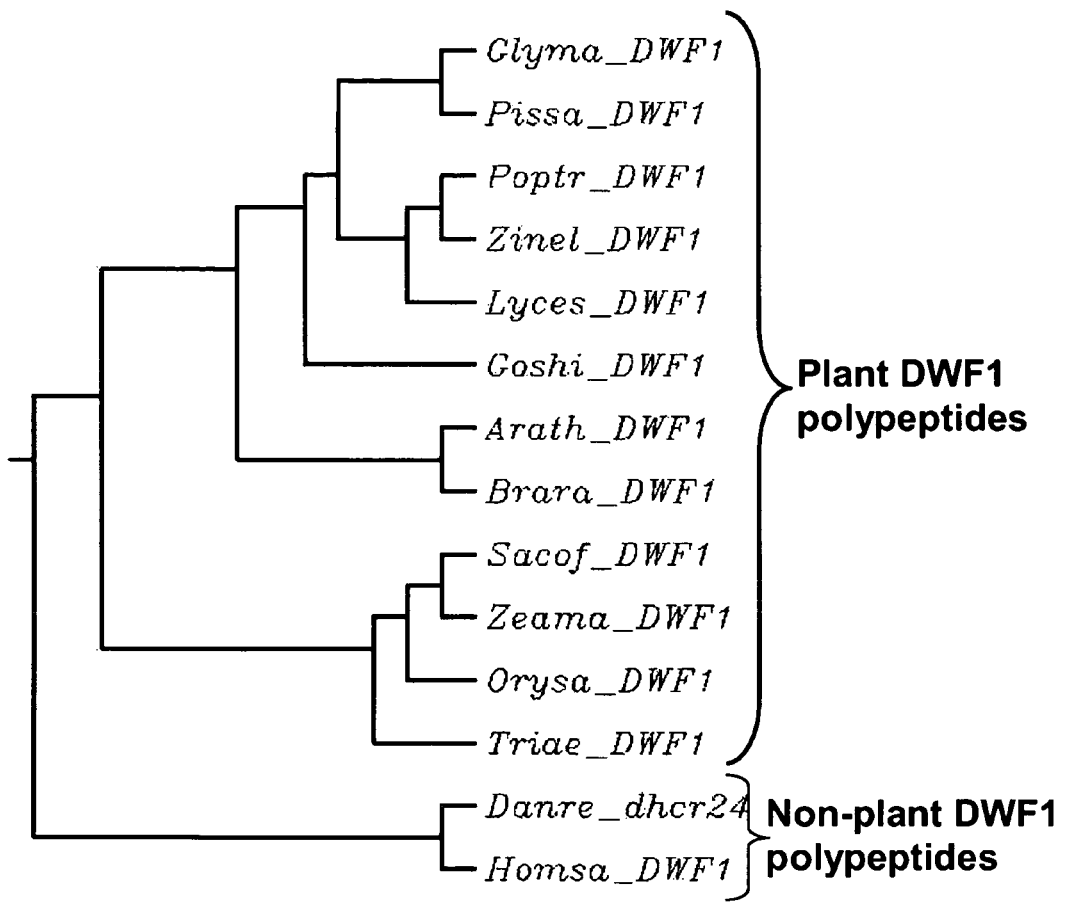
FIG. 5 shows a phylogenetic tree comprising DWF1 polypeptide sequences. Sequences clustering with the sequence of SEQ ID NO: 2 (plant polypeptides) may be useful in performing the methods of the invention.

A phylogenetic tree of DWF1 polypeptides was constructed using a neighbour-joining clustering algorithm as provided with the ClustalW algorithm for multiple sequence alignment hosted at the server of the Kyoto University Bioinformatics Center. FIG. 5 shows how DWF1 polypeptides from plants cluster together with SEQ ID NO: 2, whereas the non-plant DWF1 polypeptides form a separate clade.

Example 3

Calculation of Global Percentage Identity Between Polypeptide Sequences Useful in Performing the Methods of the Invention Global percentages of similarity and identity between full length polypeptide sequences useful in performing the methods of the invention were determined using one of the methods available in the art, the MatGAT (Matrix Global Alignment Tool) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performs a series of pair-wise alignments using the Myers and Miller global alignment algorithm (with a gap opening penalty of 12, and a gap extension penalty of 2), calculates similarity and identity using for example Blosum 62 (for polypeptides), and then places the results in a distance matrix. Sequence similarity is shown in the bottom half of the dividing line and sequence identity is shown in the top half of the diagonal dividing line.

Parameters used in the comparison were:
Scoring matrix: Blosum62
First Gap: 12
Extending gap: 2

Results of the software analysis are shown in Table B for the global similarity and identity over the full length of the polypeptide sequences (excluding the partial polypeptide sequences). Percentage identity is given above the diagonal and percentage similarity is given below the diagonal.

The percentage identity between the polypeptide sequences of plant origin useful in performing the methods of the invention can be as low as 75% amino acid identity compared to SEQ ID NO: 2. The percentage identity between the polypeptide sequences of plant origin and the polypeptides sequences of non-plant origin (for example from *Homo sapiens* and *Danio rerio*) drops down to below 40% identity.

TABLE B

MatGAT results for global similarity and identity over the full length of the DWF1 polypeptide sequences.

| | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 1. Arath_DWF1 | | 87 | 38.4 | 84.5 | 82.8 | 37.6 | 78 | 80 | 80.8 | 83.5 | 79.7 | 79.5 | 79 | 79.6 |
| 2. Brara_DWF1 | 94.5 | | 37.7 | 84.9 | 83.2 | 36.9 | 78.2 | 79.7 | 82.4 | 82.6 | 79.9 | 78.6 | 78.6 | 79.9 |
| 3. Danre_dhcr24 | 57.4 | 57 | | 38.3 | 39 | 79.5 | 37.4 | 38.3 | 38 | 38.5 | 38.3 | 38.4 | 37.8 | 37.5 |
| 4. Glyma_DWF1 | 90.1 | 91.5 | 58 | | 88.4 | 38.6 | 83.8 | 81.9 | 90.3 | 89.1 | 81.5 | 81.3 | 81 | 84.3 |
| 5. Goshi_DWF1 | 91.1 | 90.9 | 57.9 | 93.3 | | 39.7 | 84.2 | 86.3 | 85.9 | 88.8 | 84.2 | 84.6 | 84.2 | 83.3 |
| 6. Homsa_DWF1 | 55.1 | 55.1 | 90.7 | 57.1 | 57 | | 38.2 | 38.8 | 37.7 | 38.4 | 38.6 | 38.6 | 38 | 38.7 |
| 7. Lyces_DWF1 | 88.6 | 89.1 | 56.7 | 92.1 | 91.2 | 56 | | 80.6 | 83.5 | 84.5 | 80.6 | 79.4 | 80.1 | 82 |
| 8. Orysa_DWF1 | 89.7 | 89.7 | 57.6 | 89.9 | 92.2 | 56 | 87.9 | | 80.3 | 84.8 | 95.2 | 92 | 95.4 | 81.9 |
| 9. Pissa_DWF1 | 89.6 | 90.8 | 55.7 | 96.6 | 91.9 | 55 | 92.4 | 88 | | 86.8 | 80.3 | 78.9 | 80.5 | 82.9 |
| 10. Poptr_DWF1 | 92.2 | 93.1 | 56.8 | 94.9 | 94.1 | 56 | 91.2 | 91.3 | 93.8 | | 84.4 | 83.3 | 83.9 | 86.7 |
| 11. Sacof_DWF1 | 89.5 | 89.8 | 57.6 | 89.4 | 91.1 | 55.6 | 87.9 | 98 | 88.2 | 91.3 | | 91.6 | 97.9 | 81.5 |
| 12. Triae_DWF1 | 88.9 | 88.6 | 57.6 | 89.1 | 91.3 | 56.7 | 87.7 | 95.9 | 87.8 | 90.9 | 96.3 | | 90.9 | 79.2 |
| 13. Zeama_DWF1 | 89 | 89 | 57.8 | 89.2 | 91.5 | 55.2 | 87.5 | 97.9 | 88.2 | 90.9 | 98.2 | 95.7 | | 80.7 |
| 14. Zinel_DWF1 | 90.1 | 91.1 | 56.3 | 92.6 | 91.8 | 55.8 | 89.4 | 89.3 | 91.9 | 93.1 | 89.2 | 88.3 | 88.6 | |

The percentage identity between the substrate-binding domains of DWF1 polypeptides, such as the substrate-binding domain of SEQ ID NO: 2 represented in SEQ ID NO: 29, is shown in Table B1. The percentage identity between the substrate-binding domains of plant DWF1 polypeptides is above 75% amino acid identity. The percentage identity between the substrate-binding domains of non-plant DWF1 polypeptides is also above 75% amino acid identity. However, the percentage identity between the substrate-binding domains of plant DWF1 polypeptides and the substratebinding domains of non-plant DWF1 polypeptides is below 40%.

TABLE B1

MatGAT results for global similarity and identity between the substrate-binding domains of the DWF1 polypeptide sequences.

| | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 1. Sacof DWF1 substrate BD | | 81.1 | 82.3 | 81.5 | 84.3 | 80.9 | 96 | 79.2 | 84 | 91.8 | 97.3 | 81.2 | 36.5 | 36.2 |
| 2. Arath DWF1 substrate BD | 89.9 | | 86.9 | 83.9 | 83.7 | 78.5 | 81.1 | 80.4 | 83.4 | 79.6 | 79.9 | 79.1 | 36.2 | 36.8 |
| 3. Brara DWF1 substrate BD | 89.9 | 94.5 | | 83.9 | 84.3 | 78.2 | 81.1 | 81.5 | 81.6 | 79.6 | 80.9 | 78.8 | 35.3 | 35.9 |
| 4. Glyma DWF1 substrate BD | 88.4 | 89.3 | 89.9 | | 89 | 84.2 | 81.5 | 89.9 | 87.5 | 80.9 | 81.2 | 83 | 37.2 | 35.7 |
| 5. Goshi DWF1 substrate BD | 90.3 | 91.8 | 91.5 | 93.7 | | 83.6 | 86 | 89.1 | 83.7 | 84 | 83.4 | 36.7 | 35.2 |
| 6. Lyces DWF1 substrate BD | 86.9 | 87.5 | 88.1 | 91.9 | 90.1 | | 80 | 84.2 | 83.6 | 78.2 | 80 | 81.8 | 37.2 | 36 |
| 7. Orysa DWF1 substrate BD | 97.6 | 89.9 | 89.6 | 89 | 91.5 | 86 | | 78.3 | 84 | 90.9 | 95.7 | 80.9 | 36.2 | 35.9 |
| 8. Pissa DWF1 substrate BD | 86.9 | 88.1 | 89 | 94.6 | 91.4 | 92 | 86.3 | | 85.1 | 78 | 78.9 | 81 | 36.7 | 35.5 |
| 9. Poptr DWF1 substrate BD | 90 | 91.5 | 91.5 | 92.8 | 94.3 | 89.9 | 89.7 | 91.1 | | 81.9 | 83.7 | 84.9 | 37.3 | 35.5 |
| 10. Triae DWF1 substrate BD | 96 | 89.3 | 89 | 88.4 | 90.6 | 86.3 | 94.5 | 86.9 | 90 | | 90.6 | 77.6 | 36.2 | 35.9 |
| 11. Zeama DWF1 substrate BD | 97.3 | 89.7 | 89.1 | 88.4 | 90.6 | 86 | 97.3 | 86.6 | 89.7 | 94.8 | | 80.4 | 35.2 | 35.5 |
| 12. Zinal DWF1 substrate BD | 88.2 | 88.8 | 89.1 | 90.1 | 92.1 | 88.4 | 88.2 | 89.3 | 90 | 87.3 | 87.6 | | 38.4 | 36.7 |
| 13. Homsa DWF1 substrate BD | 54 | 54.6 | 53.7 | 53.4 | 53.8 | 53.1 | 54.3 | 51.2 | 53.5 | 55.2 | 52.9 | 54.8 | | 79.7 |
| 14. Danre DHCR24 substrate BD | 55.2 | 56.7 | 55.5 | 53.4 | 53.2 | 52.8 | 55.2 | 52.1 | 53.2 | 55.5 | 54.7 | 54.2 | 89.3 | |

Example 4

Identification of Domains Comprised in Polypeptide Sequences Useful in Performing the Methods of the Invention The Integrated Resource of Protein Families, Domains and Sites (InterPro) database is an integrated interface for the commonly used signature databases for text- and sequence-based searches. The InterPro database combines these databases, which use different methodologies and varying degrees of biological information about well-characterized proteins to derive protein signatures. Collaborating databases include SWISS-PROT, PROSITE, TrEMBL, PRINTS, Pro-Dom and Pfam, Smart and TIGRFAMs. Interpro is hosted at the European Bioinformatics Institute in the United Kingdom.

The results of the InterPro scan of the polypeptide sequence as represented by SEQ ID NO: 2 are presented in Table C and FIG. 4.

TABLE C

InterPro scan results (major accession numbers) of the polypeptide sequence as represented by SEQ ID NO: 2.

| Database | Accession number | Accession name | Amino acid position on SEQ ID NO 2 |
|---|---|---|---|
| InterPro | IPR006094 | FAD linked oxidase, N-terminal | 110-200 |
| Pfam | PF01565 | FAD_binding_4 | 110-200 |
| Panther | PTHR10801 | CELL ELONGATION PROTEIN DIMINUTO-RELATED | 1-558 |
| SuperFamily | SSF56176 | FAD-binding domain | 52-233 |

Various enzymes use FAD as a co-factor, most of these enzymes are oxygen-dependent oxidoreductases, either binding the FAD group covalently, or by a dissociable bond, which appears to be the case of DWF1 polypeptides.

The FAD-binding domain comprises subdomains for the binding of pyrophosphate, ADP, isoalloxazine, and adenine (Fraaije et al. (1998) Trends Biochem Sci 23: 206-207; Choe et al. (1999) Plant Physiol 119: 897-907). These are boxed in FIG. 4.

Downstream of the FAD-binding domain (C-terminus of the DWF1 polypeptides), is the substratebinding domain (such as SEQ ID NO: 29 comprised in the DWF1 polypeptide of SEQ ID NO: 2), involved in the two-step conversion of 24-methylenecholesterol to campesterol (also of isofucosterol to sitosterol), via isomerisation of the Δhu 24(28) bond into a $\Delta^{24(25)}$ bond, followed by reduction of the double bond (Khlare et al. (1998) Plant Cell 10: 1677-1690).

Example 5

Topology Prediction of the Polypeptide Sequences Useful in Performing the Methods of the Invention (Subcellular Localization, Transmembrane . . . )

Figure 2:
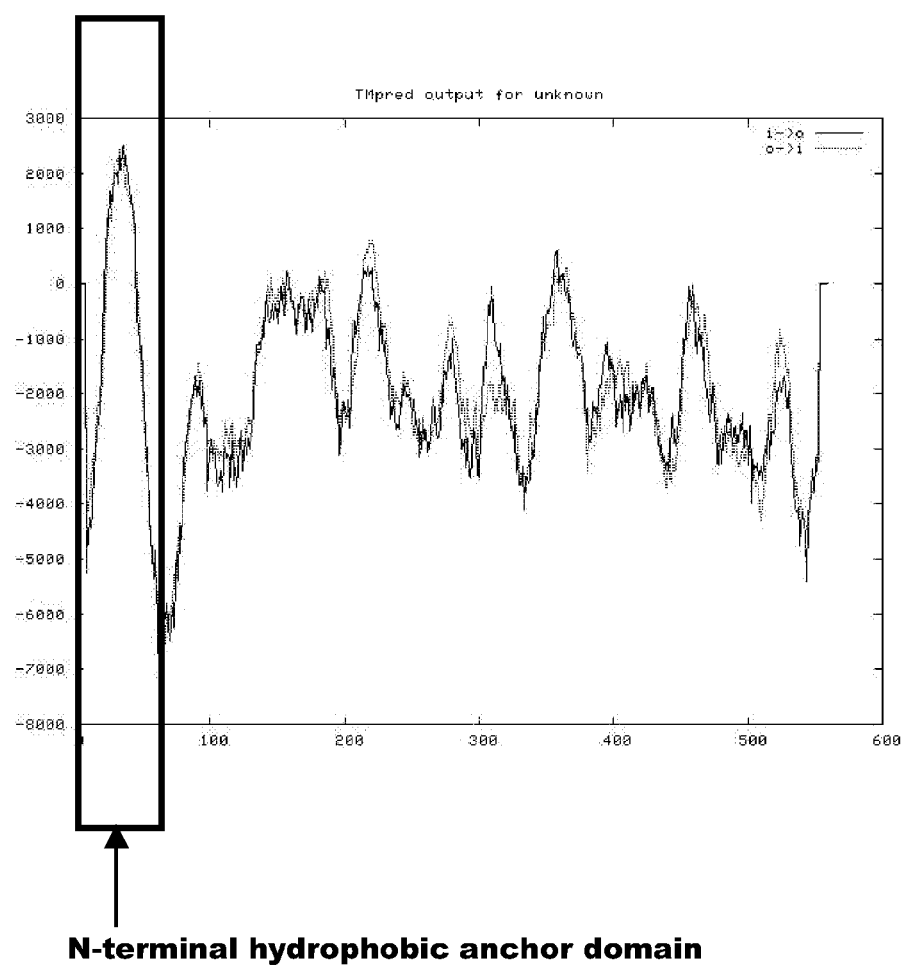
FIG. 2 shows a prediction of the hydropathy of the DWF1 polypeptide as represented by SEQ ID NO: 2, using the TMpred algorithm (Hofmann and Stoffel (2003) Biol. Chem. Hoppe-Seyler 374, 166) at the EMBNet hosted by the Swiss Institute of Bioinformatics. An N-terminal hydrophobic stretch is clearly discernible, that probably anchors the protein on the cytosolic face of an endomembrane.

The TMpred program makes a prediction of membrane-spanning regions and their orientation. The algorithm is based on the statistical analysis of TMbase, a database of naturally occurring transmembrane proteins. The prediction is made using a combination of several weight-matrices for scoring (Hofmann and Stoffel (2003) Biol. Chem. Hoppe-Seyler 374, 166). The algorithm can be found at the EMBNet hosted by the Swiss Institute of Bioinformatics. An N-terminal hydrophobic stretch is clearly discernible when SEQ ID NO: 2 is analysed using this algorithm, that probably anchors the protein on the cytosolic face of an endomembrane (FIG. 2).

Figure 3:
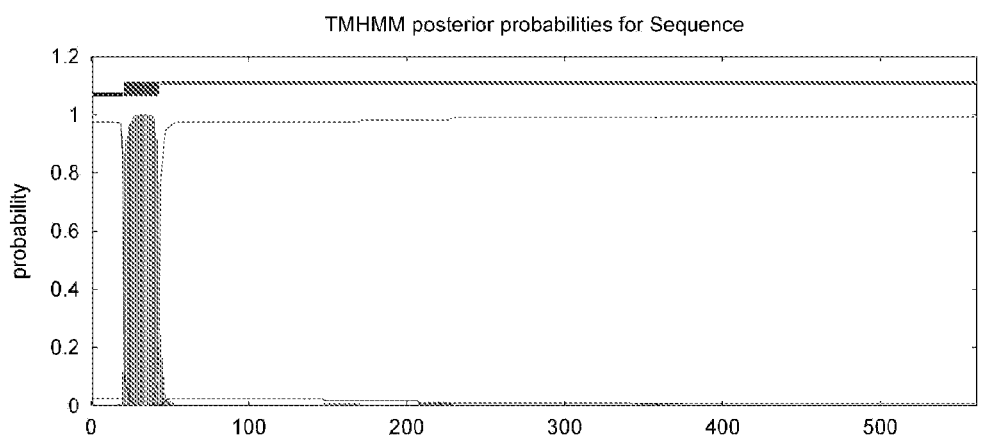
FIG. 3 shows the output of the predicted location and orientation of alpha helices in membrane-spanning proteins of the DWF1 polypeptide as represented by SEQ ID NO: 2 using the TMHMM2.0 algorithm (hosted on the server of the Technical University of Denmark). The polypeptide comprises only one membrane-spanning domain, the majority of the protein is facing the cytosol, while the N-terminus is anchored in a membrane, most likely an endomembrane system such as the endoplasmic reticulum (ER), the Golgi apparatus, and mitochondria.

The prediction of the location and orientation of alpha helices in membrane-spanning proteins is done using the TMHMM2.0 algorithm based on a hidden Markov model (HMM) (hosted on the server of the Technical University of Denmark). Results of the analysis performed on the polypeptide as represented by SEQ ID NO: 2 is shown in Table D below, and illustrated in FIG. 3. The polypeptide comprises only one membrane-spanning domain, the majority of the protein is facing the cytosol, while the N-terminus is anchored in a membrane, most likely an endomembrane system such as the endoplasmic reticulum (ER), the Golgi apparatus, and mitochondria.

TABLE D output of TMHMM2.0 algorithm on the polypeptide sequence of SEQ ID NO: 2

| Position relative to plasma membrane | Amino acids from N-terminus to C-terminus of SEQ ID NO: 2 | Corresponding domain on the polypeptide sequence of SEQ ID NO: 2 |
| --- | --- | --- |
| Sequence inside | 1-20 | hydrophobic N-terminus |
| Transmembrane helix | 21-43 | transmembrane domain |
| Sequence outside | 44-561 | Comprising the FAD-binding domain and substrate-binding domain |

Algorithms to perform subcellular localization analyses, include:
TargetP 1.1 maintained at the server of the Technical University of Denmark
ChloroP 1.1 hosted on the server of the Technical University of Denmark;
Protein Prowler Subcellular Localisation Predictor version 1.2 hosted on the server of the Institute for Molecular Bioscience, University of Queensland, Brisbane, Australia;
PENCE Proteome Analyst PA-GOSUB 2.5 hosted on the server of the University of Alberta, Edmonton, Alberta, Canada;

Example 6

Assay Related to the Polypeptide Sequences Useful in Performing the Methods of the Invention Measurements of endogenous sterols and metabolites of exogenously added, deuterium-labeled 24-methylenecholesterol (substrate feeding experiments) are well known in the art, and are thoroughly described in, for example, Fujioka et al. (2002) Plant Physiol 130: 930-939; He et al. (2003) Plant Physiol 131: 1258-1269; or Hong et al. (2005) Plant Cell 17: 2243-2254.

Complementation assays may also be performed to identify DWF1 polypeptide useful in performing the methods of the invention. Plants mutants characterized lacking DWF1 activity are well known in the art, for example, the dim and dwf1 mutants in *Arabidopsis thaliana* (Klahre et al. (1998) Plant Cell 10: 1677-1690; Choe et al. (1999) Plant Physiol 119: 897-907), and the brd2 mutant in rice (Hong et al. (2005) Plant Cell 17: 2243-2254). By introducing and expressing in such mutant plants, a nucleic acid sequence encoding a DWF1 polypeptide as defined hereinabove, the normal plant phenotype is restored.

Example 7

Cloning of Nucleic Acid Sequence as Represented by SEQ ID NO: 33

Unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfax (1993) by R. D. D. Croy, published by BIOS Scientific Publications Ltd (UK) and Blackwell Scientific Publications (UK).

The *Saccharum officinarum* DWF1 gene was amplified by PCR using as template sugarcane cDNA synthesized from mRNA extracted from mixed plant tissues. Primers (SEQ ID NO: 30; sense: 5'-GGGGACAAGTTTGTACAAAAAAGCAG-GCTTCACAATGGCGGACGTGCATGAACC-3') and SEQ ID NO: 31; reverse, complementary: 5'-GGGGACCACTTTGTACAA-GAAAGCTGGGTTT AGGCCTCGTCCGCGTAGG-3'), which include the AttB sites for Gateway recombination, were used for PCR amplification. PCR was performed using Hifi Taq DNA polymerase in standard conditions. A PCR fragment of the expected length (including attB sites) was amplified and purified also using standard methods. The first step of the Gateway procedure, the BP reaction, was then performed, during which the PCR fragment recombined in vivo with the pDONR201 plasmid to produce, according to the Gateway terminology, an "entry clone". Plasmid pDONR201 was purchased from Invitrogen, as part of the Gateway® technology.

Example 8

Expression Vector Construction Using the Nucleic Acid Sequence as Represented by SEQ ID NO: 33

The entry clone comprising SEQ ID NO: 33 was subsequently used in an LR reaction with a destination vector used for *Oryza sativa* transformation. This vector contained as functional elements within the T-DNA borders: a plant selectable marker; a screenable marker expression cassette; and a Gateway cassette intended for LR in vivo recombination with the nucleic acid sequence of interest already cloned in the entry clone. A rice GOS2 promoter (SEQ ID NO: 32 or SEQ ID NO: 39) for constitutive expression was located upstream of this Gateway cassette.

Figure 6:
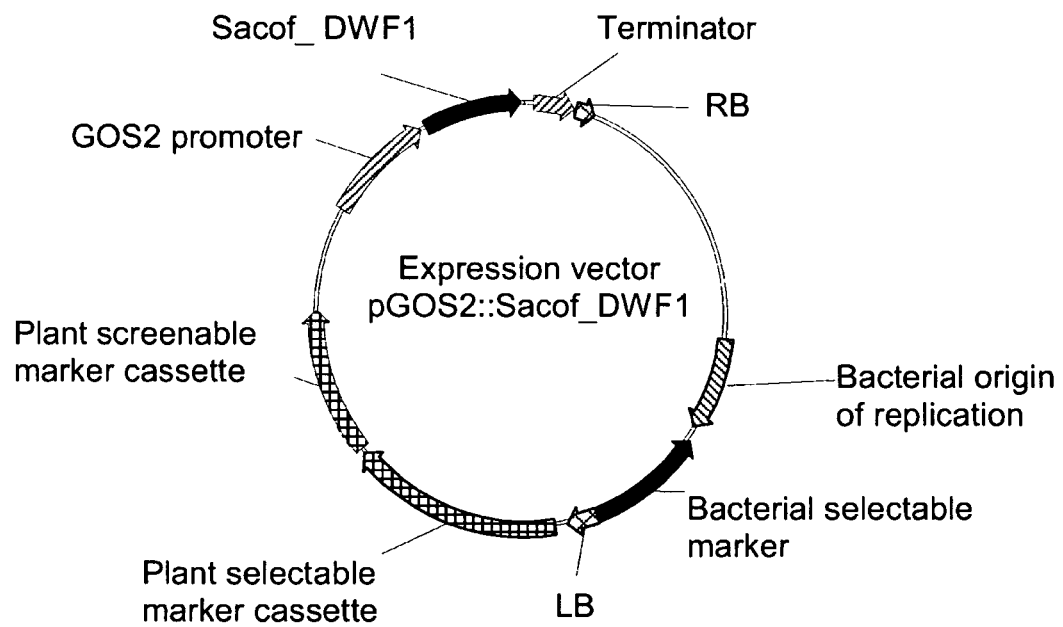
FIG. 6 shows the binary vector for increased expression in *Oryza sativa* of a *Saccharum officinarum* nucleic acid sequence encoding a DWF1 polypeptide under the control of a GOS2 promoter.

After the LR recombination step, the resulting expression vector pGOS2::DWF1 (FIG. 6) was transformed into Agrobacterium strain LBA4044 according to methods well known in the art.

Example 9

Plant Transformation

Rice Transformation

The *Agrobacterium* containing the expression vector was used to transform *Oryza sativa* plants. Mature dry seeds of the rice japonica cultivar Nipponbare were dehusked. Sterilization was carried out by incubating for one minute in 70% ethanol, followed by 30 minutes in 0.2% $HgCl_2$, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity).

*Agrobacterium* strain LBA4404 containing the expression vector was used for co-cultivation. *Agrobacterium* was inoculated on AB medium with the appropriate antibiotics and cultured for 3 days at 28° C. The bacteria were then collected and suspended in liquid co-cultivation medium to a density ($OD_{600}$) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

Approximately 35 independent T0 rice transformants were generated for one construct. The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodges 1996, Chan et al. 1993, Hiei et al. 1994).

Example 10

Phenotypic Evaluation Procedure 10.1 Evaluation Setup

Approximately 35 independent T0 rice transformants were generated. The primary transformants were transferred from a tissue culture chamber to a greenhouse for growing and harvest of T1 seed. Seven events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The transgenic plants and the corresponding nullizygotes were grown side-by-side at random positions. Greenhouse conditions were of shorts days (12 hours light), 28° C. in the light and 22° C. in the dark, and a relative humidity of 70%.

Four T1 events were further evaluated in the T2 generation following the same evaluation procedure as for the T1 generation but with more individuals per event. From the stage of sowing until the stage of maturity the plants were passed several times through a digital imaging cabinet. At each time point digital images (2048×1536 pixels, 16 million colours) were taken of each plant from at least 6 different angles.

10.2 Statistical Analysis: F-Test

A two factor ANOVA (analysis of variants) was used as a statistical model for the overall evaluation of plant phenotypic characteristics. An F-test was carried out on all the parameters measured of all the plants of all the events transformed with the gene of the present invention. The F-test was carried out to check for an effect of the gene over all the transformation events and to verify for an overall effect of the gene, also known as a global gene effect. The threshold for significance for a true global gene effect was set at a 5% probability level for the F-test. A significant F-test value points to a gene effect, meaning that it is not only the mere presence or position of the gene that is causing the differences in phenotype.

10.3 Parameters Measured

Biomass-Related Parameter Measurement

From the stage of sowing until the stage of maturity the plants were passed several times through a digital imaging cabinet. At each time point digital images (2048×1536 pixels, 16 million colours) were taken of each plant from at least 6 different angles.

The plant aboveground area (or leafy biomass) was determined by counting the total number of pixels on the digital images from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The above ground area is the area measured at the time point at which the plant had reached its maximal leafy biomass. The early vigour is the plant (seedling) aboveground area three weeks post-germination. Increase in root biomass is expressed as an increase in total root biomass (measured as maximum biomass of roots observed during the lifespan of a plant); or as an increase in the root/shoot index (measured as the ratio between root mass and shoot mass in the period of active growth of root and shoot).

Seed-Related Parameter Measurements

The mature primary panicles were harvested, counted, bagged, barcode-labelled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed weight per plant was measured by weighing all filled husks harvested from one plant. Total seed number per plant was measured by counting the number of husks harvested from a plant. Thousand Kernel Weight (TKW) is extrapolated from the number of filled seeds counted and their total weight. The Harvest Index (HI) in the present invention is defined as the ratio between the total seed weight per plant and the above ground area ($mm^2$), multiplied by a factor $10^6$. The total number of flowers per panicle as defined in the present invention is the ratio between the total number of seeds and the number of mature primary panicles. The seed fill rate as defined in the present invention is the proportion (expressed as a %) of the number of filled seeds over the total number of seeds (or florets).

Example 11

Results of the Phenotypic Evaluation of the Transgenic Rice Plants

The results of the evaluation of transgenic rice plants expressing the DWF1 nucleic acid sequence are as follows.

There was a significant increase in the total seed weight per plant and the Thousand Kernel Weight of the transgenics compared to corresponding nullizygotes (controls).

| | Average % increase of three best performing events in T1 generation | Average % increase of three best performing events in T2 generation |
|---|---|---|
| Total seed weight per plant | 18% | 16% |
| TKW | 4% | 3% |

Example 12

Examples of Transformation of Other Crops

Corn Transformation

Transformation of maize (*Zea mays*) is performed with a modification of the method described by Ishida et al. (1996) Nature Biotech 14(6): 745-50. Transformation is genotype-dependent in corn and only specific genotypes are amenable to transformation and regeneration. The inbred line A188 (University of Minnesota) or hybrids with A188 as a parent are good sources of donor material for transformation, but other genotypes can be used successfully as well. Ears are harvested from corn plant approximately 11 days after pollination (DAP) when the length of the immature embryo is about 1 to 1.2 mm. Immature embryos are cocultivated with *Agrobacterium tumefaciens* containing the expression vector, and transgenic plants are recovered through organogenesis. Excised embryos are grown on callus induction medium, then maize regeneration medium, containing the selection agent (for example imidazolinone but various selection markers can be used). The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Wheat Transformation

Transformation of wheat is performed with the method described by Ishida et al. (1996) Nature Biotech 14(6): 745-50. The cultivar Bobwhite (available from CIMMYT, Mexico) is commonly used in transformation. Immature embryos are co-cultivated with *Agrobacterium tumefaciens* containing the expression vector, and transgenic plants are recovered through organogenesis. After incubation with *Agrobacterium*, the embryos are grown in vitro on callus induction medium, then regeneration medium, containing the selection agent (for example imidazolinone but various selection markers can be used). The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Soybean Transformation

Soybean is transformed according to a modification of the method described in the Texas A&M U.S. Pat. No. 5,164,310. Several commercial soybean varieties are amenable to transformation by this method. The cultivar Jack (available from the Illinois Seed foundation) is commonly used for transformation. Soybean seeds are sterilised for in vitro sowing. The hypocotyl, the radicle and one cotyledon are excised from seven-day old young seedlings. The epicotyl and the remaining cotyledon are further grown to develop axillary nodes. These axillary nodes are excised and incubated with *Agrobacterium tumefaciens* containing the expression vector. After the cocultivation treatment, the explants are washed and transferred to selection media. Regenerated shoots are excised and placed on a shoot elongation medium. Shoots no longer than 1 cm are placed on rooting medium until roots develop. The rooted shoots are transplanted to soil in the greenhouse. T1 seeds are produced from plants that exhibit tolerance to the selection agent and that contain a single copy of the T-DNA insert.

Rapeseed/Canola Transformation

Cotyledonary petioles and hypocotyls of 5-6 day old young seedling are used as explants for tissue culture and transformed according to Babic et al. (1998, Plant Cell Rep 17: 183-188). The commercial cultivar Westar (Agriculture Canada) is the standard variety used for transformation, but other varieties can also be used. Canola seeds are surface-sterilized for in vitro sowing. The cotyledon petiole explants with the cotyledon attached are excised from the in vitro seedlings, and inoculated with *Agrobacterium* (containing the expression vector) by dipping the cut end of the petiole explant into the bacterial suspension. The explants are then cultured for 2 days on MSBAP-3 medium containing 3 mg/l BAP, 3% sucrose, 0.7% Phytagar at 23° C., 16 hr light. After two days of co-cultivation with *Agrobacterium*, the petiole explants are transferred to MSBAP-3 medium containing 3 mg/l BAP, cefotaxime, carbenicillin, or timentin (300 mg/l) for 7 days, and then cultured on MSBAP-3 medium with cefotaxime, carbenicillin, or timentin and selection agent until shoot regeneration. When the shoots are 5-10 mm in length, they are cut and transferred to shoot elongation medium (MSBAP-0.5, containing 0.5 mg/l BAP). Shoots of about 2 cm in length are transferred to the rooting medium (MS0) for root induction. The rooted shoots are transplanted to soil in the greenhouse. T1 seeds are produced from plants that exhibit tolerance to the selection agent and that contain a single copy of the T-DNA insert.

Alfalfa Transformation

A regenerating clone of alfalfa (*Medicago sativa*) is transformed using the method of (McKersie et al., 1999 Plant Physiol 119: 839-847). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown D C W and A Atanassov (1985. Plant Cell Tissue Organ Culture 4: 111-112). Alternatively, the RA3 variety (University of Wisconsin) has been selected for use in tissue culture (Walker et al., 1978 Am J Bot 65:654-659). Petiole explants are cocultivated with an overnight culture of *Agrobacterium tumefaciens* C58C1 pMP90 (McKersie et al., 1999 Plant Physiol 119: 839-847) or LBA4404 containing the expression vector. The explants are cocultivated for 3 d in the dark on SH induction medium containing 288 mg/L Pro, 53 mg/L thioproline, 4.35 g/L K2SO4, and 100 μm acetosyringinone. The explants are washed in half-strength Murashige-Skoog medium (Murashige and Skoog, 1962) and plated on the same SH induction medium without acetosyringinone but with a suitable selection agent and suitable antibiotic to inhibit *Agrobacterium* growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings were transplanted into pots and grown in a greenhouse. T1 seeds are produced from plants that exhibit tolerance to the selection agent and that contain a single copy of the T-DNA insert.

Cotton Transformation

Cotton (*Gossypium hirsutum* L.) transformation is performed using *Agrobacterium tumefaciens*, on hypocotyls explants. The commercial cultivars such as Coker 130 or Coker 312 (SeedCo, Lubbock, Tex.) are standard varieties used for transformation, but other varieties can also be used. The seeds are surface sterilized and germinated in the dark. Hypocotyl explants are cut from the germinated seedlings to lengths of about 1-1.5 centimeter. The hypotocyl explant is submersed in the Agrobacterium tumefaciens inoculum containing the expression vector, for 5 minutes then co-cultivated for about 48 hours on MS+1.8 mg/l KNO3+2% glucose at 24° C., in the dark. The explants are transferred the same medium containing appropriate bacterial and plant selectable markers (renewed several times), until embryogenic calli is seen. The calli are separated and subcultured until somatic embryos appear. Plantlets derived from the somatic embryos are matured on rooting medium until roots develop. The rooted shoots are transplanted to potting soil in the greenhouse. T1 seeds are produced from plants that exhibit tolerance to the selection agent and that contain a single copy of the T-DNA insert.

Example 13

Examples of Abiotic Stress Screens

Drought Screen

Plants from a selected number of events are grown in potting soil under normal conditions until they approached the heading stage. They are then transferred to a "dry" section where irrigation is withheld. Humidity probes are inserted in randomly chosen pots to monitor the soil water content (SWC). When SWC go below certain thresholds, the plants are automatically re-watered continuously until a normal level is reached again. The plants are then re-transferred to normal conditions. The rest of the cultivation (plant maturation, seed harvest) is the same as for plants not grown under abiotic stress conditions. Growth and yield parameters are recorded as detailed for growth under normal conditions.

Salt Stress Screen

Plants are grown on a substrate made of coco fibers and argex (3 to 1 ratio). A normal nutrient solution is used during the first two weeks after transplanting the plantlets in the greenhouse. After the first two weeks, 25 mM of salt (NaCl) is added to the nutrient solution, until the plants were harvested. Growth and yield parameters are recorded as detailed for growth under normal conditions.

Reduced Nutrient (Nitrogen) Availability Screen

Plants from six events (T2 seeds) are grown in potting soil under normal conditions except for the nutrient solution. The pots are watered from transplantation to maturation with a specific nutrient solution containing reduced N nitrogen (N) content, usually between 7 to 8 times less. The rest of the cultivation (plant maturation, seed harvest) is the same as for plants not grown under abiotic stress. Growth and yield parameters are recorded as detailed for growth under normal conditions.

The invention claimed is:

1. A method for increasing seed yield in plants relative to control plants, comprising increasing expression in a plant of a nucleic acid sequence encoding a Dwarf1 (DWF1) polypeptide, wherein the DWF1 polypeptide comprises from N-terminus to C-terminus: (i) a transmembrane domain; (ii) an FAD-binding domain; and (iii) a substrate-binding domain having at least 98% sequence identity to the substrate-binding domain of SEQ ID NO: 29, and selecting for a plant having increased seed yield relative to a corresponding control plant.

2. The method of claim 1, wherein said DWF1 polypeptide has at least 99% sequence identity to the amino acid sequence of SEQ ID NO: 2 or SEQ ID NO: 34.

3. The method of claim 1, wherein said nucleic acid sequence comprises the nucleic acid sequence of SEQ ID NO: 1 or 33 or encodes a polypeptide comprising the amino acid sequence of SEQ ID NO: 2 or 34.

4. The method of claim 1, wherein said increased expression is effected by introducing and expressing in a plant the nucleic acid sequence encoding the DWF1 polypeptide.

5. The method of claim 4, wherein said nucleic acid sequence is operably linked to a constitutive promoter.

6. The method of claim 1, wherein said increased seed yield is one or both of increased thousand kernel weight (TKW) or increased total seed weight per plant.

7. The method of claim 1, wherein said nucleic acid sequence encoding a DWF1 polypeptide is of plant origin.

8. A method for the production of a transgenic plant having increased seed yield relative to control plants, comprising:
(a) introducing and expressing in a plant a nucleic acid sequence encoding a DWF1 polypeptide, wherein the DWF1 polypeptide comprises from N-terminus to C-terminus: (i) a transmembrane domain; (ii) an FAD-binding domain; and (iii) a substrate-binding domain having at least 98% sequence identity to the substrate-binding domain of SEQ ID NO: 29; and
(b) cultivating the plant or plant cell under conditions promoting plant growth and development, and
(c) selecting for a plant having increased seed yield relative to a corresponding control plant.

9. The method of claim 8, wherein said increased seed yield is one or both of increased thousand kernel weight (TKW) or increased total seed weight per plant.

10. A transgenic plant having increased seed yield relative to control plants, resulting from increased expression of a nucleic acid sequence encoding a DWF1 polypeptide, wherein the DWF1 polypeptide comprises from N-terminus to C-terminus: (i) a transmembrane domain; (ii) an FAD-binding domain; and (iii) a substrate-binding domain having at least 98% sequence identity to the substrate-binding domain of SEQ ID NO: 29, or a transgenic plant cell derived from said transgenic plant.

11. The transgenic plant of claim 10, wherein said plant is a crop plant, a monocot, a cereal, rice, maize, wheat, barley, millet, rye, triticale, sorghum, or oats, or a transgenic plant cell derived from said plant.

12. Harvestable parts, including seeds, of the transgenic plant of claim 10, wherein said harvestable parts or seeds comprise said nucleic acid sequence encoding a DWF1 polypeptide.

13. Products derived from the transgenic plant of claim 10 and/or from harvestable parts of said plant, wherein the products comprise said nucleic acid sequence encoding a DWF1 polypeptide.

14. The transgenic plant of claim 10, wherein the substrate-binding domain comprises the substrate-binding domain of SEQ ID NO: 29, or a transgenic plant cell derived from said transgenic plant.

15. An isolated polypeptide having at least 99% sequence identity to the amino acid sequence of SEQ ID NO: 2 or 34.

16. An isolated nucleic acid encoding the polypeptide of claim 15.

17. An isolated polypeptide comprising from N-terminus to C-terminus:
(i) a transmembrane domain;
(ii) a FAD-binding domain; and
(iii) a substrate-binding domain having at least 99% or more sequence identity to the substrate-binding domain of SEQ ID NO: 29.

18. An isolated nucleic acid encoding the polypeptide of claim 17.

19. An isolated nucleic acid comprising the nucleic acid sequence of SEQ ID NO: 1 or 33 or encoding a polypeptide comprising the amino acid sequence of SEQ ID NO: 2 or 34.

20. A construct comprising:
a) a nucleic acid sequence encoding a DWF1 polypeptide, wherein the nucleic acid has at least 90% sequence identity to the nucleic acid sequence of SEQ ID NO: 1 or 33;

b) one or more control sequences capable of driving expression of the nucleic acid sequence of (a); and optionally c) a transcription termination sequence.

21. The construct of claim 20, wherein said one or more control sequences is a constitutive promoter.

22. The construct of claim 20, wherein said one or more control sequences is a GOS2 promoter.

23. The construct of claim 20, wherein said nucleic acid sequence has at least 95% identity to the nucleic acid sequence of SEQ ID NO: 1 or 33.

24. A plant cell, plant, part thereof or progeny therefrom comprising the construct of claim 20.

25. A method for increasing seed yield in plants relative to control plants, comprising introducing into a plant the construct of claim 20, and selecting for a plant having increased seed yield relative to a corresponding control plant.

26. A method for the production of a transgenic plant having increased seed yield relative to control plants, comprising:

(a) introducing into a plant the construct of claim 20;

(b) cultivating the plant under conditions promoting plant growth and development; and (c) selecting for a plant having increased seed yield relative to a corresponding control plant.

27. A construct comprising:

a) a nucleic acid sequence encoding a DWF1 polypeptide, wherein the DWF1 polypeptide comprises from N-terminus to C-terminus: (i) a transmembrane domain;
(ii) an FAD-binding domain; and (iii) a substrate-binding domain having at least 99% sequence identity to the substrate-binding domain of SEQ ID NO: 29;

b) one or more control sequences capable of driving expression of the nucleic acid sequence of (a); and optionally c) a transcription termination sequence.

28. A plant cell, plant, part thereof or progeny therefrom comprising the construct of claim 27.

\* \* \* \* \*

UNITED STATES PATENT AND TRADEMARK OFFICE
CERTIFICATE OF CORRECTION

PATENT NO. : 8,461,413 B2  Page 1 of 1
APPLICATION NO. : 12/524746
DATED : June 11, 2013
INVENTOR(S) : Valerie Frankard It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 528 days.

Signed and Sealed this

Eighth Day of September, 2015

Michelle K. Lee
*Director of the United States Patent and Trademark Office*